(12) United States Patent
Akabayov

(10) Patent No.: US 11,339,189 B2
(45) Date of Patent: May 24, 2022

(54) DNA PRIMASE AND GYRASE INHIBITORS

(71) Applicant: B. G. NEGEV TECHNOLOGIES AND APPLICATIONS LTD., AT BEN-GURION UNIVERSITY, Beer Sheva (IL)

(72) Inventor: Barak Akabayov, Omer (IL)

(73) Assignee: B. G. NEGEV TECHNOLOGIES AND APPLICATIONS LTD., AT BEN-GURION UNIVERSITY, Beer Sheva (IL)

( * ) Notice: Subject to any disclaimer, the term of this patent is extended or adjusted under 35 U.S.C. 154(b) by 0 days.

(21) Appl. No.: 16/387,870

(22) Filed: Apr. 18, 2019

(65) Prior Publication Data

US 2019/0248836 A1 Aug. 15, 2019

Related U.S. Application Data

(63) Continuation-in-part of application No. PCT/IL2017/051155, filed on Oct. 19, 2017.

(60) Provisional application No. 62/410,429, filed on Oct. 20, 2016.

(51) Int. Cl.
| | |
|---|---|
| *A61K 31/404* | (2006.01) |
| *C07K 7/06* | (2006.01) |
| *A61P 31/04* | (2006.01) |
| *C07D 209/12* | (2006.01) |
| *A61P 31/08* | (2006.01) |
| *A61P 31/06* | (2006.01) |
| *C07D 209/20* | (2006.01) |
| *C07D 311/58* | (2006.01) |
| *C07C 251/76* | (2006.01) |
| *C07D 487/04* | (2006.01) |
| *C07D 209/42* | (2006.01) |
| *C07D 417/04* | (2006.01) |
| *C07D 209/14* | (2006.01) |
| *C07D 405/12* | (2006.01) |
| *A61K 47/50* | (2017.01) |
| *C07K 7/08* | (2006.01) |

(52) U.S. Cl.
CPC .............. *C07K 7/06* (2013.01); *A61K 31/404* (2013.01); *A61K 47/50* (2017.08); *A61P 31/04* (2018.01); *A61P 31/06* (2018.01); *A61P 31/08* (2018.01); *C07C 251/76* (2013.01); *C07D 209/12* (2013.01); *C07D 209/14* (2013.01); *C07D 209/20* (2013.01); *C07D 209/42* (2013.01); *C07D 311/58* (2013.01); *C07D 405/12* (2013.01); *C07D 417/04* (2013.01); *C07D 487/04* (2013.01); *C07K 7/08* (2013.01)

(58) Field of Classification Search
None
See application file for complete search history.

(56) References Cited

U.S. PATENT DOCUMENTS

| | | | | |
|---|---|---|---|---|
| 5,229,413 A | * | 7/1993 | Gray | ................... A61K 31/405 |
| | | | | 514/415 |
| 6,096,499 A | | 8/2000 | Kozlowski et al. | |
| 2014/0171432 A1 | * | 6/2014 | Kanouni | .............. C07D 401/14 |
| | | | | 514/234.5 |

FOREIGN PATENT DOCUMENTS

| | | |
|---|---|---|
| EP | 2366687 A2 | 9/2011 |
| WO | 1987006133 A1 | 10/1987 |
| WO | 2003072570 A1 | 9/2003 |
| WO | 2008154271 A1 | 12/2008 |

OTHER PUBLICATIONS

Grant & Hackh's Chemical Dictionary (5th Ed. 1987) at p. 148. (2).*
Akladios, Fady N. Design and synthesis of novel inhibitors of human kynurenine aminotransferase-I. Bioorganic & Medicinal Chemistry Letters. 22 (2012) 1579-1581.*
Kaessler, Andre. Indole carboxamides inhibit bovine testes hyaluronidase at pH 7.0 and indole acetamides activate the enzyme at pH 3.5 by different mechanisms. Journal of Enzyme Inhibition and Medicinal Chemistry. 23(5), 2008, 719-727.*
Akladios FN et al. Design and synthesis of novel inhibitors of human kynurenine aminotransferase-I. Bioorganic & medicinal chemistry letters (Feb. 15, 2012); 22(4), pp. 1579-1581.
Baqi Y et al. Improved synthesis of 4-/6-substituted 2-carboxy-1 H-indole-3-propionic acid derivatives and structure—activity relationships as GPR17 agonists. Med. Chem. Commun. 2014 (published on Nov. 22, 2013); 5(1), pp. 86-92.
CAS Registry No. 261363-54-6; CA Index Name: 1H-Indole-3-propanoic acid, 2- (ethoxycarbonyl)-5-nitro-; Entered STN: Apr. 7, 2000.
Girisha M et al. Synthesis and biological activities of indole-3-propionic acids. Indian Journal of Heterocyclic Chemistry (Jan. 1, 2008);17(3), pp. 275-276.
CAS Registry No. 304665-55-2; CA Index Name: Benzenamine, 4-methyl-N-[(2- methyl-1H-indol-3-yl) methylene]-3-nitro-; Entered STN: Nov. 28, 2000.
CAS Registry No. 363591-25-7 (CA Index Name: 1H-Indole-2-carboxylic acid, 3-[2- (acetylamino)ethyl]-5-methoxy-7-nitro-), entered STN: Oct. 21, 2001. & WO 2008/06818.
Martel S et al. Large, chemically diverse dataset of logP measurements for benchmarking studies. European Journal of Pharmaceutical Sciences (Jan. 23, 2013); 48(1), pp. 21-29.
CAS Registry No. 459420-18-9; CA Index Name: 1H-Indole, 3-[4-(3-nitrophenyl)-2- thiazolyl]-; Entered STN: Oct. 7, 2002.

(Continued)

*Primary Examiner* — Samantha L Shterengarts

(74) *Attorney, Agent, or Firm* — The Roy Gross Law Firm, LLC; Roy Gross

(57) ABSTRACT

Disclosed herein are compounds that are selective DNA primase and/or gyrase inhibitors. Further disclosed are pharmaceutical compositions comprising these compounds, and the uses of these compounds for treating disorders associated with microbial infections.

17 Claims, 28 Drawing Sheets

(2 of 28 Drawing Sheet(s) Filed in Color)

Specification includes a Sequence Listing.

(56) References Cited

OTHER PUBLICATIONS

Di Fabio R et al. Substituted indole-2-carboxylates as in vivo potent antagonists acting as the strychnine-insensitive glycine binding site. Journal of medicinal chemistry (Mar. 14, 1997); 40(6), pp. 841-850.
Feng L et al. The effect of PLC-gamma2 inhibitors on the growth of human tumour cells. European journal of medicinal chemistry (Aug. 31, 2012); 54, pp. 463-469.
CAS Registry No. 1046760-52-4; CA Index Name: L-Tryptophan, N-[(4 nitrophenyl) methyl]; Entered STN: Sep. 5, 2008.
CAS Registry No. 883098-68-8; CA Index Name: 1H-Indole-2-carboxamide, N-1,3- benzodioxol-5-yl-7-nitro-; Entered STN: May 5, 2006.
Narayana B et al. Synthesis and studies on antimicrobial, antiinflammatory and antiproliferative activities of heterocycles derived from 4-/5-/6-/7-nitro/5-fluoro/chloro/ bromoindole-2-carbohydrazides. Indian Journal of Chemistry (Dec. 2009); 48B, pp. 1794-1805.
Matsuda K et al. Growth inhibition of Pseudomonas solanacearum by substituted 3- indolepropionic acids and related compounds. Bioscience, biotechnology, and biochemistry (Jan. 1, 1993); 57(10), pp. 1766-1767.
Tomasic T et al. Discovery of 4, 5, 6, 7-tetrahydrobenzo [1,2-d] thiazoles as novel DNA gyrase inhibitors targeting the ATP-binding site. Journal of medicinal chemistry (Jul. 8, 2015); 58(14), pp. 5501-5521.
Oyamada Y et al. Mechanism of Inhibition of DNA Gyrase by ES-1273, a Novel DNA Gyrase Inhibitor. Microbiology and immunology (Oct. 1, 2007); 51(10), pp. 977-984.
Jeankumar VU et al. Gyrase ATPase Domain as an Antitubercular Drug Discovery Platform: Structure-Based Design and Lead Optimization of Nitrothiazolyl Carboxamide Analogues. ChemMedChem (Aug. 1, 2014); 9(8), pp. 1850-1859.
Chen GY et al. Application of Fragment-Based Drug Discovery against DNA Gyrase B. ChemPlusChem (Aug. 1, 2015); 80(8), pp. 1250-1254.
Reck F et al. Novel N-linked aminopiperidine inhibitors of bacterial topoisomerase type II: broad-spectrum antibacterial agents with reduced hERG activity. Journal of medicinal chemistry (Oct. 27, 2011); 54(22), pp. 7834-7847.
Hegde VR et al. Two new bacterial DNA primase inhibitors from the plant Polygonum cuspidatum. Bioorganic & medicinal chemistry letters (May 3, 2004); 14(9), pp. 2275-2277.
Ilic S et al. Identification of DNA primase inhibitors via a combined fragment-based and virtual screening. Scientific reports (published online Nov. 2, 2016); 6:36322.

Jukic M et al. Linker-switch approach towards new ATP binding site inhibitors of DNA gyrase B. European journal of medicinal chemistry (Jan. 5, 2017); 125, pp. 500-514.
Jakopin Z et al. Discovery of substituted oxadiazoles as a novel scaffold for DNA gyrase inhibitors. European Journal of Medicinal Chemistry (Apr. 21, 2017); 130, pp. 171-184.
Cotman AE et al. Design, Synthesis, and Evaluation of Novel Tyrosine-Based DNA Gyrase B Inhibitors. Archiv der Pharmazie (Aug. 1, 2017); 350(8).
Lacriola CJ et al. Inhibition of DNA replication in *Staphylococcus aureus* by tegaserod. The Journal of Antibiotics (May 31, 2017); 70, pp. 918-920.
Meenakshi Singh et al, "Dual acting small-Molecule inhibitors targeting Mycobacterial DNA replication", Journal of Medicinal Chemistry, 2020.
Esteban, J. & Garcia-Coca, M. *Mycobacterium* Biofilms. Front Microbiol 8, 2651 (2017).
Singh, M., Tam, B. & Akabayov, B. NMR-Fragment Based Virtual Screening: A Brief Overview. Molecules 23, Feb. 2018; 23(2): 233.
Chilingaryan, Z. et al. Fragment-Based Discovery of Inhibitors of the Bacterial DnaGSSB Interaction. Antibiotics (Basel), Mar. 2018; 7(1): 14.
Akladios, F.N. et al. Design and synthesis of novel inhibitors of human kynurenine aminotransferase-I. Bioorg Med Chem Lett. Feb. 15, 2012;22(4):1579-81.
Bie, J. et al. Discovery of novel indole derivatives as allosteric inhibitors of fructose-1,6-bisphosphatase. Eur J Med Chem 90, 394-405 (2015).
Gengenbacher, M. & Kaufmann, S.H. *Mycobacterium tuberculosis*: success through dormancy. FFMS Microbiol Rev 36, 514-32 (2012).
Gorla, P. et al. MtrA Response Regulator Controls Cell Division and Cell Wall Metabolism and Affects Susceptibility of Mycobacteria to the First Line Antituberculosis Drugs. Front Microbiol 9, 2839 (2018).
Futaki, S. Membrane-permeable arginine-rich peptides and the translocation mechanisms. Adv Drug Deliv Rev 57, 547-58 (2005).
Lindgren, M., Hallbrink, M., Prochiantz, A. & Langel, U. Cell-penetrating peptides. Trends Pharmacol Sci 21, 99-103 (2000).
Wadia, J.S. & Dowdy, S.F. Transmembrane delivery of protein and peptide drugs by TAT-mediated transduction in the treatment of cancer. Adv Drug Deliv Rev 57, 579-96 (2005).
Sparr, C. et al. Improved efficacy of fosmidomycin against *Plasmodium* and *Mycobacterium* species by combination with the cell-penetrating peptide octaarginine. Antimicrob Agents Chemother 57, 4689-98 (2013).
CAS Registry No. 681844-44-0; CA Index Name: Benzamide, 3-methyl-N-[2-(2- methyl-1H-indol-3-yl)ethyl]-4-nitro-; Entered STN: May 14, 2004.

* cited by examiner

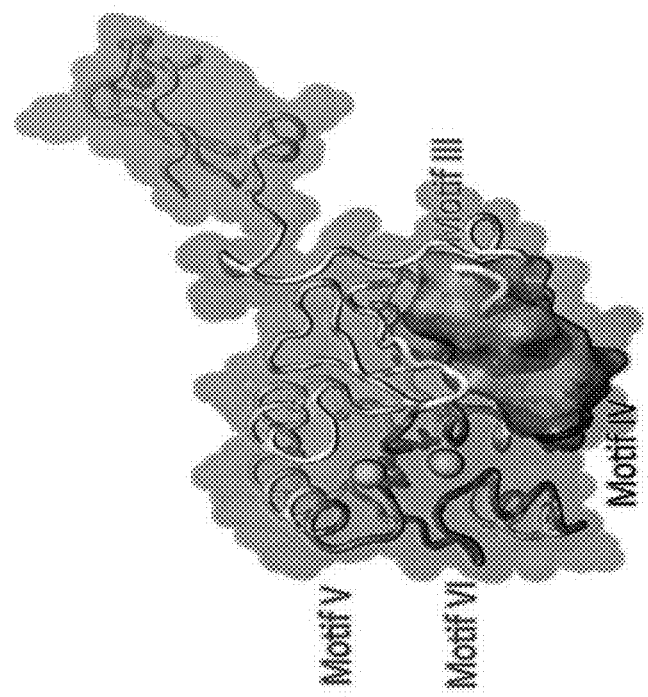
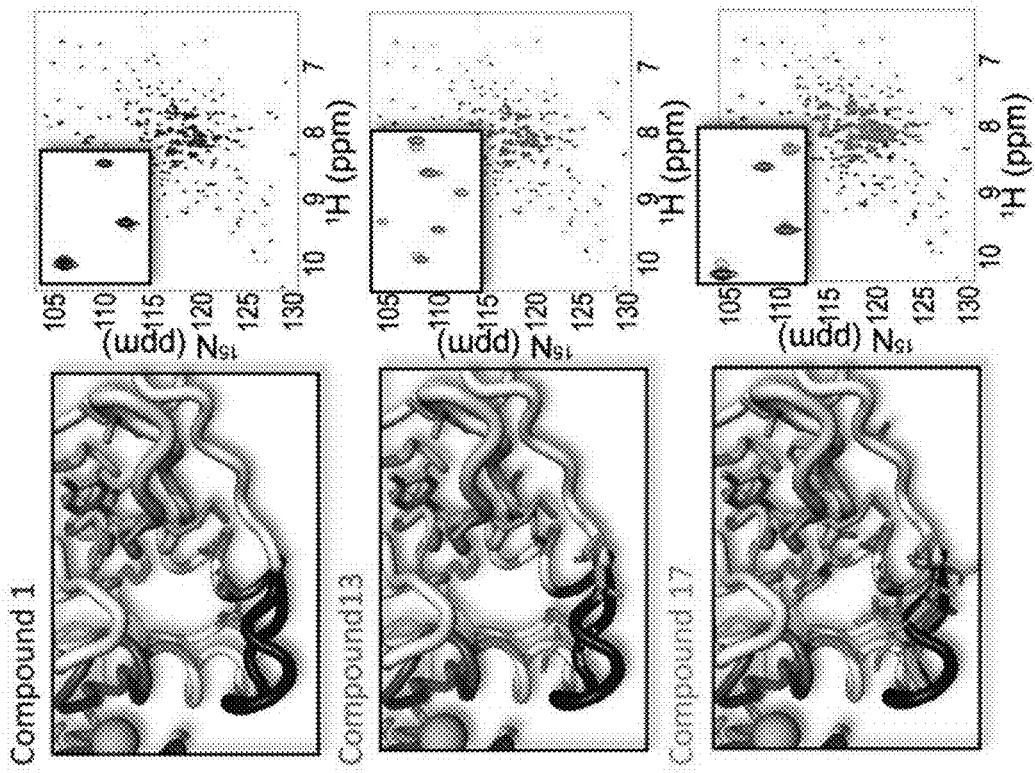
Figure 7A
Figure 7B

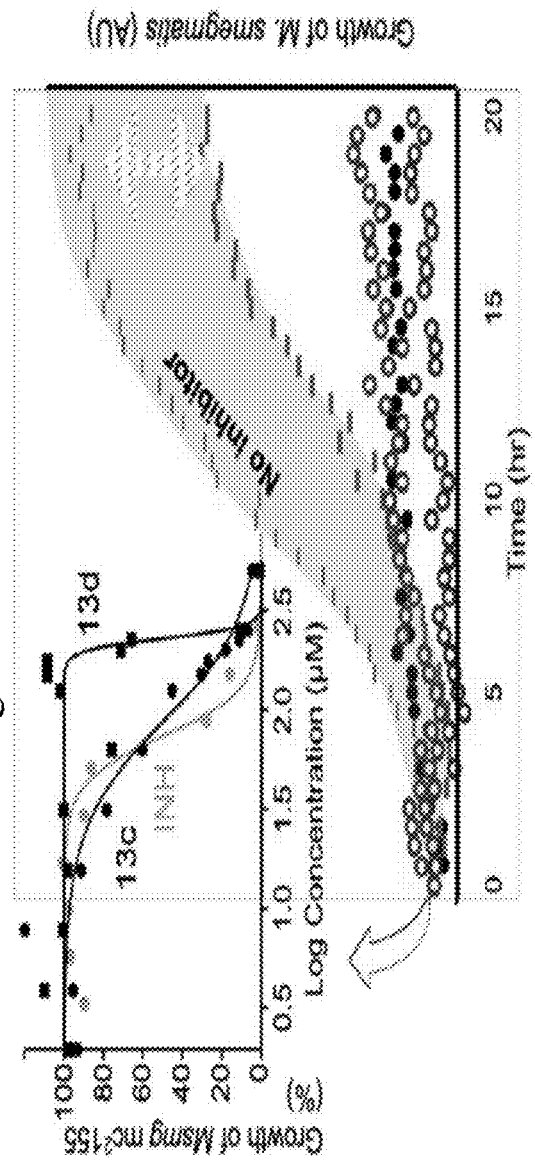
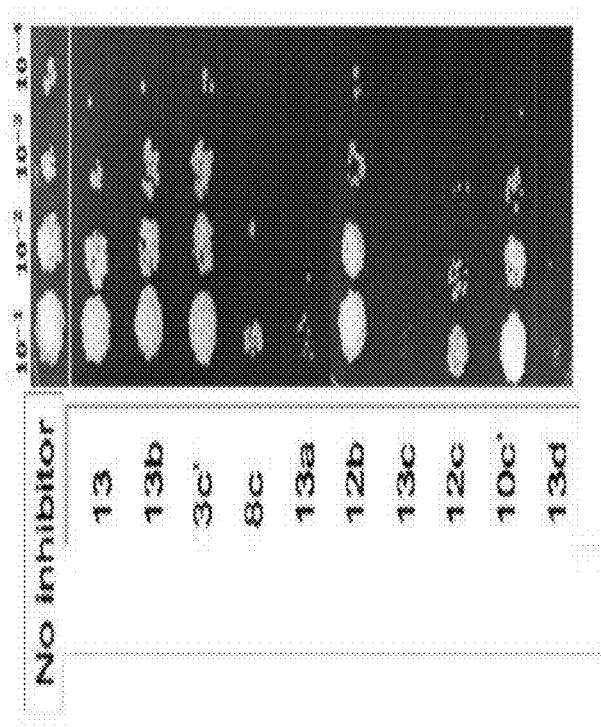
Figure 14A
Figure 14B

13C

13D

SEQUENCE LISTING

```
<160> NUMBER OF SEQ ID NOS: 4

<210> SEQ ID NO 1
<211> LENGTH: 82
<212> TYPE: PRT
<213> ORGANISM: Aquifex aeolicus

<400> SEQUENCE: 1

Gly Phe Ala Ile Leu Val Glu Gly Tyr Phe Asp Leu Leu Arg Leu Phe
1               5                   10                  15

Ser Ala Leu Thr Gln Asn Gln Ala Asn Leu Leu Ser Lys Phe Thr Lys
            20                  25                  30

Lys Val Tyr Ile Leu Tyr Asp Gly Asp Asp Ala Gly Arg Lys Ala Met
        35                  40                  45

Lys Ser Ala Ile Pro Leu Leu Leu Ser Ala Gly Val Glu Val Tyr Pro
    50                  55                  60

Val Tyr Leu Pro Glu Gly Glu Gly Ile Arg Asn Val Val Ala Pro Leu
65                  70                  75                  80

Gly Thr

<210> SEQ ID NO 2
<211> LENGTH: 82
<212> TYPE: PRT
<213> ORGANISM: Staphylococcus aureus
```

```
<400> SEQUENCE: 2

Asp Glu Ile Val Leu Leu Glu Gly Phe Met Asp Val Ile Lys Ser Asp
1               5                   10                  15

Thr Ala Gly Leu Lys Asn Val Val Ala Thr Met Gly Thr Gln Leu Ser
            20                  25                  30

Asp Glu His Ile Thr Phe Ile Arg Lys Leu Thr Ser Asn Ile Thr Leu
        35                  40                  45

Met Phe Asp Gly Asp Phe Ala Gly Ser Glu Ala Thr Leu Lys Thr Gly
    50                  55                  60

Gln His Leu Leu Gln Gln Gly Leu Asn Val Phe Val Ile Gln Leu Pro
65                  70                  75                  80

Ser Gly

<210> SEQ ID NO 3
<211> LENGTH: 89
<212> TYPE: PRT
<213> ORGANISM: Bacteriophage T7

<400> SEQUENCE: 3

Lys Lys Ile Val Val Thr Glu Gly Glu Ile Asp Met Leu Thr Val Met
1               5                   10                  15

Glu Leu Gln Asp Cys Lys Tyr Pro Val Val Ser Leu Gly His Gly Ala
            20                  25                  30

Ser Ala Ala Lys Lys Thr Cys Ala Ala Asn Tyr Glu Tyr Phe Asp Gln
        35                  40                  45

Phe Arg Glu Gln Ile Ile Leu Met Phe Asp Met Asp Glu Ala Gly Arg
    50                  55                  60

Lys Ala Val Glu Glu Ala Ala Gln Val Leu Pro Ala Gly Lys Val Arg
65                  70                  75                  80

Val Ala Val Leu Pro Cys Lys Asp Ala
                85

<210> SEQ ID NO 4
<211> LENGTH: 115
<212> TYPE: PRT
<213> ORGANISM: Mycobacterium tuberculosis

<400> SEQUENCE: 4

Ser Glu Leu Tyr Val Val Glu Gly Asp Ser Ala Gly Gly Ser Ala Lys
1               5                   10                  15

Ser Gly Arg Asp Ser Met Phe Gln Ala Ile Leu Pro Leu Arg Gly Lys
            20                  25                  30

Ile Ile Asn Val Glu Lys Ala Arg Ile Asp Arg Val Leu Lys Asn Thr
        35                  40                  45

Glu Val Gln Ala Ile Ile Thr Ala Leu Gly Thr Gly Ile His Asp Glu
    50                  55                  60

Phe Asp Ile Gly Lys Leu Arg Tyr His Lys Ile Val Leu Met Ala Asp
65                  70                  75                  80

Ala Asp Val Asp Gly Gln His Ile Ser Thr Leu Leu Leu Thr Leu Leu
                85                  90                  95

Phe Arg Phe Met Arg Pro Leu Ile Glu Asn Gly His Val Phe Leu Ala
                100                 105                 110

Gln Pro Pro
        115
```

DNA PRIMASE AND GYRASE INHIBITORS

CROSS-REFERENCE TO RELATED APPLICATIONS

This application is a Continuation In-Part (CIP) of PCT Patent Application No. PCT/IL2017/051155 having International filing date of Oct. 19, 2017, which claims the benefit of priority of U.S. Provisional Patent Application No. 62/410,429, filed on Oct. 20, 2016. The contents of the above applications are all incorporated by reference as if fully set forth herein in their entirety.

FIELD OF INVENTION

The present invention, in some embodiments thereof, relates to organic compounds and uses thereof in, for example, reducing or preventing growth of microorganisms.

BACKGROUND OF THE INVENTION

The complex process of identifying antibacterial compounds begins with the selection of potential targets, which must be essential, selective over human homologues, susceptible to drugs, and with a low propensity to develop rapid resistance. Although bacteria possess approximately 200 essential gene products, only a limited number of these have been exploited as drug targets. DNA replication, which qualifies as a novel drug target, is performed by the replisome, a multi enzyme complex that synthesizes DNA continuously on its leading strand and discontinuously on its lagging strand. For example, DNA primase, an essential component of the DNA replication machinery of every living cell, synthesizes short RNA primers that are used by DNA polymerase to form the "Okazaki fragments" on the lagging DNA strand. The inhibition of the primase, therefore, will halt DNA replication and, as a result, cell proliferation.

Prokaryotic primases share a conserved primary sequence and are structurally highly similar. In contrast, there are profound differences between human and bacterial DNA primases and gyrases.

Historically, the screening process for potential ligands has relied heavily on high throughput screening (HTS). The low effectiveness of HTS in identifying new antibacterial agents, however, led to the emergence of fragment-based screening as an alternative route for hit discovery in infectious disease research.

SUMMARY OF THE INVENTION

The present invention, in some embodiments thereof, relates to organic compounds and uses thereof in, for example, reducing or preventing growth of microorganisms.

According to an aspect of some embodiments of the present invention there is provided a compound represented by Formula I:

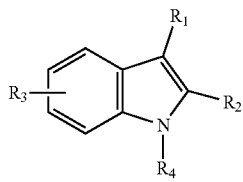

wherein:
$R_1$ and $R_2$, independently in each occurrence, comprise or are selected from the group consisting of hydrogen, alkyl, amine, amide, or carboxy; or $R_1$ and $R_2$ are joined together so as to form a fused ring system;

$R_3$ represents, independently in each occurrence, one to four groups selected from the group consisting of: an electron-withdrawing group, alkyl, cycloalkyl, aryl, heteroalicyclic, heteroaryl, alkoxy, hydroxy, thiohydroxy, thioalkoxy, aryloxy, thioaryloxy, amino, trihalomethyl, cyano, amide, carboxy, sulfonyl, sulfoxy, sulfinyl, sulfonamide, or a fused ring, substituted or non-substituted; and $R_4$ is selected from the group consisting of: hydrogen, alkyl, and alkaryl, substituted or non-substituted.

According to another aspect of some embodiments of the present invention, there is provided a compound represented by Formula II:

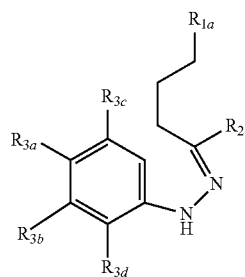

wherein:
$R_{1a}$ is selected from the group consisting of hydrogen, alkyl, amide, or carboxy;

up to three groups from $R_{3a-d}$ are substituents selected from the group consisting of: nitro, halo, and a fluorinated alkyl, wherein at least one group from $R_{3a}$ to $R_{3d}$ is hydrogen; and $R_2$ represents hydrogen or a substituent comprising or being selected from the group consisting of: alkyl, amide, or carboxy.

In some embodiments, there is provided a pharmaceutical composition comprising one or more of the disclosed compounds in some embodiment thereof, or a pharmaceutically acceptable salt thereof, and a pharmaceutically acceptable carrier.

In some embodiments, there is provided a method for treating a subject afflicted with microbial infection, comprising administering to said subject a pharmaceutically effective amount of one or more of the disclosed compounds.

In some embodiments, there is provided a method of inhibiting one or more enzymes selected from the group consisting of: DNA primase and gyrase, the method comprising contacting the DNA primase or the DNA gyrase with the disclosed compound(s) in an embodiment thereof, thereby inhibiting the DNA primase or the DNA gyrase, respectively.

In some embodiments, there is provided a method for killing bacteria or inhibiting bacteria from reproducing, the method comprising contacting the bacteria with the disclosed compound(s) in an embodiment thereof, thereby killing the bacteria or inhibiting the bacteria from reproducing.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description together with the drawings makes apparent to those skilled in the art how embodiments of the invention may be practiced.

In the drawings:

FIG. 1 is a scheme summarizing the fragment-based virtual screening procedure, as described in some embodiments of the present invention.

Figure 2A:
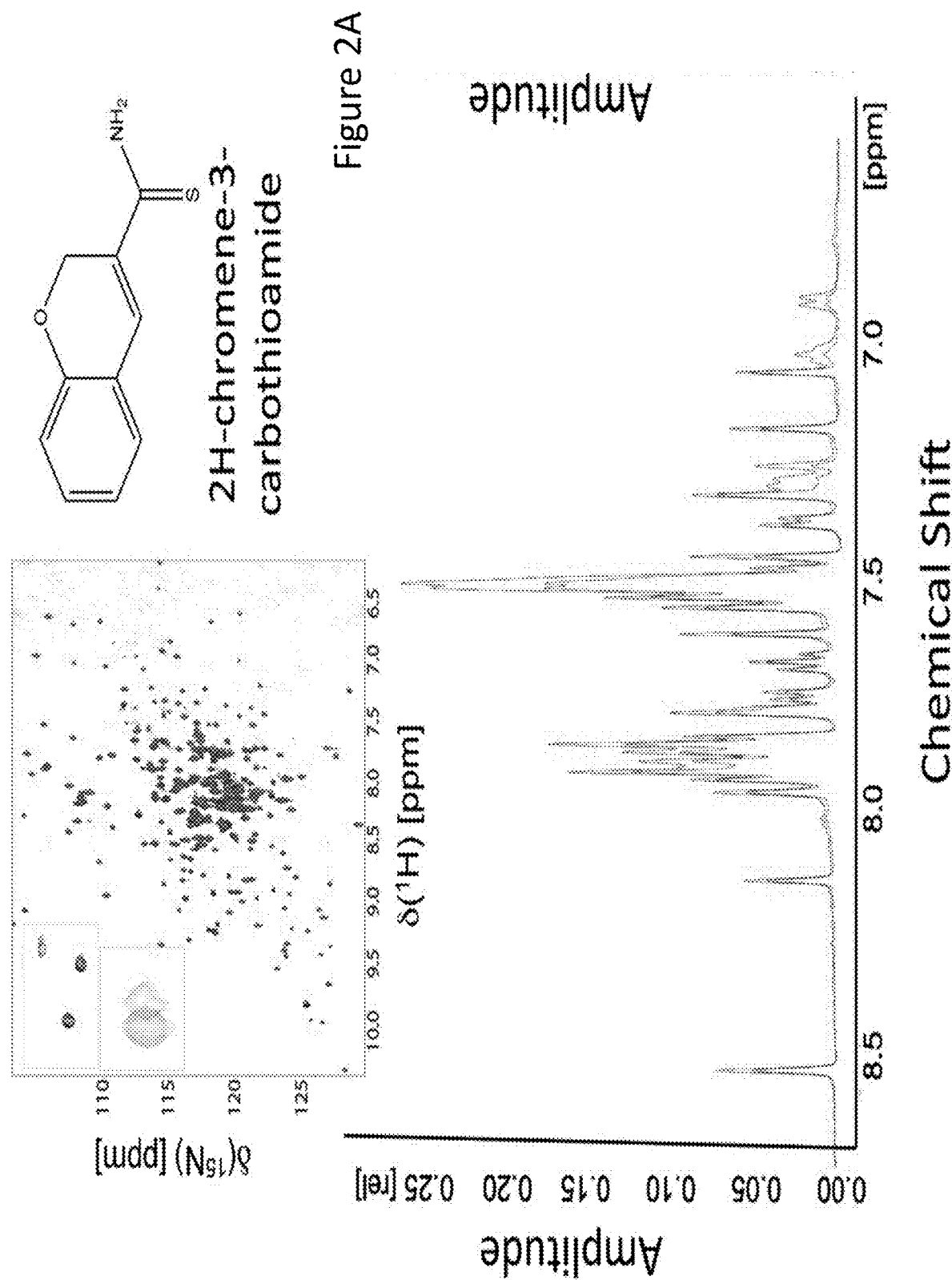
Figure 2B:
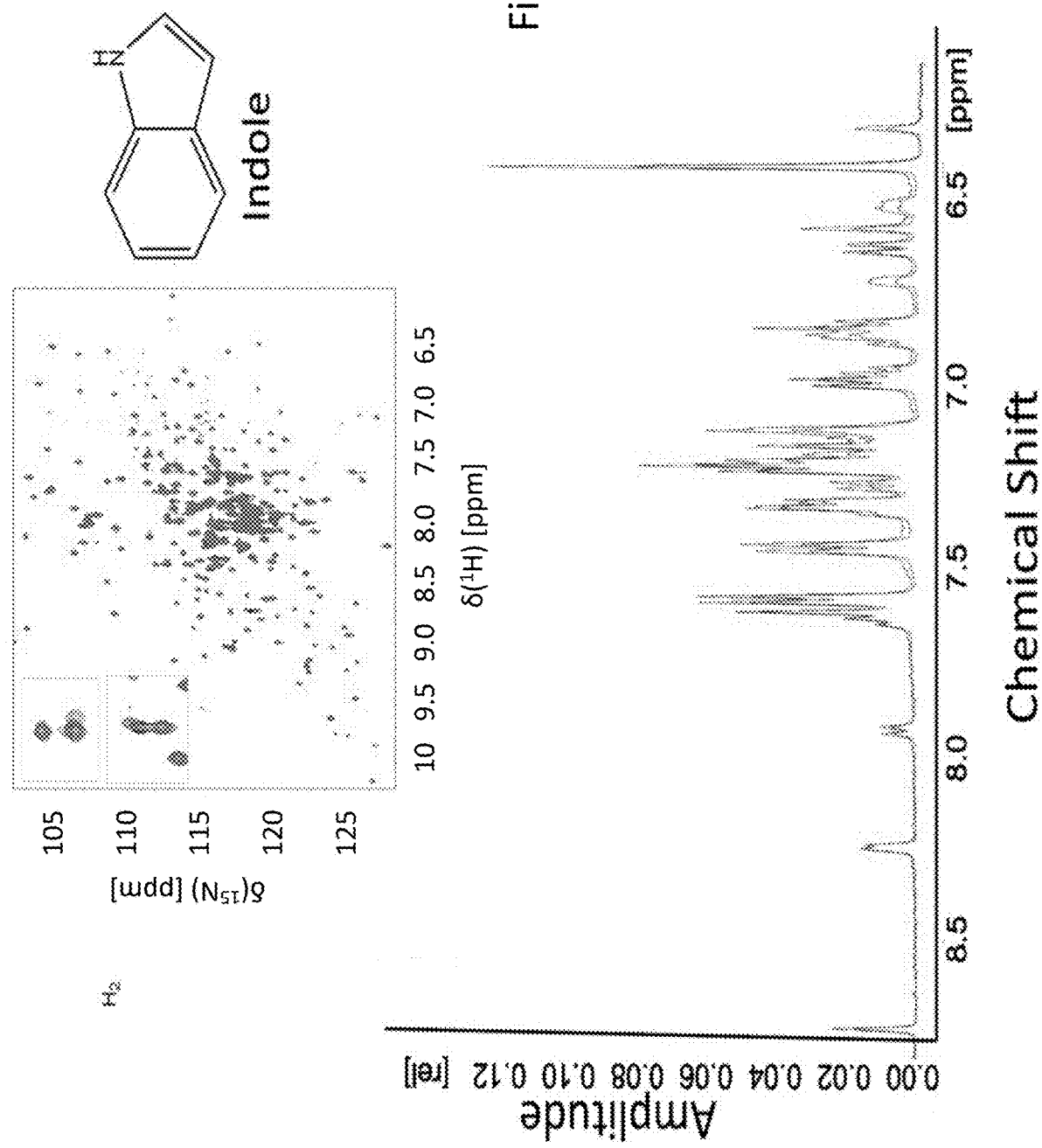

FIGS. 2A-B present 1D-NMR STD spectra of samples containing 10 scaffold compounds (including 2H-chromene-3-carbothioamide and indole, respectively) and T7 DNA primase. A decrease in the peak intensity after saturation indicates binding of the fragments to the primase. The change at a specific chemical shift value (x-axis) enables the identification of the molecule. Insets: 2D 1H, 15N HSQC spectra of 15N labeled T7 DNA primase in the presence of the fragments 2H-chromene-3-carbothioamide (FIG. 2A) and indole (FIG. 2B) found by STD spectroscopy. Chemical structures of 2H-chromene-3-carbothioamide and indole are further presented. STD: Saturation Transfer Difference; NMR: Nuclear Magnetic Resonance; HSQC: Heteronuclear Single Quantum Correlation.

Figure 3A:
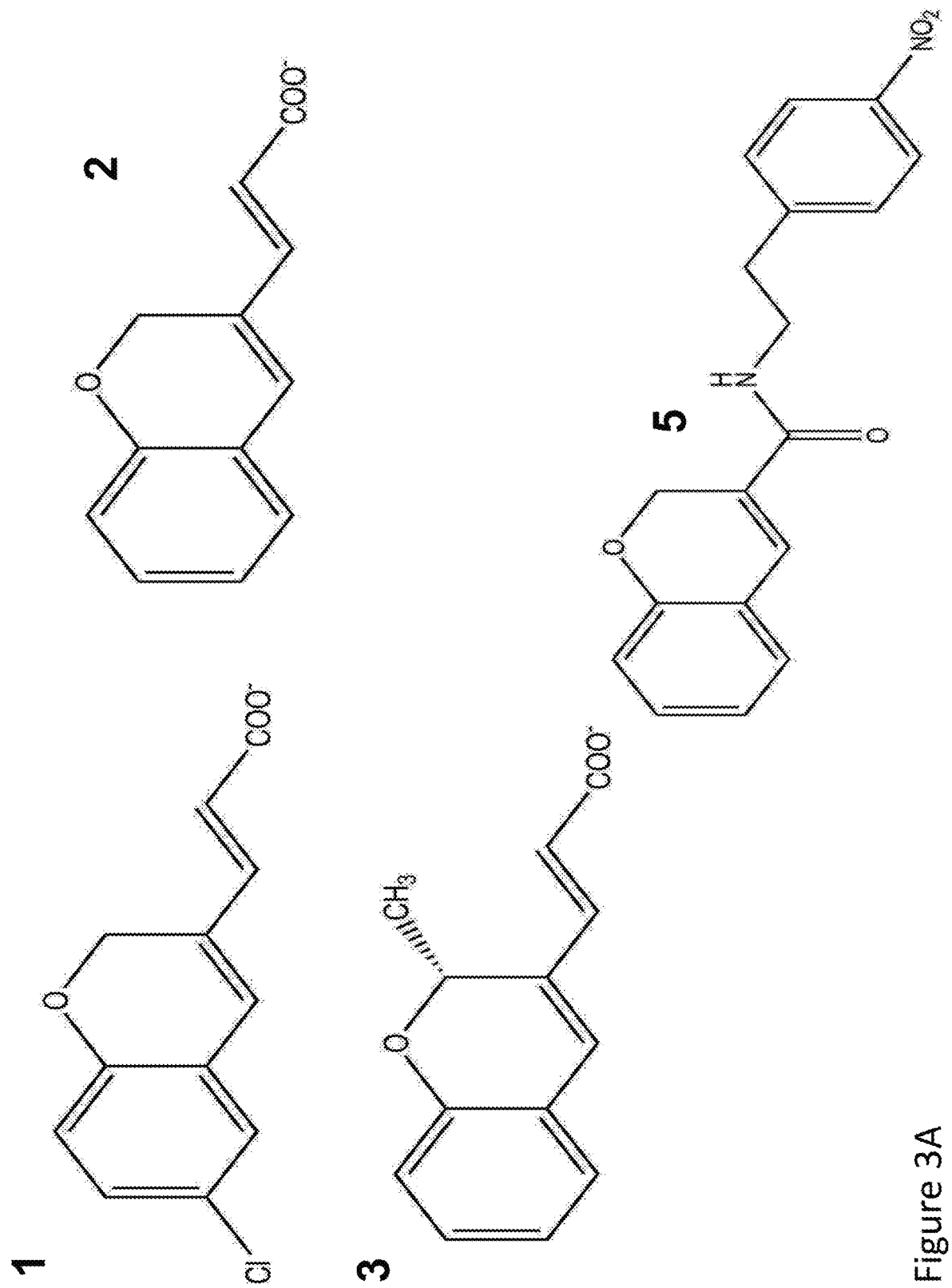
Figure 3B:
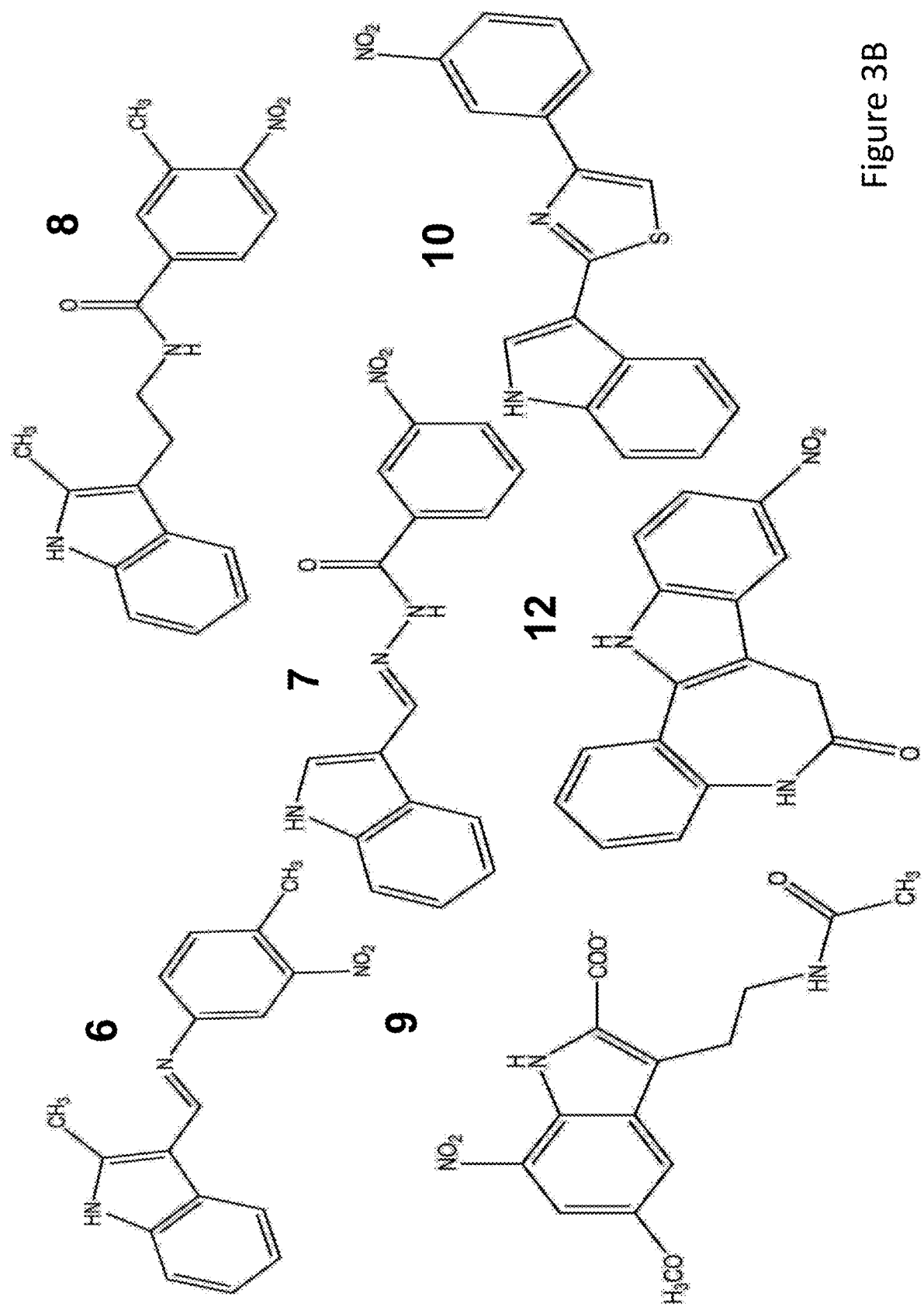
Figure 3C:
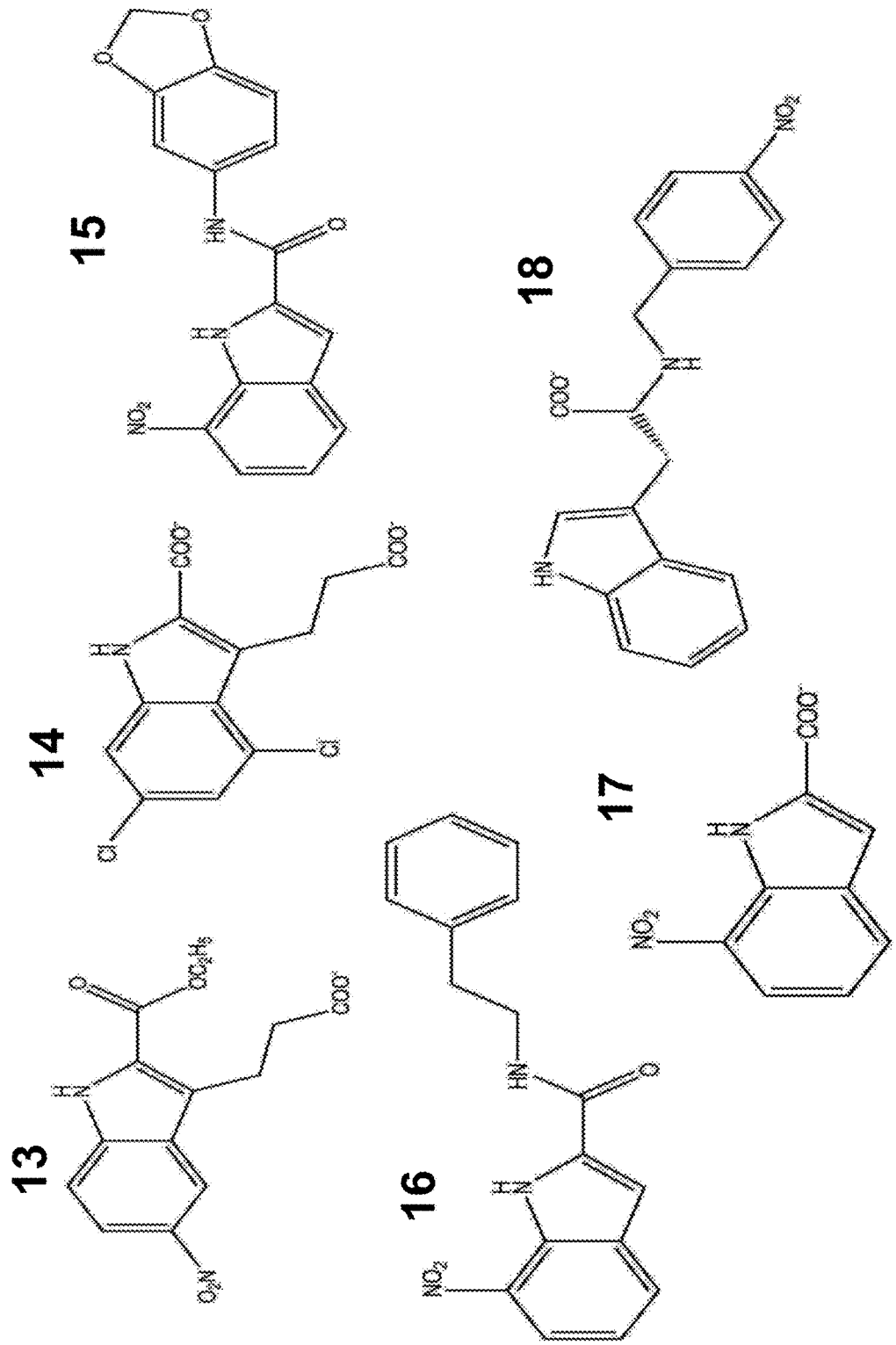

FIGS. 3A-C present chemical structures of 16 small molecules obtained by virtual filtration using the ZINC database and high-throughput docking using AutoDock. The two subsets are based on the scaffolds obtained by STD spectroscopy: 2H-chromene-3-carbothioamide (FIG. 3A) and indole (FIG. 3B-C).

Figure 4A:
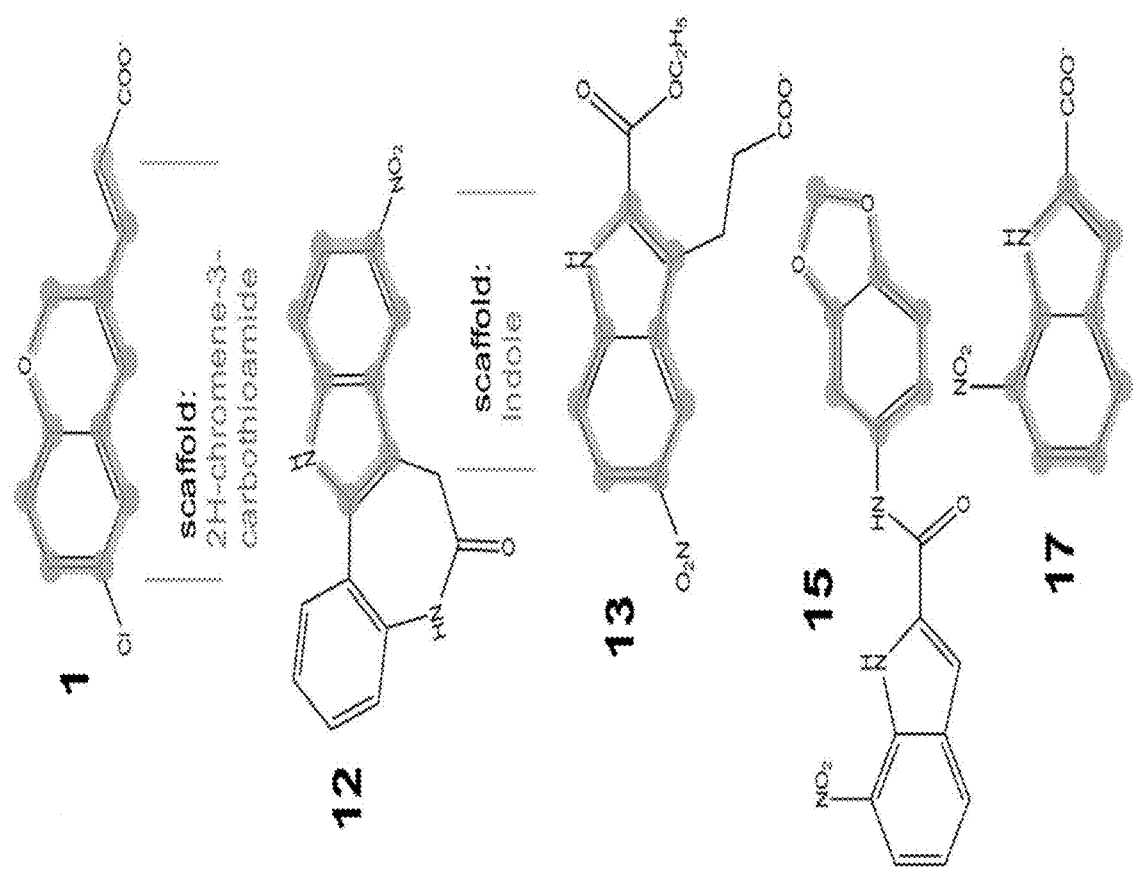
Figure 4B:
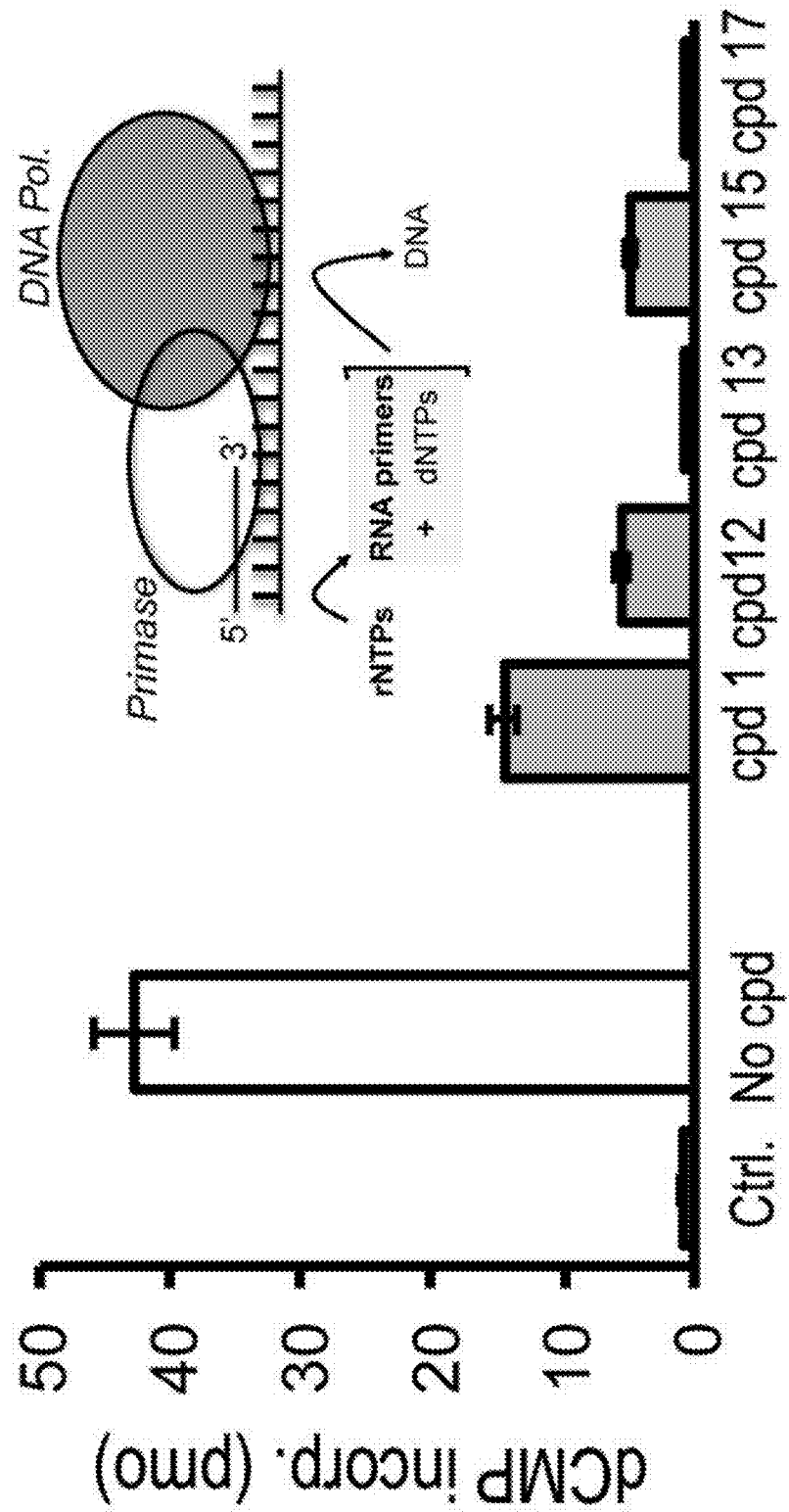

FIGS. 4A-B present small molecule inhibitors that contain fragments obtained by STD spectroscopy chemical structures of five small molecules obtained by virtual filtration using the ZINC database and high-throughput docking using AutoDock (the list of 16 compounds presented in FIGS. 3A-B) with the two subsets being based on the scaffolds obtained by STD spectroscopy: 2H-chromene-3-carbothioamide and indole (emphasized in thick grey) (FIG. 4A); bar graph showing the inhibitory effect of small molecules on bacteriophage T7 primase (FIG. 4B; the error bars were derived from three independent experiments), and a scheme showing template-directed pppAC ribonucleotide synthesis catalyzed by T7 DNA primase (inset in FIG. 4B).

Figure 5A:
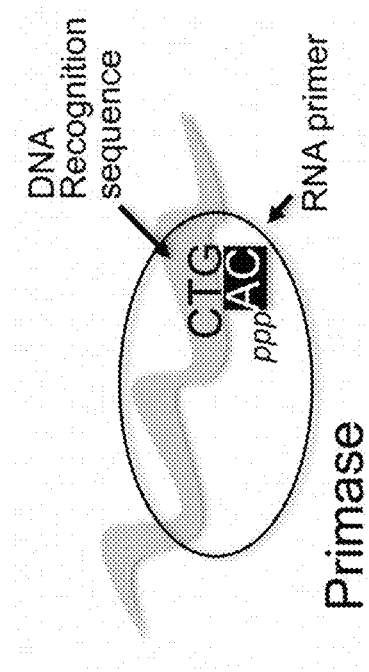
Figure 5B:
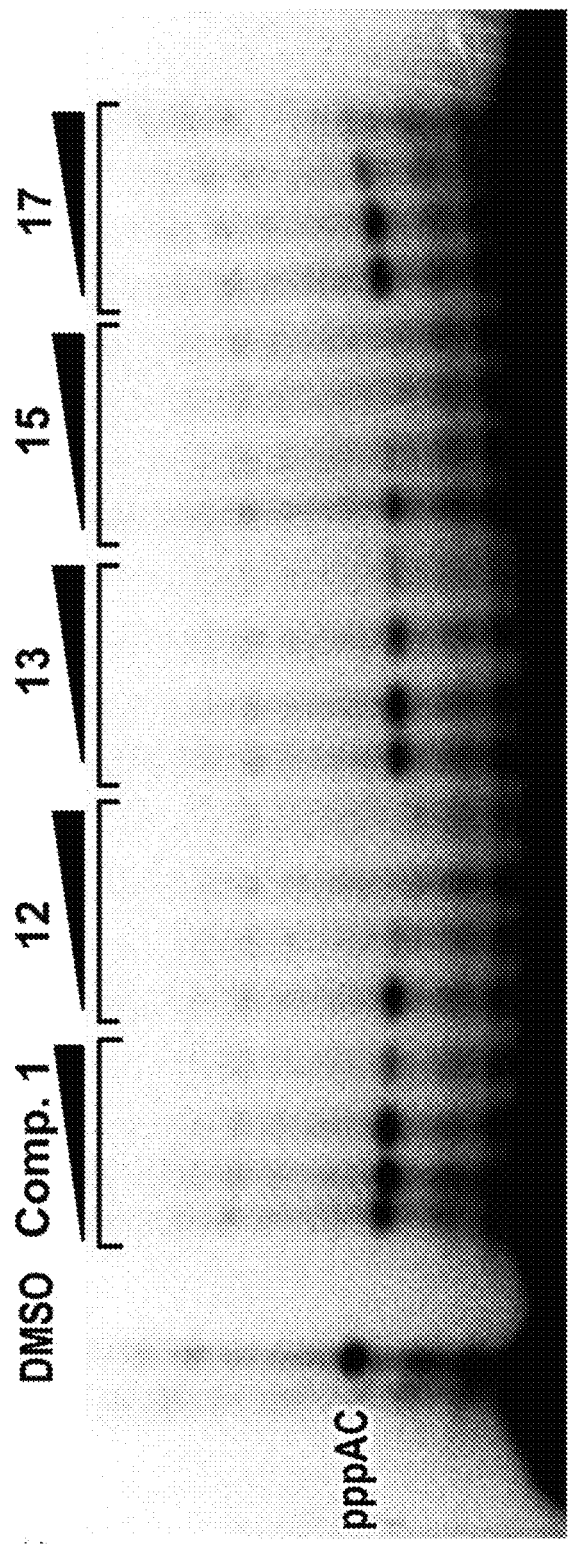
Figure 5C:
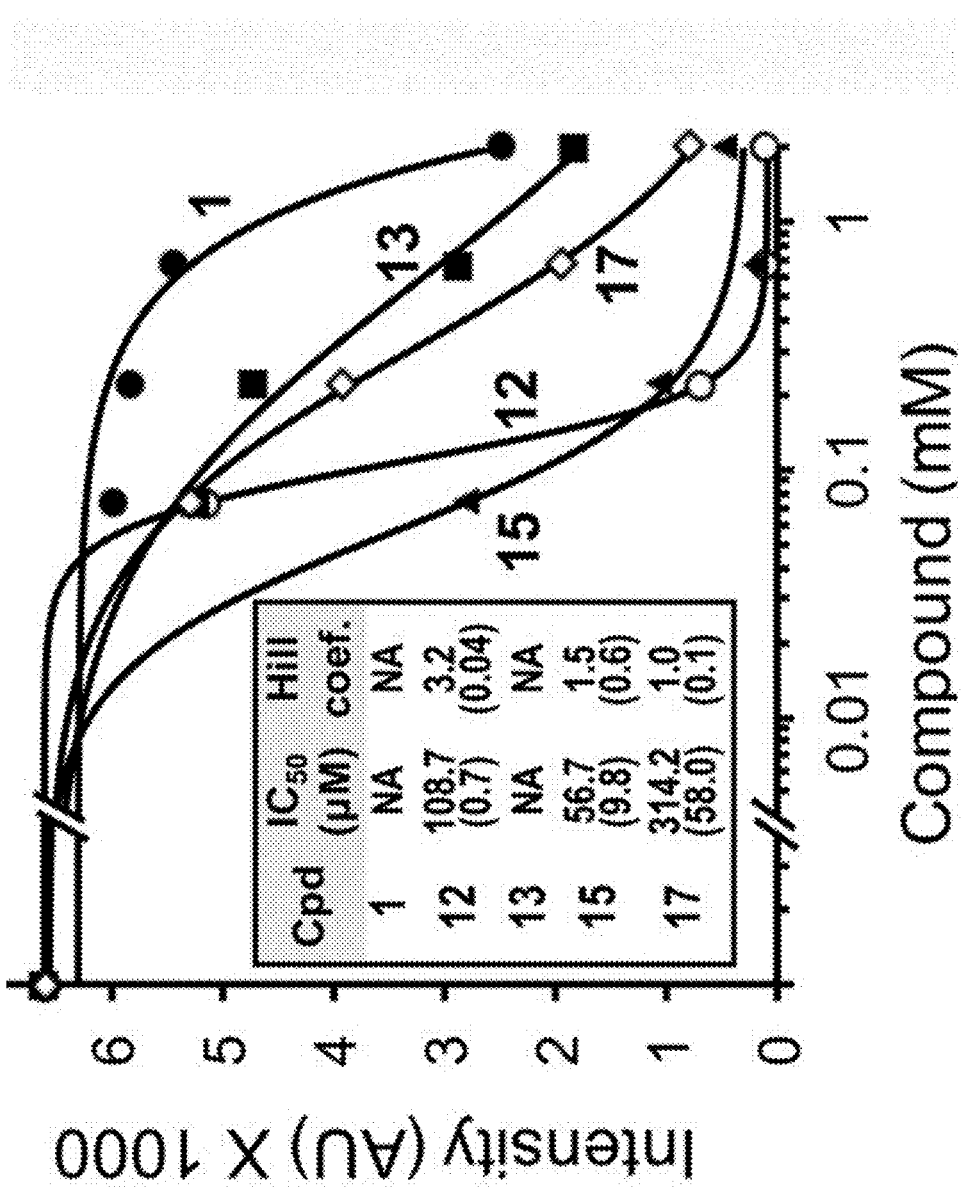

FIGS. 5A-C present a scheme summarizing the assay in which the DNA template containing the primase recognition site 5'-GTCA10-3' enables the synthesis of only diribonucleotides pppAC (FIG. 5A), and gel bands and quantification of gel bands representing the reaction products (5'-pppAC-3') (FIG. 5B and FIG. 5C, respectively).

Figure 6A:
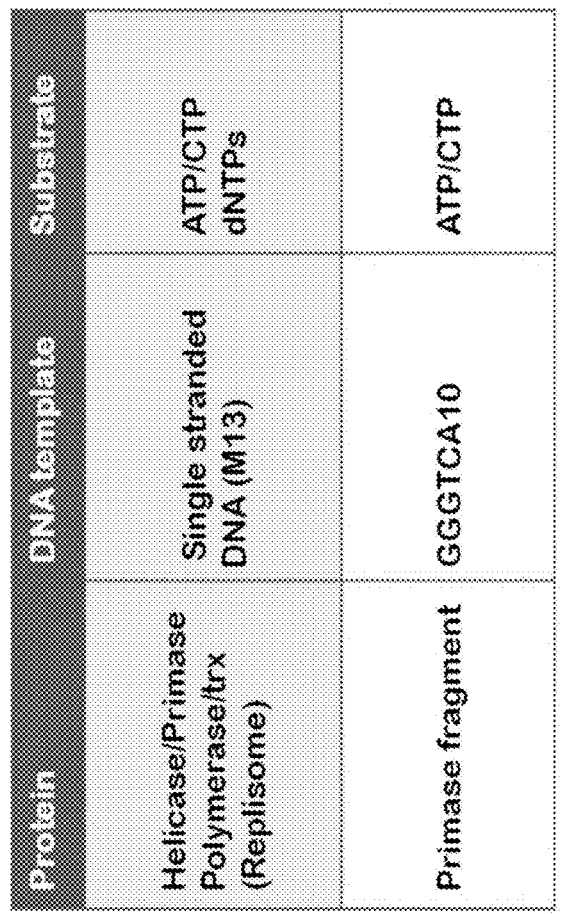
Figure 6B:
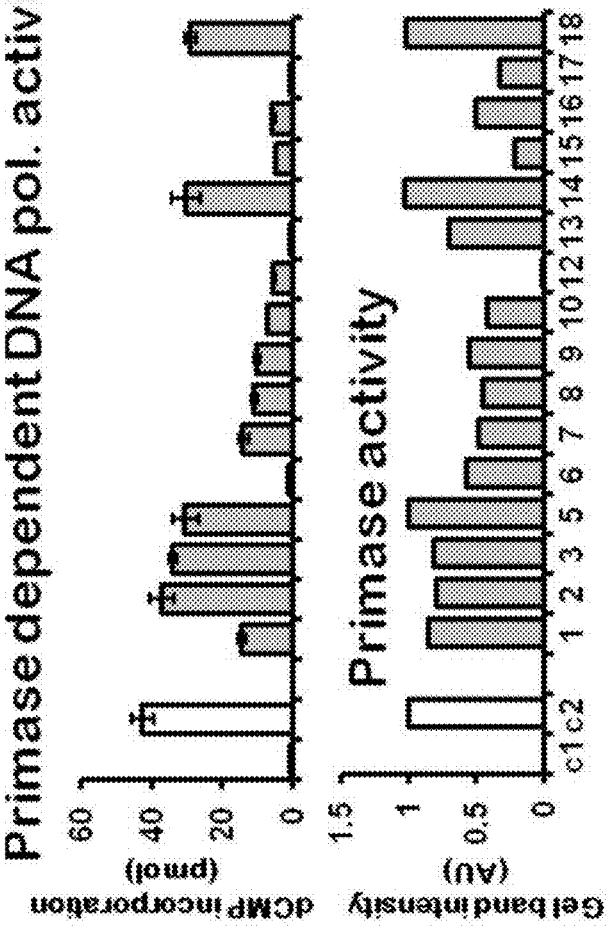

FIGS. 6A-B present the inhibitory effect of: small molecules on T7 DNA primase activity: the effect of small molecule inhibitors on primase-dependent DNA synthesis mediated by gp5/trx and gene 4 helicase (gp4A) (the Table in FIG. 6A), and the effect of small molecule inhibitors on oligonucleotide synthesis by DNA primase (FIG. 6B; the bar graphs show the primase dependent polymerase (pol) activity (the upper bar graph) vis-à-vis the primase activity (the lower bar graph)).

FIGS. 7A-B present binding-site of small-molecule inhibitors on T7 DNA primase: amino acid sequence chemical shift assignments indicating that small molecule binding occurs in the proximity of the main cleft of T7 DNA primase (binding site indicated in green) (FIG. 7A); The right panels in FIG. 7B present two-dimensional $^1$H-$^{15}$N HSQC spectrum of T7 DNA primase alone (spots) and in the presence of each small molecule inhibitor (upper panel, compound 1; middle panel, compound 13; lower panel, compound 17, as presented in FIGS. 3A-B)). The HSQC spectrum of primase changes in the wake of small molecule binding (similar peaks change upon titration of DNA (GGTCA) or ATP and CTP in the presence of magnesium added in a ratio molar concentration); The left panels in FIG. 7B presents amino acid residues that mediate the binding of each small molecule inhibitor as indicated in green.

Figure 8B:
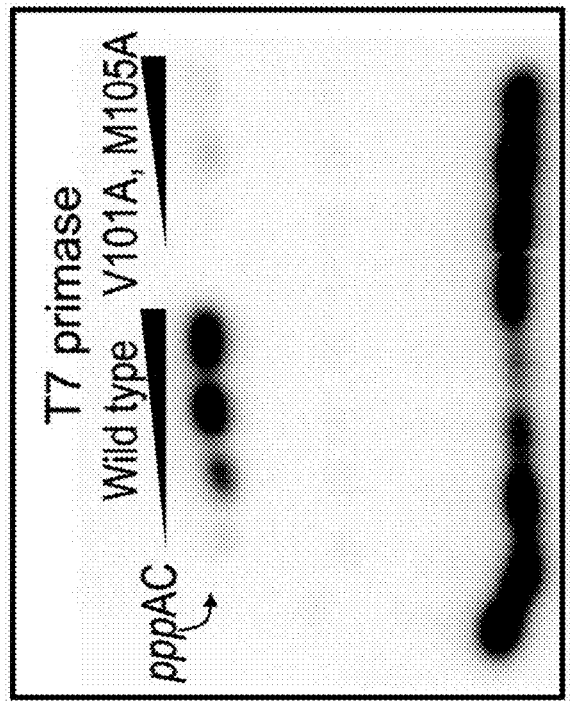
Figure 8A:
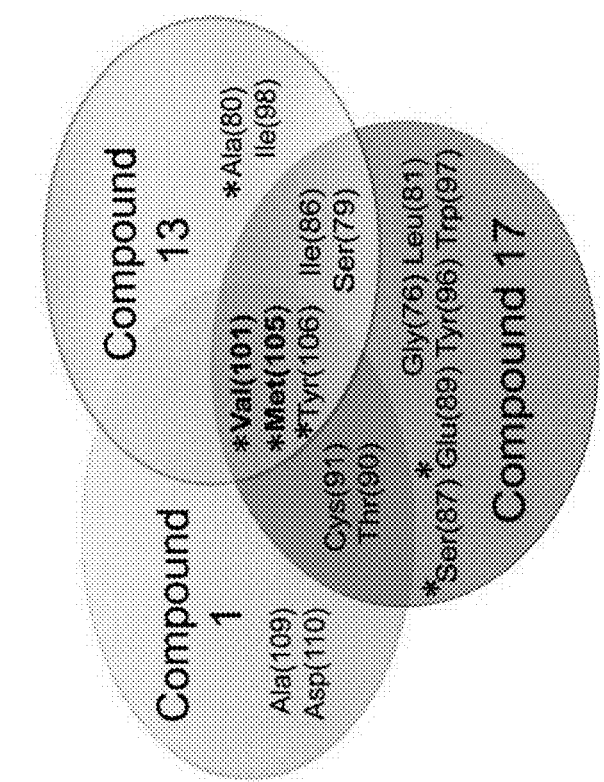
Figure 8C:
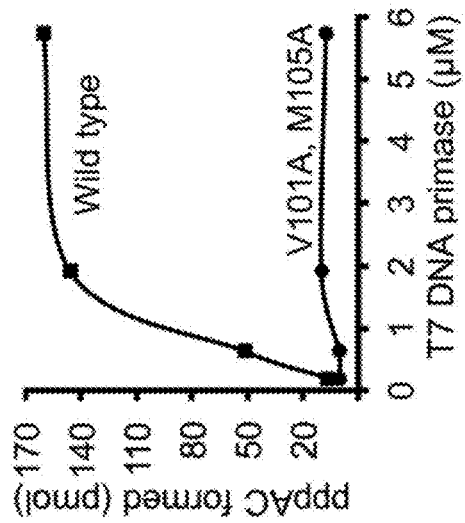

FIGS. 8A-C demonstrate the essentiality of amino acids that mediate the binding of small molecule inhibitors as presented in: a scheme showing the amino acid residues that mediate small molecule inhibitors at the active site of T7 DNA primase, showing that the three T7 primase inhibitors share the same binding site and are mediated via similar binding mechanisms (solvent accessible amino acid residues were calculated using Naccess and are marked in asterisk) (FIG. 8A), bands showing the substitutions of the central amino acids that were shown to mediate the binding of all the tested inhibitors and are solvent accessible (i.e., Val101 and Met105 were replaced with Ala) disrupted protein activity (FIG. 8B, the faint signal of pppAC remained for the reaction of the double mutant T7 DNA primase may be due to erroneous loading of the sample into the gel-reaction conditions were as in Figures. 4 and 5, except that the protein concentrations were 0.2, 0.6, 1.9, 5.8 µM, respectively), and in quantification of di-ribonucleotide synthesis by T7 DNA primase (FIG. 8C). The bands in the gels presented in FIG. 8B were analyzed using autoradiography.

Figure 9:
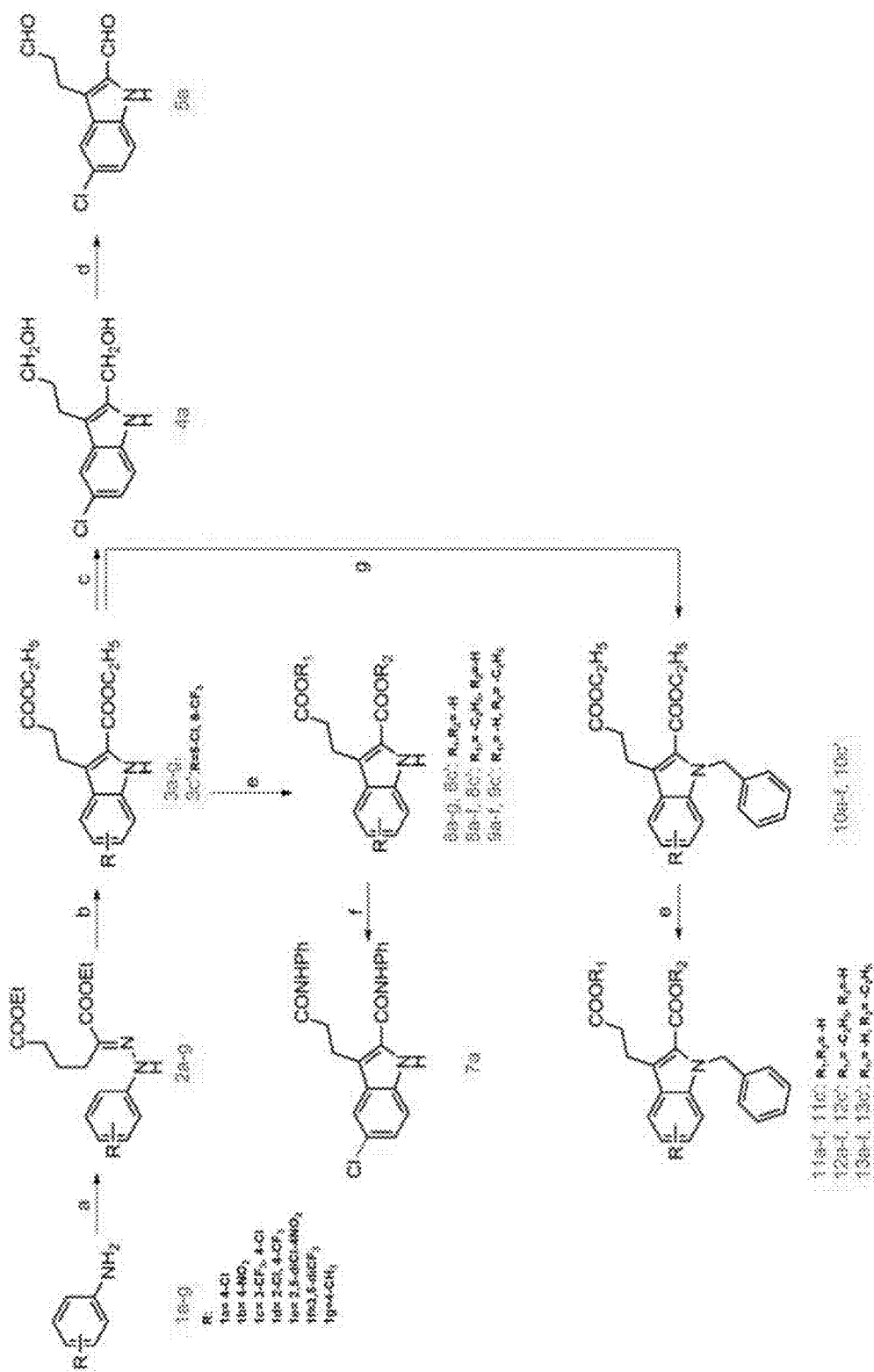

FIG. 9 presents a scheme showing the synthesis pathway to obtain indole derivatives, as detailed hereinbelow. Reagents and conditions: (a) i. HCl, NaNO2/H2O, 0° C., 1 h; ii. ethyl 2-oxocyclopentane carboxylate/4 M KOH, 0° C.; 1 h; iii. H2SO4/ethanol, 100° C., 3 h; (b) p-toluene sulfonic acid (PTSA), benzene, 110° C., 24 h; (c) LiAlH4, THF, H2SO4, rt, 2 h; (d) Pyridinium Chlorochromate (PCC), DCM, rt, 2-3 h; (e) 0.01 M NaOH/THF, rt, 18-24 h; (f) DCC, HOBt, dry DMF, aniline, rt, 24 h; (g) Cs$_2$CO$_3$, DMF, Benzyl bromide, KI, 60° C., 2 h.

Figure 10A:
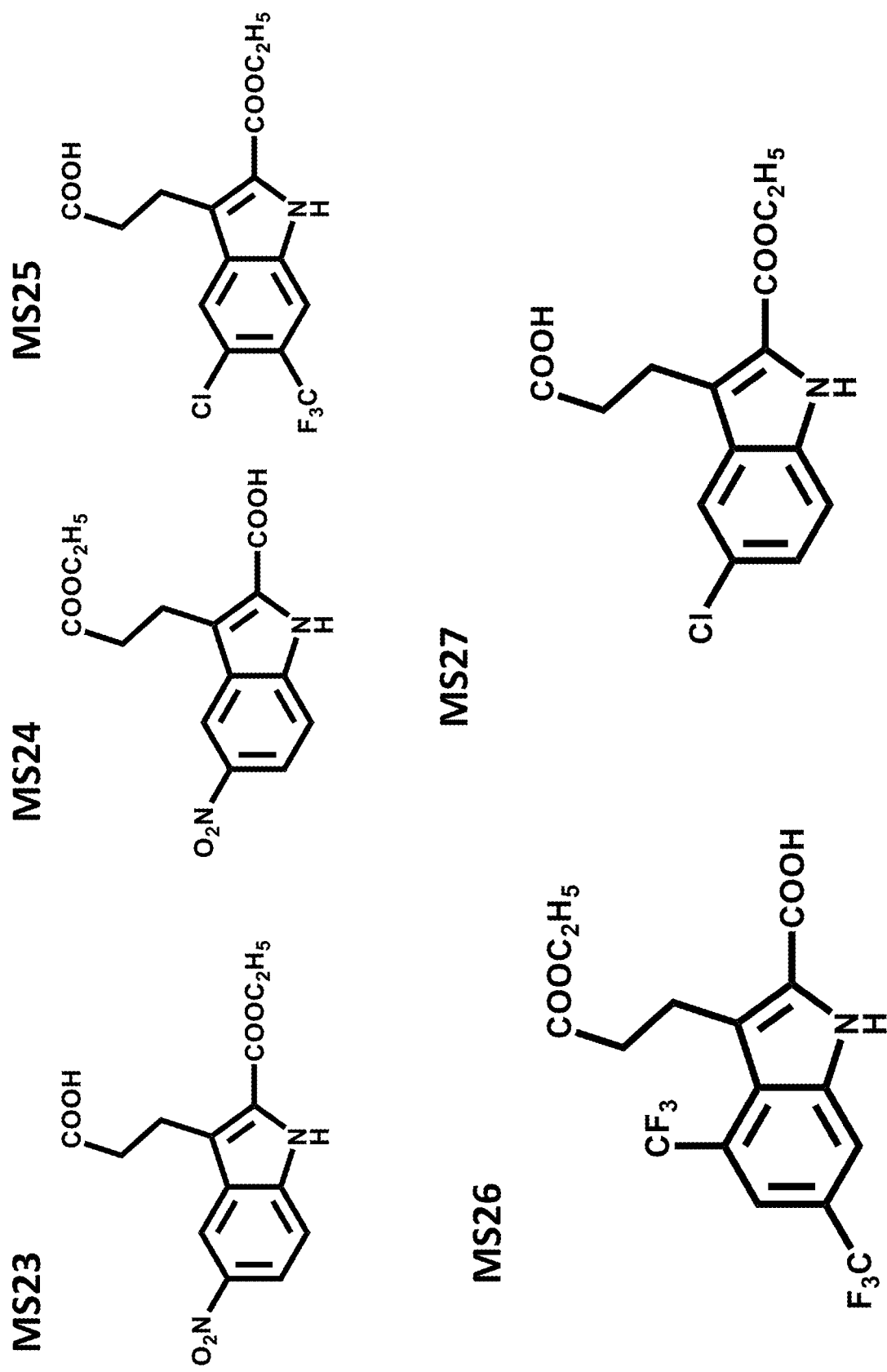
Figure 10B:
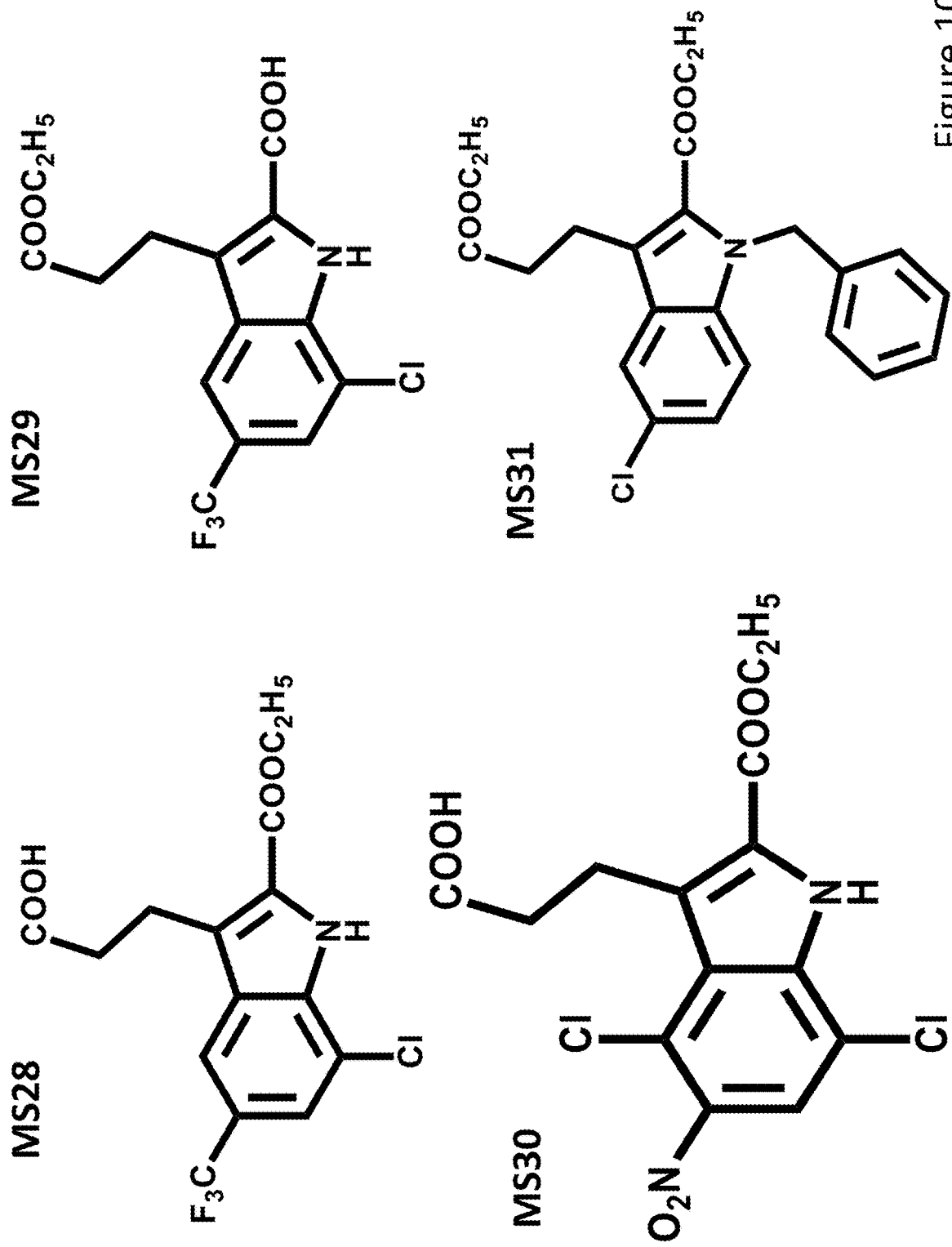
Figure 10C:
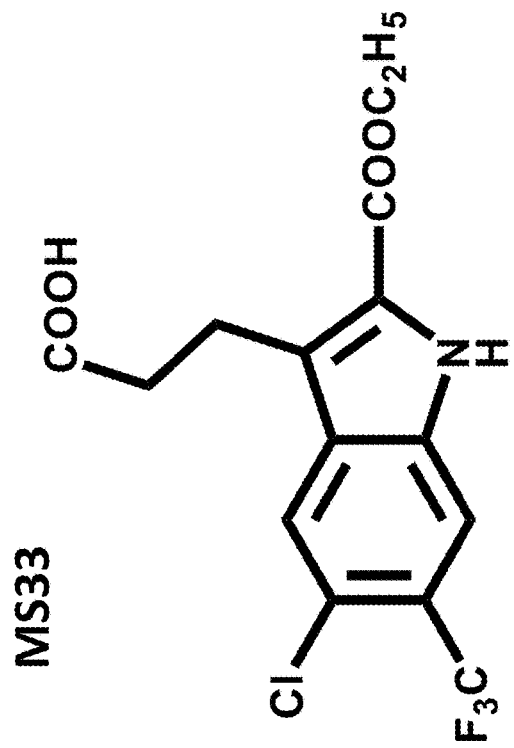
Figure 10C:
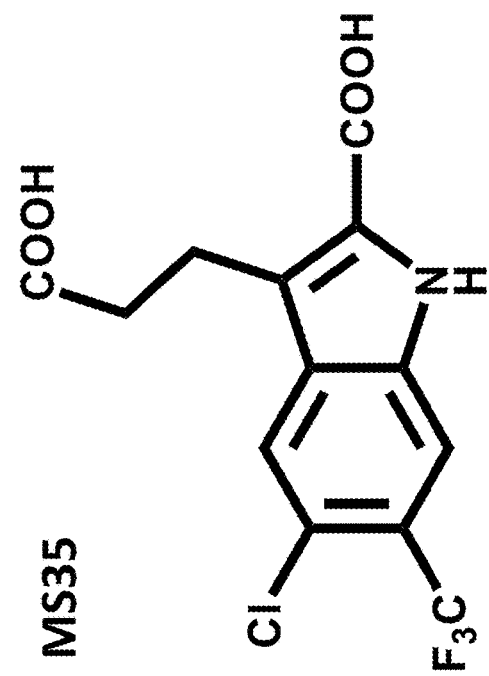
Figure 10C:
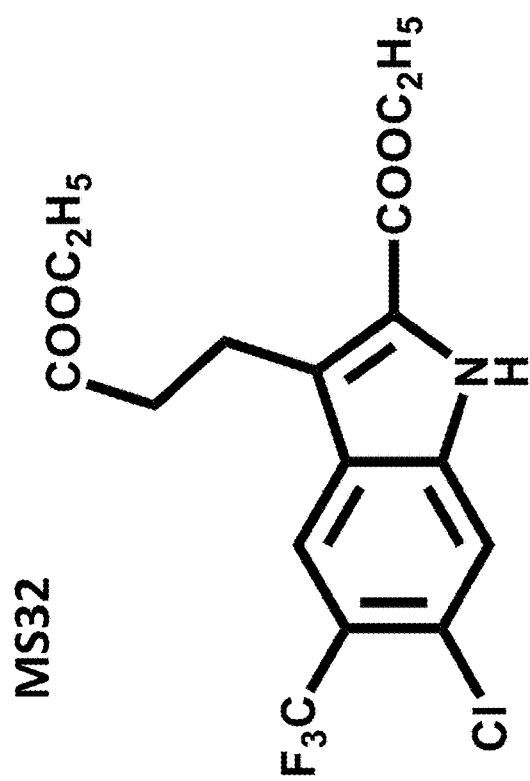
Figure 10C:
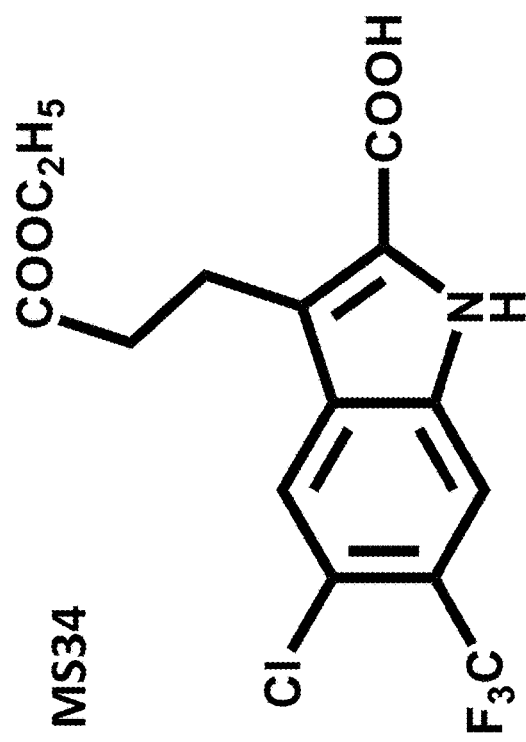
Figure 10D:
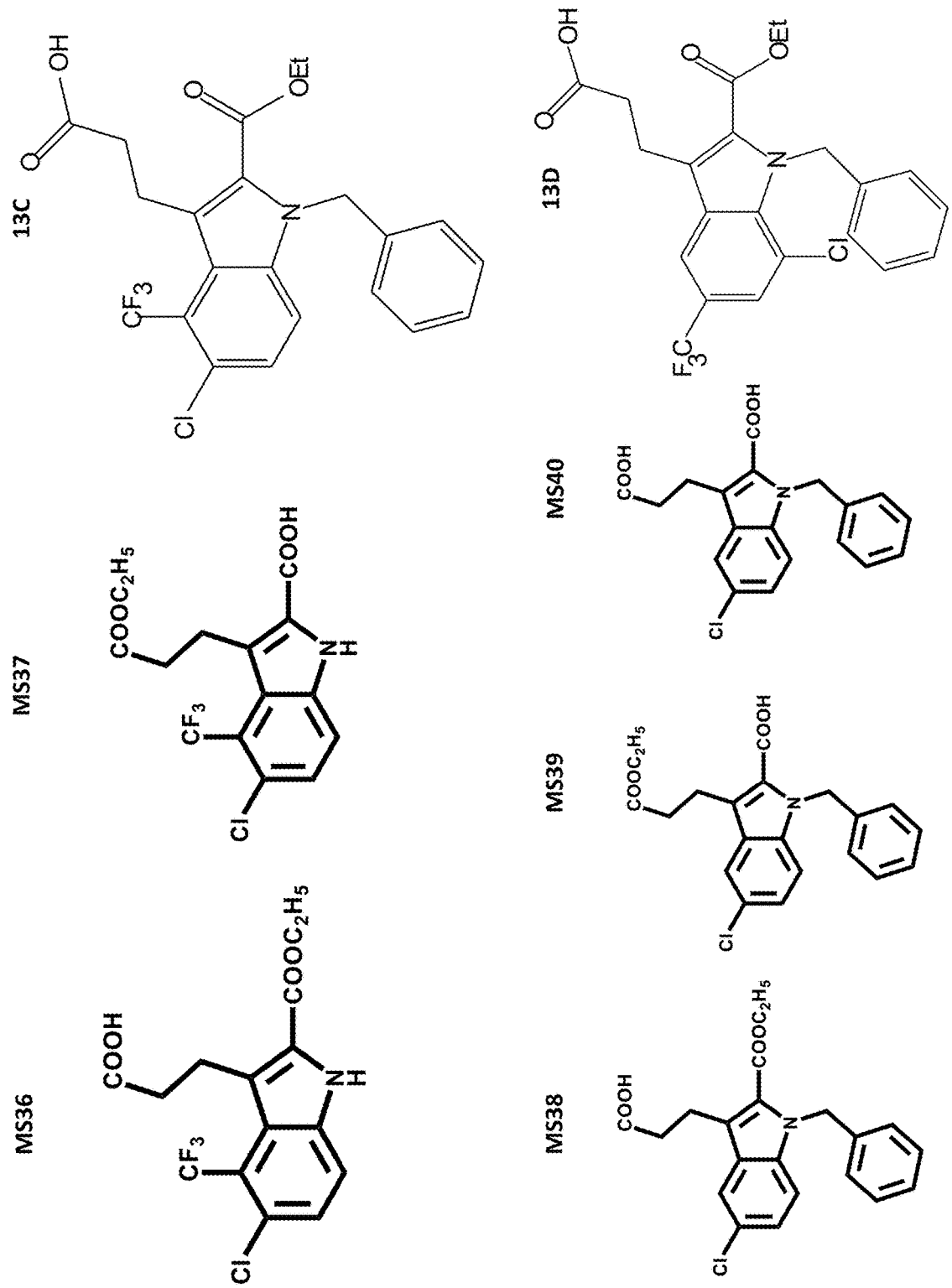
Figure 10E:
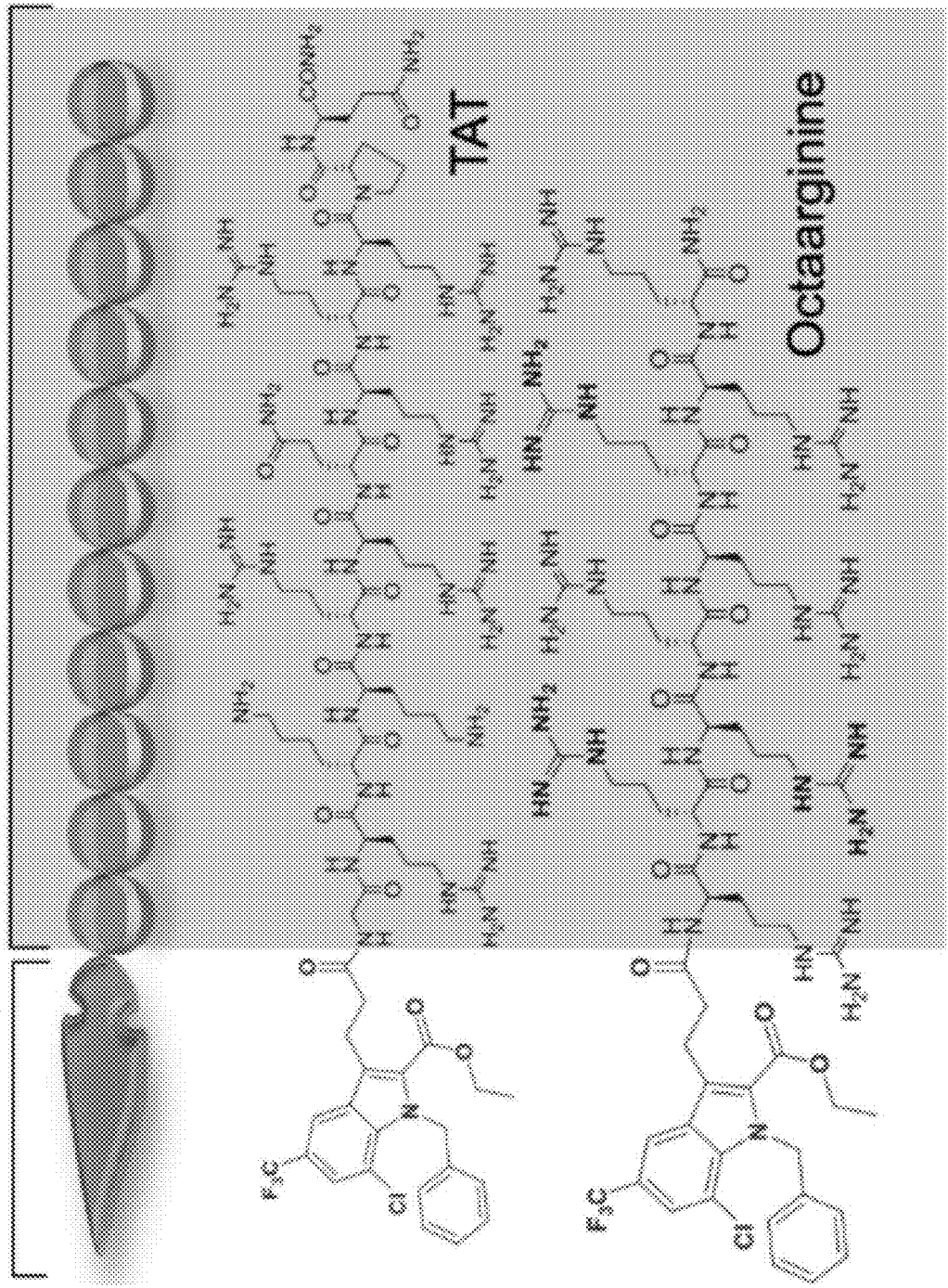

FIGS. 10A-E present indole derivatives that were synthesized based on the synthesis pathway presented in FIG. 9 (denoted as "MS23" to "MS40") together with two CPP-conjugates (FIG. 10E).

Figure 11A:
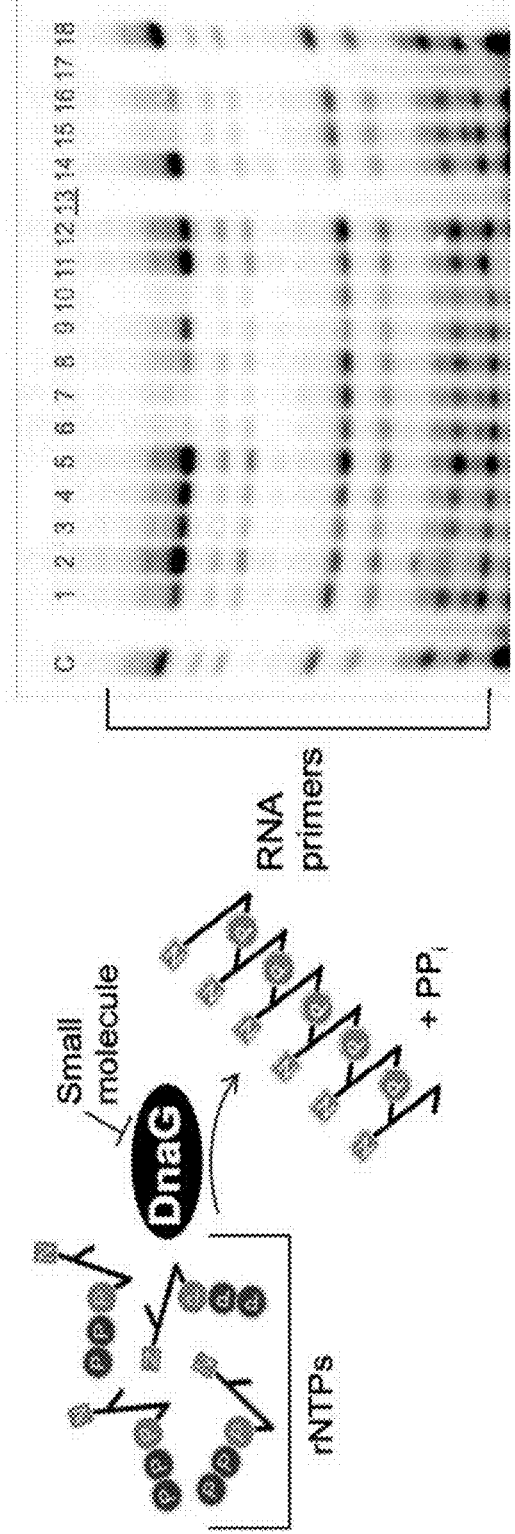
Figure 11B:
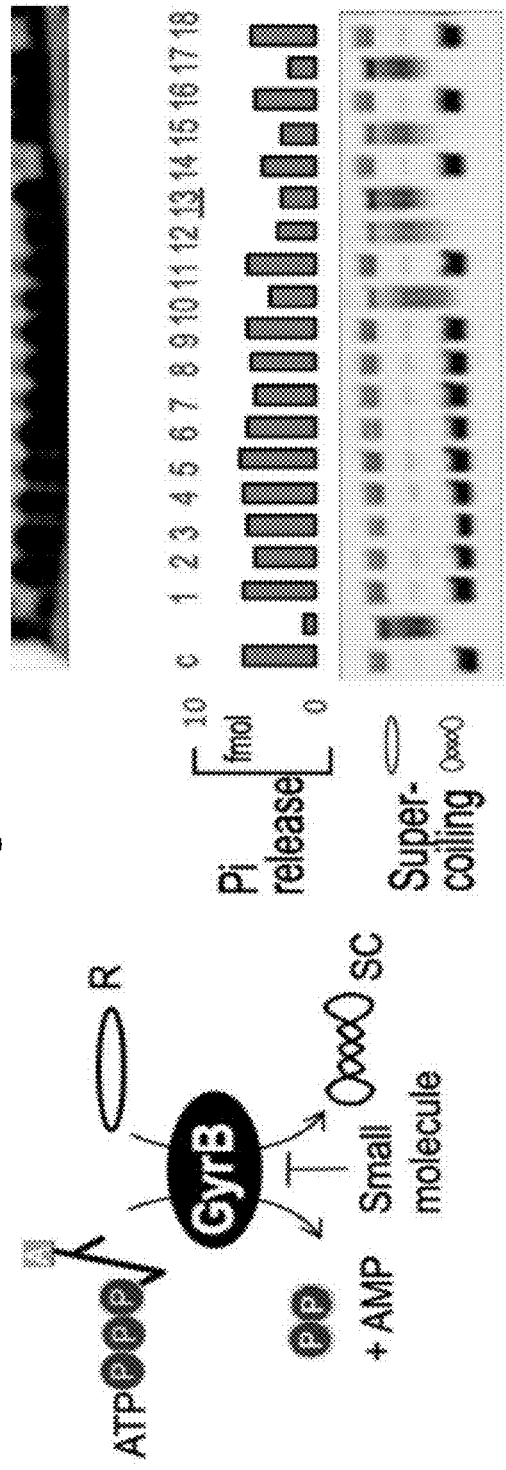
Figure 11C:
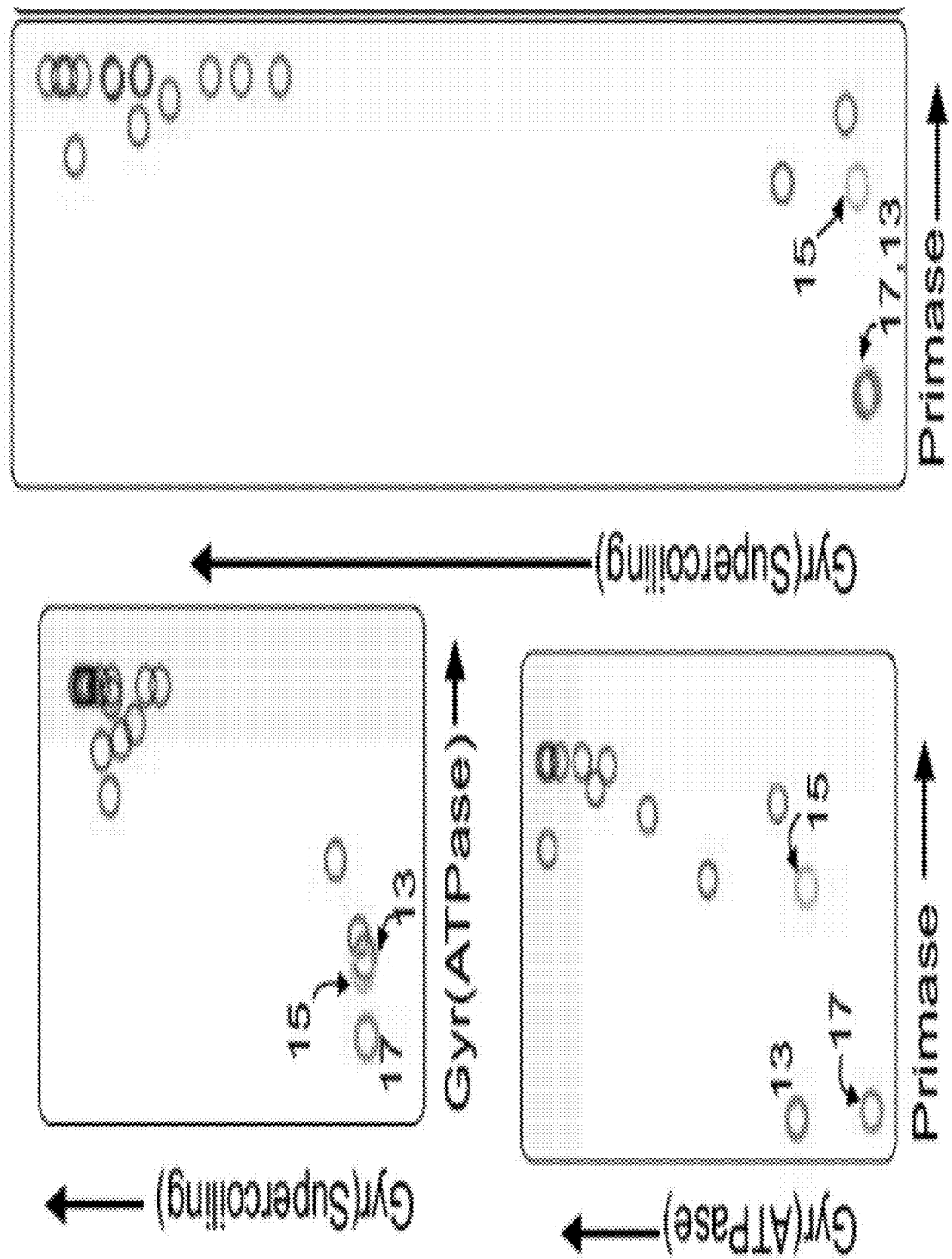

FIGS. 11A-C show inhibitory effect of synthesized molecules (as denoted in FIGS. 10A-D) on DnaG primase and gyrase from Mtb. Screening for best precursor molecule among 18 commercially available compounds by examining their inhibitory effect on specific Mtb DnaG primase (template-directed ribonucleotide synthesis) and gyrase activity (ATPase activity and DNA-supercoiling). FIG. 11A provides a scheme, representing the template-directed ribonucleotide synthesis reaction contained 500 nM Mtb DnaG primase, oligonucleotide (5'-CCGACCCGTCCGTAATA-CAGAGGTAATTGTCACGGT-3'), $\alpha$-$^{32}$P-ATP, CTP, GTP, UTP and 4 mM of experimental inhibitor in the standard reaction mixture. After incubation, the radioactive products were analyzed by electrophoresis through a 25% polyacrylamide gel containing 7 M urea and visualized by autoradiography. Gel bands represent RNA primers formed by Mtb DnaG. FIG. 11B provides a scheme, showing the enzymatic activity of the Gyrase—catalysis of negative supercoiling of a plasmid by using the energy obtained by hydrolyzing two ATP molecules. FIG. 11B Top shows inhibition of ATP hydrolysis by small molecule inhibitors. The reaction was incubated at 37° C. for 60 min in a 10 µL reaction with DNA Gyr (reconstitution of GyrA 36 nM and GyrB 18 nM), 13.24 ng/µL pBR322 DNA and 38 nM alpha-$^{32}$p-ATP in the presence of small molecule inhibitors. The reaction was stopped using Norit solution and the radioactivity of the supernatant was determined. FIG. 11B Bottom shows inhibition of DNA supercoiling by small molecule inhibitors. The reaction conditions were the same as the above. The reaction products were resolved in 1% agarose gel and followed by staining with EtBr. FIG. 11C provides a distribution map of the effect of inhibitors on the primase/Gyr activities. FIG. 11C Right shows primase vs. gyrase activity (supercoiling). FIG. 11C Left Top represents Gyr (supercoiling) vs. Gyr activity (ATPase). FIG. 11C Left Bottom represents Gyr (ATPase) vs. primase activity.

Compounds 13c and 13d were found to be the most effective exhibiting the total inhibition, and compounds MS37, MS38, MS26 and MS38 exhibits partial inhibition.

Figure 12A:
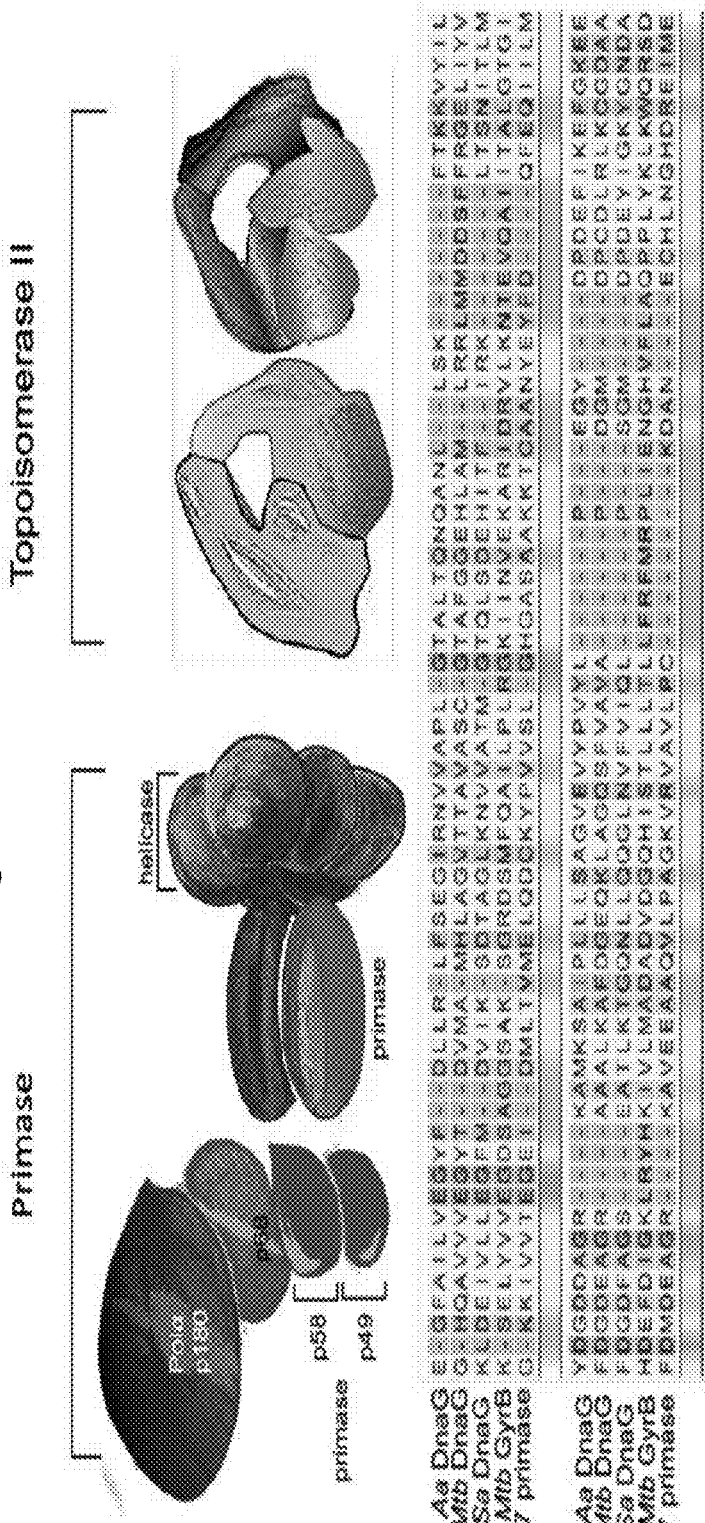
Figure 12B:
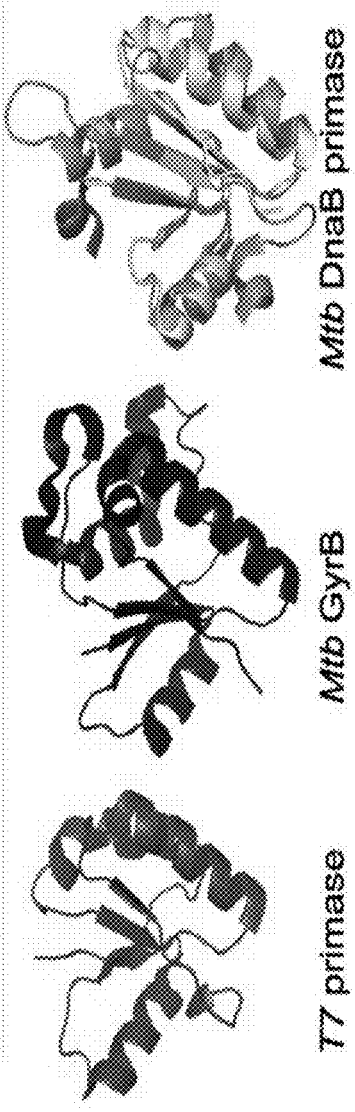

FIGS. 12A-B represent DNA primase and gyrase. FIG. 12A Top shows schematic representation of DNA priming system and DNA topoisomerase II in bacteria compared to their arrangements in human. FIG. 12A Left represents the DNA polymerase α-primase complex from human consisting of four subunits. The p180 subunit is pol α, p58 and p49 comprise primase, and p68 is the fourth, accessory subunit. FIG. 12A Right represents structural differences between human and bacterial type II topoisomerases. FIG. 12A Bottom represents multiple sequence alignment of bacterial DnaG primase. Amino acid residues are colored from red for the most conserved amino acids to blue for the less conserved ones. FIG. 12B presents sequence alignment of the TOPRIM domain revealing common sequence elements between DnaG primases and gyrases. Bacterial DnaG-like primases: T7 primase (red, PDBID 1NUI), part of the fused helicase-primase gp4 of bacteriophage T7 share a similar structure with DnaG from *Mycobacterium tuberculosis* (Mtb) (green, PDBID 5w33) and *Staphylococcus aureus* (*S. aureus*) (grey PDBID 4E2K). Mtb Gyr (PDBID 3m4i) is presented in blue.

Figure 13A:
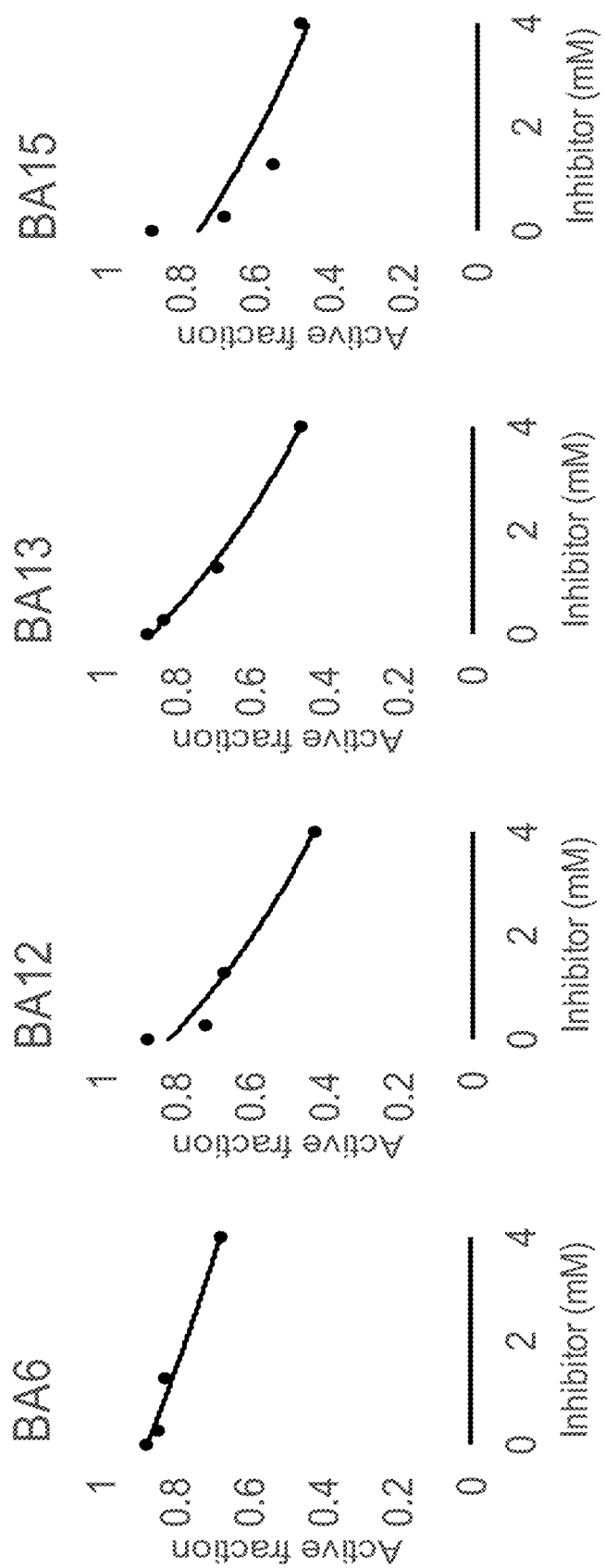
Figure 13B:
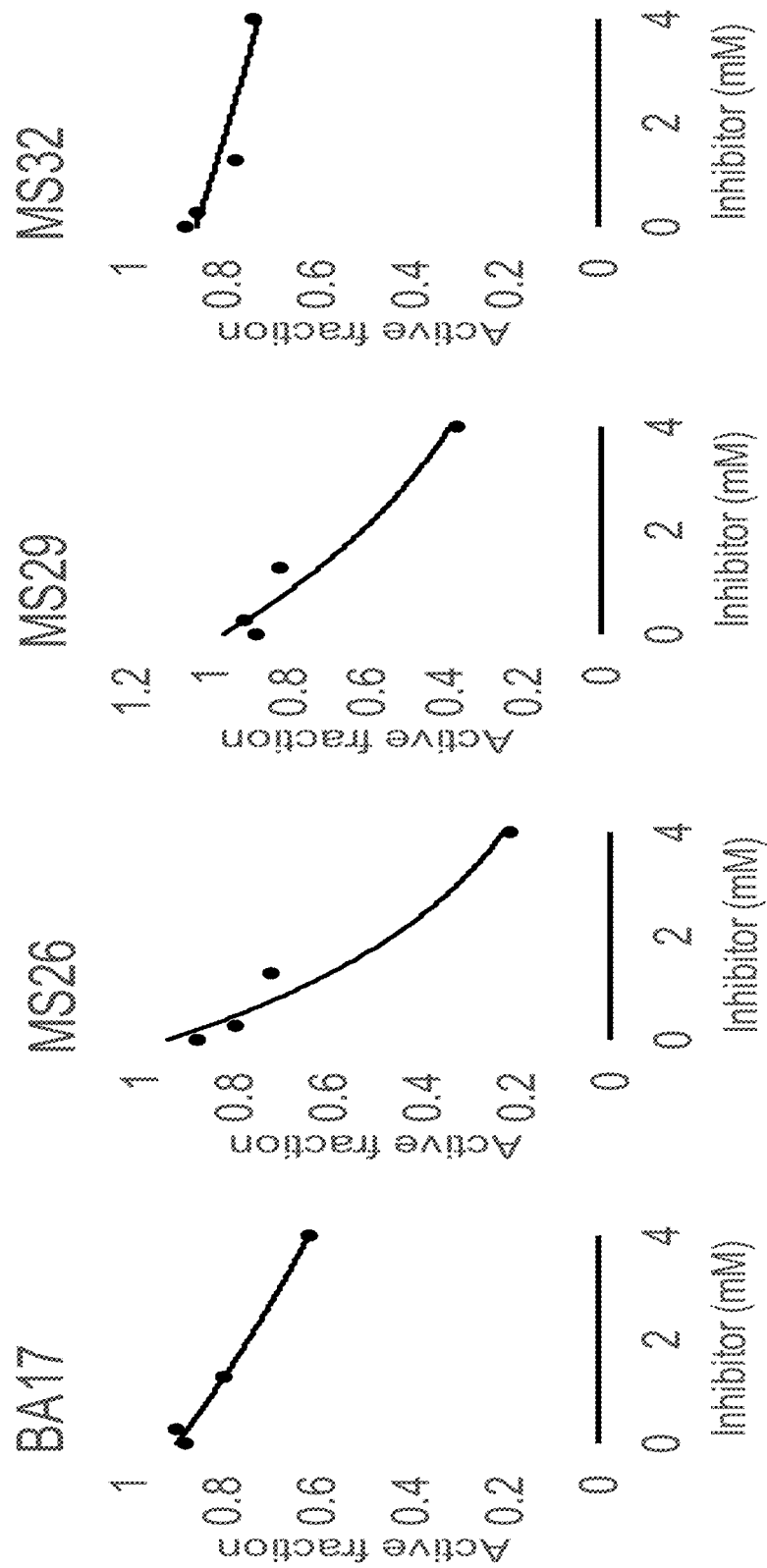

FIGS. 13A-B present graphs showing inhibition assay to examine the ability of selected molecules to inhibit *M. tuberculosis* DNA Gyrase. The molecules were originally designed to target DnaG primase. Molecules BA6, BA12, BA13, BA15, BA17 correspond to the molecules 6, 12, 13, 15, and 17 in FIGS. 3A-C, respectively. Molecules MS 26, MS29, and MS32 are presented in FIGS. 10A-D.

Figure 14C:
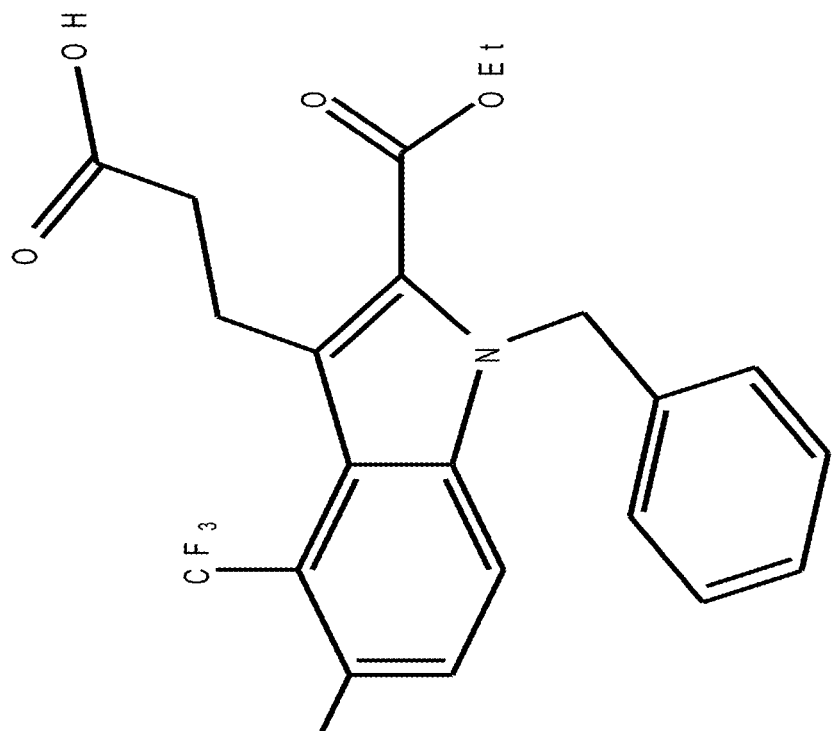
Figure 14C:
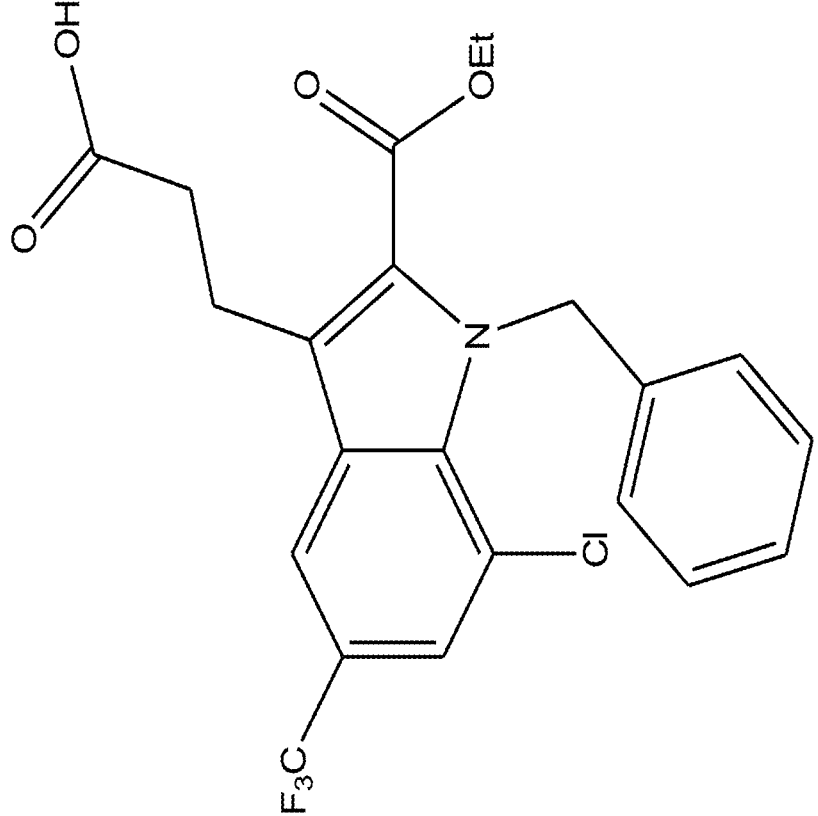

FIGS. 14A-C showing an effect of selected small molecule inhibitors on Msmg culture growth. FIG. 14A shows growth curves of Msmg culture expressing mCherry reporter protein for viability. The culture was grown in 7H9 liquid medium (0.4% glycerol, 0.05% Tween-80) containing different small molecule inhibitors in 250 µM concentration. The fluorescent signal originating form mCherry reporter protein was measured over the course of 20 hours and used to estimate viability of bacterial cells. Data represents the average of three replicates (n=3). Inset shows the effect of compounds 13c and 13d on the viability of Msmg (compared to isoniazid, INH, indicated in grey). FIG. 14B represents a dilution colony assay. Samples from the assay described in FIG. 14A were collected after incubation and serially diluted in 1:10 ratio. Each dilution was platted on a 7H10+ agar plate and incubated until bacterial colonies became visible. FIG. 14C represents chemical structure of compounds 13c and 13d.

Figure 15A:
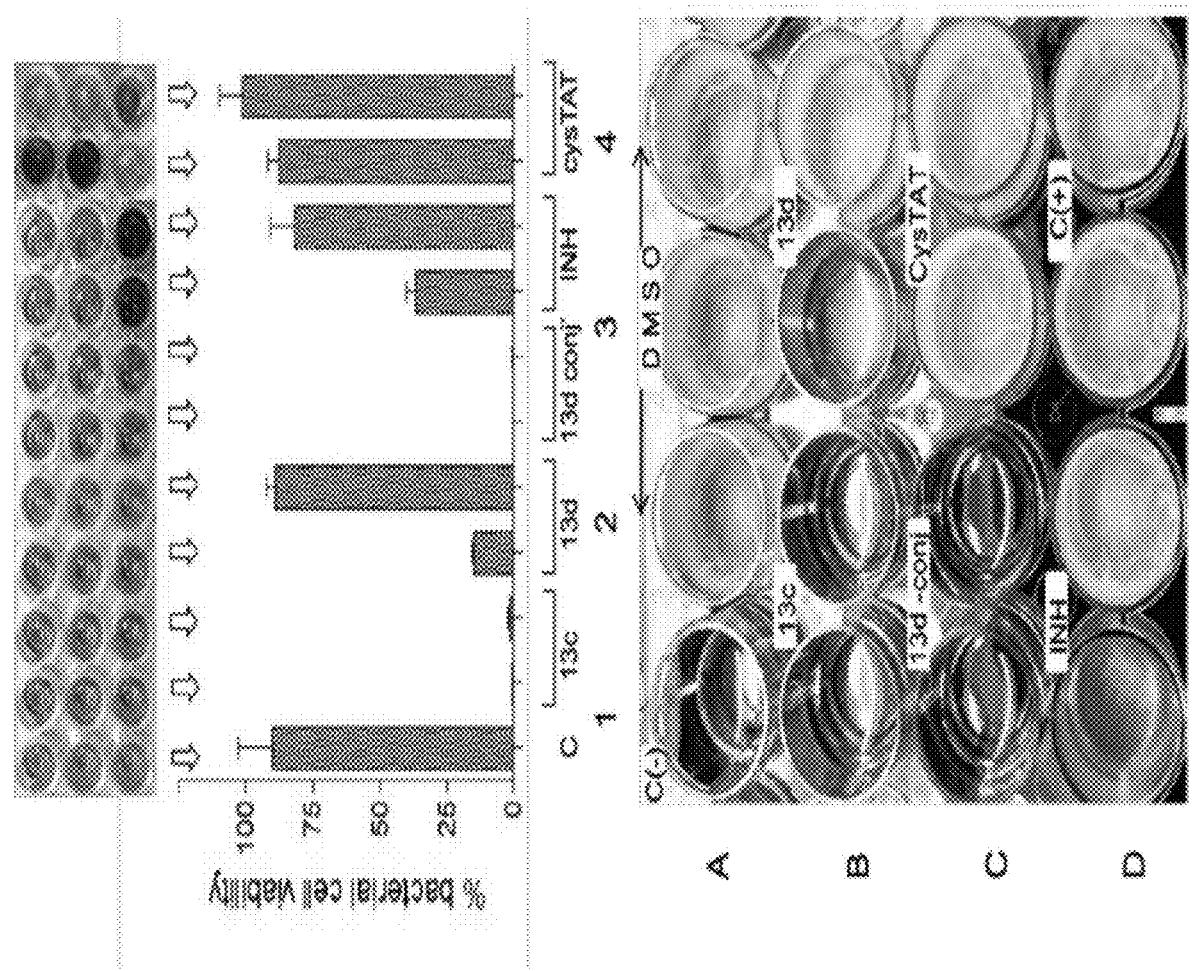
Figure 15B:
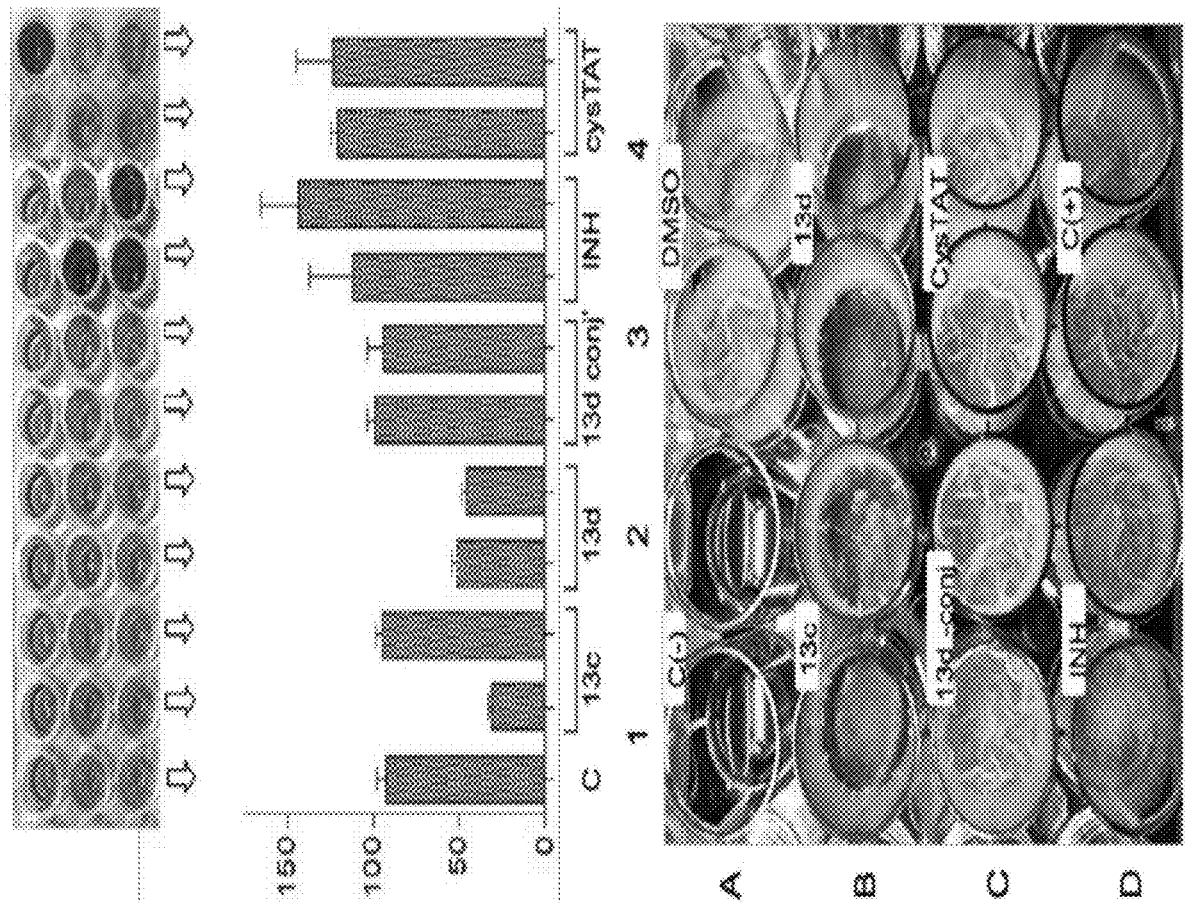

FIGS. 15A-B represent inhibition or eradication of biofilm by primase/gyr inhibitors. FIG. 15A shows inhibition of biofilm growth of Msmg mc$^2$155 by various concentration of selected inhibitors. A Top. Alamar blue viability assay of biofilm-embedded bacteria after treatment with selected inhibitors and their conjugates after growth over period of 3 d at 37° C. A Middle. Growth measurements. A Bottom. Optical image of five days old Msmg biofilm grown on polystyrene plate, where, A1 represents a negative control, A2 represents DMSO vehicle control 1.2%, A3 represents DMSO 0.62%, A4 represents DMSO 0.31%, B1 represents 13c (250 µM), B2 represents 13c (125 µM), B3 represents 13d (250 µM), B4 represents 13d (125 µM), C1 represents 13d-conjugated to CPP (13d-conj, 2 µM), C2 represents 13d-CPP (1 µM), C3 represents CPP only (8 µM), C4 represents CPP only (4 µM), D1 represents Isoniazid (INH, 250 µM), D2 represents INH (125 µM), D3-4 represents a positive control. B. Eradication of preformed biofilm of Msmg mc$^2$155. B Top. Alamar blue viability assay of preformed biofilm after treatment with selected inhibitors and their conjugates. B Middle. Growth measurements. B Bottom. Optical image of five days old Msmg biofilm grown on polystyrene plate, where, A1-2 represents a negative control, A3 represents DMSO 1.2%, A4 represents DMSO 0.62%, B1 represents 13c (250 µM), B2 represents 13c (125 µM), B3 represents 13d (250 µM), B4 represents 13d (125 µM), C1 represents 13d-conj (2 µM), C2 represents 13d-conj (1 µM), C3 represents CPP only (8 µM), C4 represents CPP only (4 µM), D1 represents Isoniazid (INH, 250 µM), D2 represents INH (125 µM), D3-4 represents a positive control.

13d-conj was found to be most the most potent compound, showing an efficient inhibition of biofilm growth. The chemical structure of 13d-conj is represented in FIG. 10E.

DETAILED DESCRIPTION OF THE INVENTION

The present invention, in some embodiments thereof, relates to compounds and compositions comprising same, e.g., for reducing or preventing growth of microorganisms. In some embodiments, the present invention is directed to a compound and a composition comprising an indole derivative conjugated to a cell penetrating peptide and use thereof such as for slowing bacterial proliferation.

The weak catalytic activity of DNA primase renders the adaptation of a functional assay to high throughput screening (HTS) a formidable challenge. The present inventors have contemplated the use of a hybrid method for developing small molecule inhibitors for primase and gyrase to circumvent the drawbacks of HTS. Based on the 'rational design' philosophy of lead development, the disclosed method may exploit nuclear magnetic resonance (NMR) to identify binders from libraries of fragment molecules.

The present invention is also directed to a method for reducing bacterial load in a subject in need thereof, comprising administering a compound described herein to the subject.

The present invention is based, in part, on the finding that an N-substituted indole derivative covalently linked to a cell penetrating peptide, exhibits an antibacterial effect (e.g., against Mtb) in the low micromolar concentration range.

As described herein, computational methods may be used to construct larger molecules with improved binding/inhibition properties. The use of fragment based virtual screening (FBVS) may yield potent inhibitors, reduce costs, and provide more advanced information about lead binding properties prior to the medicinal chemistry phase of drug optimization. Embodiments of the disclosed computational methods are described herein below and under the Examples section.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

According to an aspect of some embodiments of the present invention, there is provided a compound represented by Formula I:

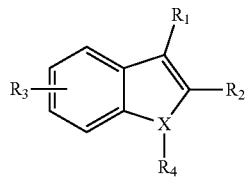

wherein:

$R_1$ and $R_2$ represent, independently in each occurrence, a group comprising or being selected from the group consisting of: a peptide, a thioalkoxy group, a mercapto group, hydrogen, alkyl, nitro, azo, guanidine, an alkoxy group, an amino group, a carboxylic acid derivative; or $R_1$ and $R_2$ are joined together so as to form a fused ring system;

$R_3$ (also referred to as "$R_{3a}$-$R_{3d}$") represents, independently in each occurrence, one to four groups selected from the group consisting of: an electron-withdrawing group, alkyl, a haloalkyl, a cycloalkyl group optionally comprising a heteroatom, aryl, a heteroaryl group, heteroalicyclic, heteroaryl, alkoxy, hydroxy, thiohydroxy, thioalkoxy, aryloxy, thioaryloxy, amino, cyano, nitro, azo, guanidine, amide, carboxy, sulfonyl, sulfoxy, sulfinyl, sulfonamide, an azide group, a vinyl group, an allyl group, an optionally substituted fused ring, and a phosphinyl group.

X is —N, or —CH;

and $R_4$ is selected from the group consisting of: hydrogen, alkyl, an aryl group, a heteroaryl group, a sulfinyl group, a sulfonate group, a cycloalkyl group, a heterocyclyl group, and alkaryl, substituted or non-substituted.

In some embodiments, X is N.

In some embodiments, the compound is represented by Formula Ia:

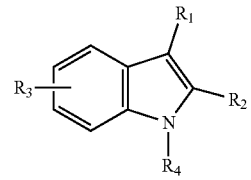

wherein:

$R_1$ and $R_2$, independently in each occurrence, comprise or are selected from the group consisting of: hydrogen, alkyl, amine, nitro, azo, guanidine, amide, or carboxy; or $R_1$ and $R_2$ are joined together so as to form a fused ring system;

$R_3$ represents, independently in each occurrence, one to four groups selected from the group consisting of: an electron-withdrawing group, alkyl, cycloalkyl, aryl, heteroalicyclic, heteroaryl, alkoxy, hydroxy, thiohydroxy, thioalkoxy, aryloxy, thioaryloxy, amino, trihalomethyl, cyano, nitro, azo, guanidine, amide, carboxy, sulfonyl, sulfoxy, sulfinyl, sulfonamide, or a fused ring, substituted or non-substituted;

and $R_4$ is selected from the group consisting of: hydrogen, alkyl, and alkaryl, substituted or non-substituted.

In some embodiments, $R_3$ comprises the electron-withdrawing group.

In some embodiments, the compound of Formula I is in the form of Formula Ia1:

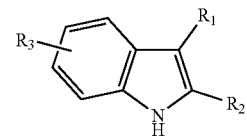

The phrases "electron-withdrawing substituent" or "electron-withdrawing group" are well known to those of skill in the art and are used herein interchangeably as their standard meaning which is a functional group that draws electrons to itself more than a hydrogen atom would if it occupied the same position in the molecule, as described in J. March, Advanced Organic Chemistry, third edition, Pub: John Wiley & Sons, Inc (1985).

Exemplary electron-withdrawing substituents include, but are not limited to, halogen, haloalkyl, haloalicyclic, haloaryl, haloheteroaryl, nitro group, a cyano group, an alkyloxy carboxylic ester bond, a sulfonyl group, a sulfonate group, a sulfinyl group, a sulfonamide group, an azo group, a guanidine group, and a carboxylic acid derivative, or any combination thereof.

In some embodiments, $R_1$ is —$CH_2CH_2R'$, wherein R' and $R_2$, independently in each occurrence, comprise or are selected from the group consisting of hydrogen, alkyl, amide, or carboxy.

In some embodiments, the compound is in the form of Formula IB:

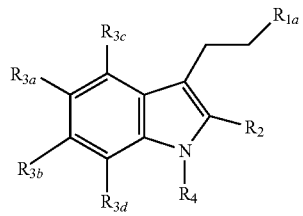

wherein:

$R_{1a}$ is selected from the group consisting of hydrogen, alkyl, amide, or carboxy; and up to three groups from $R_{3a-d}$ are selected from the group consisting of nitro, halo, and a fluorinated alkyl, and at least one groups from $R_{3a}$ to $R_{3d}$ is hydrogen.

In some embodiments, $R_4$ is absent, i.e. represented by Formula IBa:

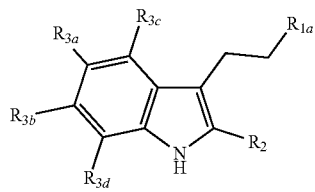

wherein:

$R_{1a}$ is selected from hydrogen, alkyl, amide, acyl, or carboxylic acid, or carboxy; $R_2$, $R_{3a-d}$, and $R_4$, are as defined hereinabove for $R_2$, $R_3$, and $R_4$, respectively.

In some embodiments, up to three substituents from $R_{3a-d}$ are selected from: alkyl, nitro, halo, and a fluorinated alkyl, and at least one substituent from $R_{3a-d}$ is absent.

In some embodiments, the halo is chlorine.

In some embodiments, the fluorinated alkyl is —$CF_3$.

In some embodiments, the compound is in the form of Formula IA1:

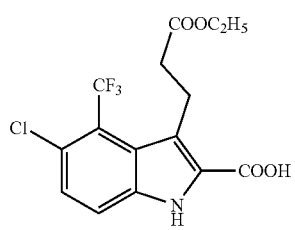

In some embodiments, the compound is in the form of Formula IB1:

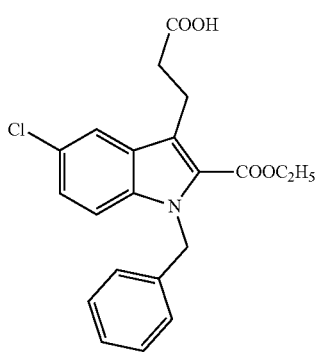

In some embodiments, the compound is in the form of Formula IA2:

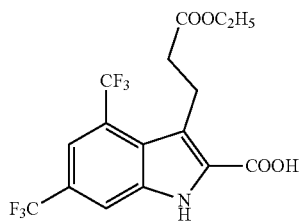

In some embodiments, the compound is in the form of Formula IA3:

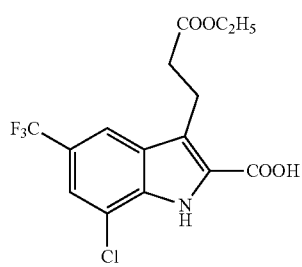

In some embodiments, the compound is in the form of Formula IA4:

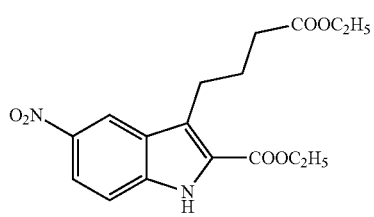

In some embodiments, the compound is in the form one products 1-51, as defined below:

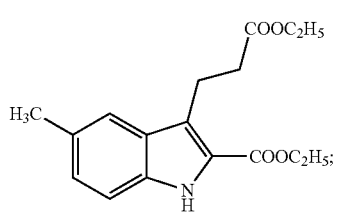

product 1

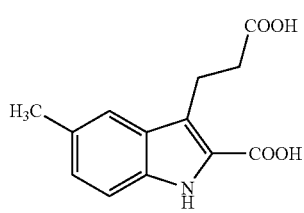

product 2

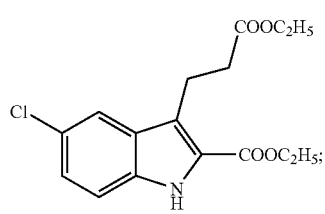

product 3

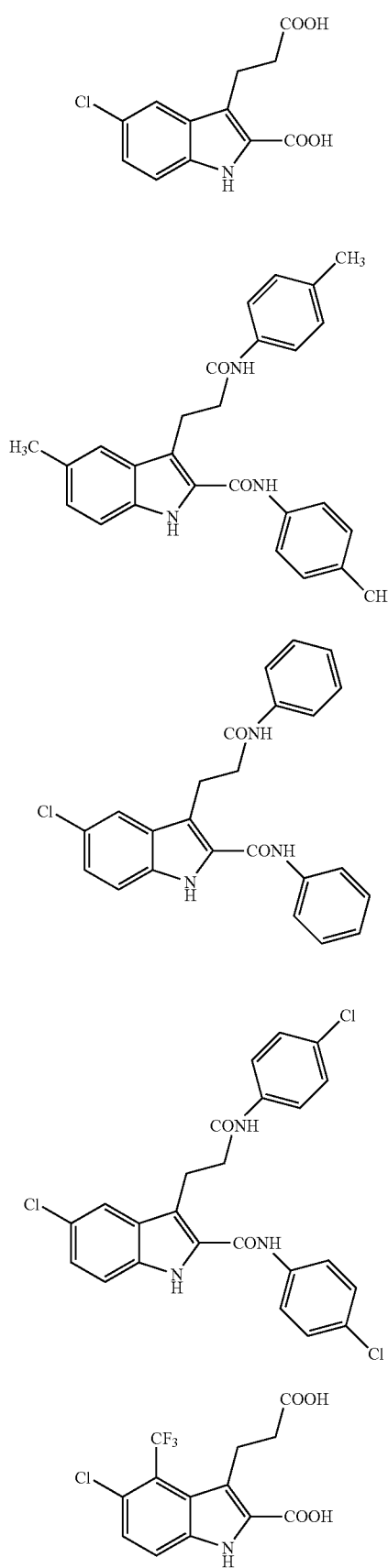

product 16: 4-CF3, 6-CF3 indole with 3-(CH2CH2COOH) and 2-COOH product 17: 5-NO2 indole with 3-(CH2CH2COOC2H5) and 2-COOC2H5 product 18: 5-NO2 indole with 3-(CH2CH2COOH) and 2-COOH product 19: 6-NO2 indole with 2-COOC2H5 product 20: 6-NO2 indole with 2-COOH product 21: 5-Cl indole with 3-CHO and 2-CHO product 22: 5-Cl indole with 3-(CH2CH2CH=NOH) and 2-CH=NOH product 23: 4-CF3, 5-Cl indole with 3-(CH2CH2COOH) and 2-COOH product 24: 5-Cl, 6-CF3 indole with 3-(CH2CH2COOH) and 2-COOH product 25: 5-CF3, 7-Cl indole with 3-(CH2CH2COOH) and 2-COOH product 26: 5-NO2 indole with 3-(CH2CH2CH2COOH) and 2-COOH product 27: 5-Cl indole with 3-(CH2CH2COOH) and 2-COOH product 28: 5-NO2 indole with 3-(CH2CH2COOH) and 2-COOC2H5 product 29: 5-NO2 indole with 3-(CH2CH2COOC2H5) and 2-COOH product 30: 4-CF3, 6-CF3 indole with 3-(CH2CH2COOH) and 2-COOC2H5 product 31
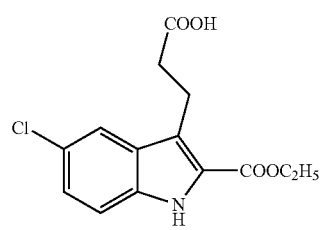
product 32
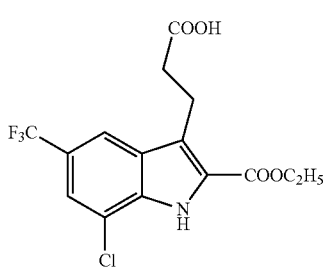
product 33
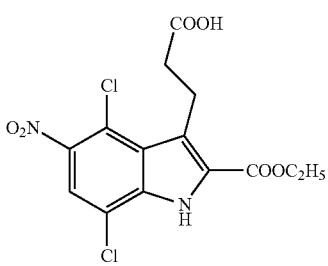
product 34
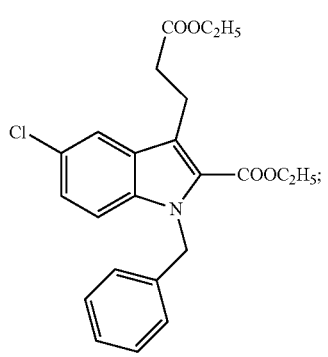
product 35
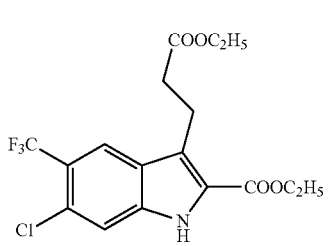
product 36
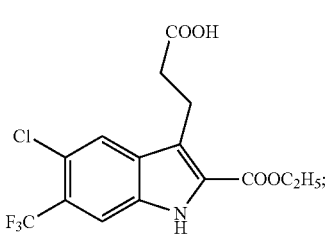
product 37
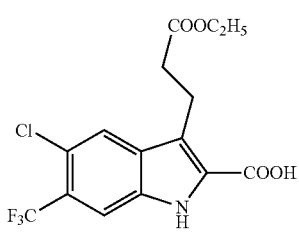
product 38
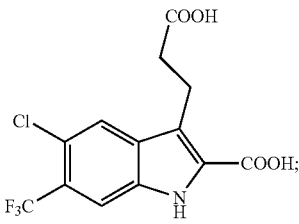
product 39
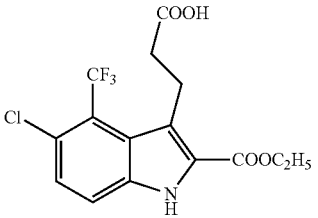
product 40
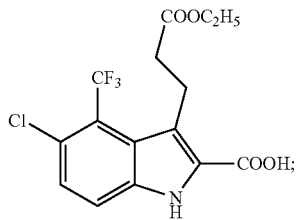
product 41
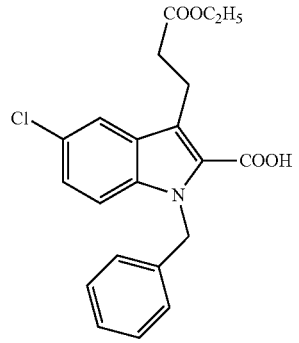
product 42
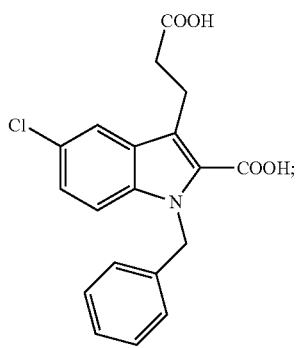

product 43, product 44, product 45, product 46, product 47, product 48, product 49, product 50, product 51

In some embodiments, the compound is in the form of Formulae IC1-9:

IC1, IC2

-continued

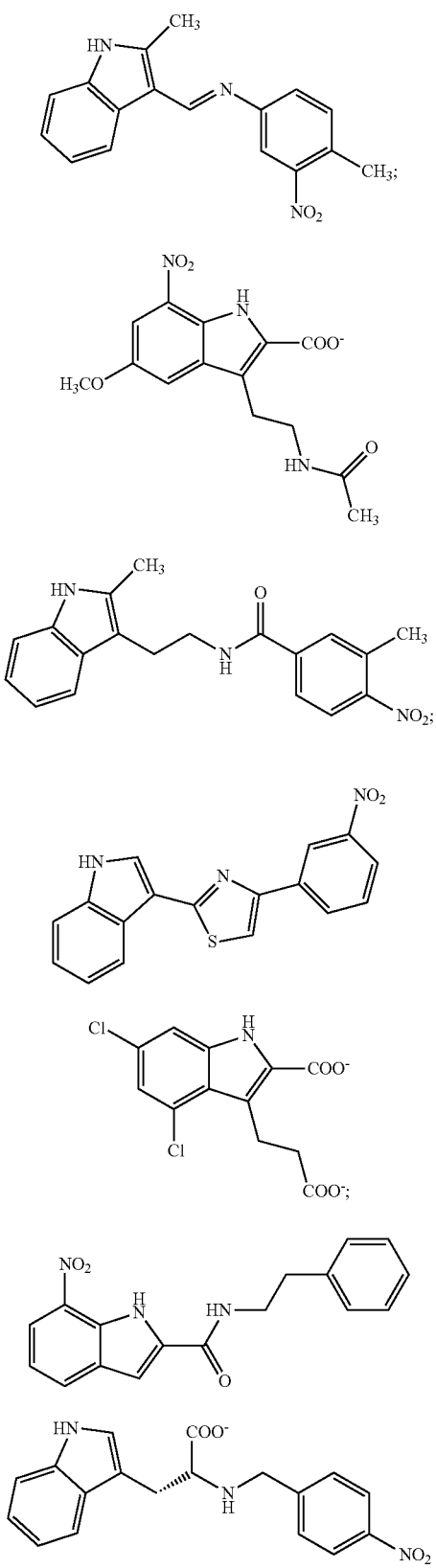

In some embodiments, the compound is in the form of Formula ID1:

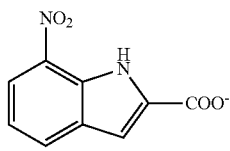

In some embodiments, the compound is in the form of Formula ID2:

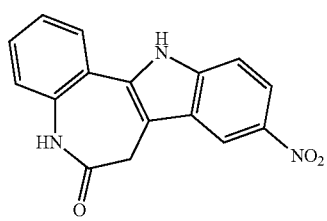

In some embodiments, the compound is in the form of Formula IE:

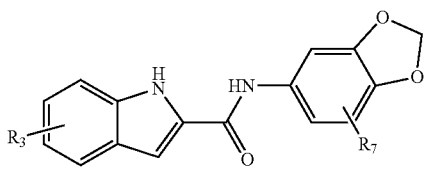

wherein:

$R_3$ is as defined hereinabove and $R_7$ represents one to three substituents, independently in each occurrence, comprising or being selected from hydrogen, alkyl, cycloalkyl, aryl, heteroalicyclic, heteroaryl, alkoxy, hydroxy, thiohydroxy, thioalkoxy, aryloxy, thioaryloxy, amino, nitro, halo, trihalomethyl, cyano, amide, carboxy, sulfonyl, sulfoxy, sulfinyl, sulfonamide, or a fused ring, substituted or non-substituted.

In some embodiments, by "fused ring" it is meant to refer to a cyclic ring.

In some embodiments, by "cyclic ring" it is meant to refer to "heterocyclic ring", and in some embodiments, the heterocylic ring is a heteroaryl.

In some embodiments, the compound is in the form of Formula IF:

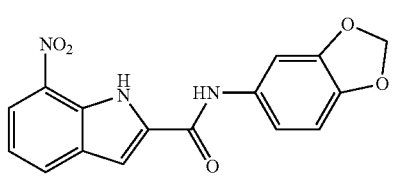 [SMILES: O=C(Nc1ccc2c(c1)OCO2)c1cc2cccc([N+](=O)[O-])c2[nH]1]

In some embodiments, the compound is in the form of Formula II:

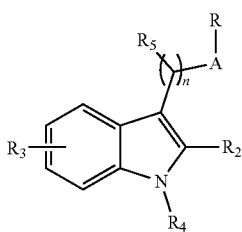

wherein:

n equals 0 to 10;

A comprises a covalent bond selected from the group consisting of:

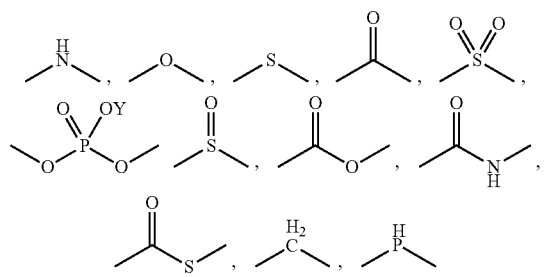

wherein Y is an alkyl group;

$R_{1a}$ independently comprises or is selected from the group consisting of: a peptide, hydrogen, a carboxylic acid derivative an alkyl group, an aryl group, and a heteroaryl group;

$R_2$ independently comprises or is selected from the group consisting of: hydrogen, an alkyl group, a peptide, —$(CH2)_{0-5}$-C(O)$OR_b$, —$(CH2)_{0-5}$-C(O)$SR_b$, and —$(CH2)_{0-5}$-C(O)$NR_b$, wherein $R_b$ is selected from the group consisting of: hydrogen, a $C_1$-$C_6$ alkyl group, an aryl group, and a heteroaryl group;

each $R_5$ is independently selected from the group consisting of: hydrogen, a $C_1$-$C_{12}$ alkyl group, an aryl group, a $C_4$-$C_{20}$ cycloalkyl group, a mercapto group, an amino, a hydroxy group, a halo group, a cyano group, a nitro group, a carboxylic acid derivative, a $C_1$-$C_{10}$ alkyl group comprising a heteroatom, a haloalkyl group, an alkoxy group, an alkylhydroxy group, a sulfinyl group, a sulfone group, a sulfonate group, and a phosphine group;

and $R_3$ represents up to three substituents, being independently selected from the group consisting of: a trihalomethyl group, a fluorinated alkyl group, a cyano group, a nitro group, a halo group, a sulfonyl group, a sulfonate group, a sulfinyl group, a sulfonamide group, an azo group, a guanidine group, and a carboxylic acid derivative.

In some embodiments, A is selected from the group consisting of: an amide group, a carboxy group, an ester group, a thioester group. In some embodiments, A is an amide group.

In some embodiments, $R_5$ is selected from the group consisting of: hydrogen, a $C_1$-$C_{12}$ alkyl group, a mercapto group, an amino, a hydroxy group, a halo group, a cyano group, a nitro group, a carboxylic acid derivative, a $C_1$-$C_{10}$ alkyl group comprising a heteroatom, a haloalkyl group, an alkoxy group, an alkylhydroxy group, a sulfinyl group, a sulfone group, a sulfonate group, and a phosphine group.

In some embodiments, $R_5$ is selected from the group consisting of: hydrogen, a $C_1$-$C_{12}$ alkyl group, a mercapto group, an amino, a hydroxy group, a halo group, a cyano group, a nitro group, and a carboxylic acid derivative.

In some embodiments, $R_5$ is selected from the group consisting of: hydrogen, a $C_1$-$C_{12}$ alkyl group, a mercapto group, an amino, a hydroxy group, a halo group, a cyano group, and a nitro group.

In some embodiments, $R_5$ is an optionally substituted $C_1$-$C_{12}$ alkyl group. In some embodiments, $R_5$ is hydrogen.

In some embodiments, $R_2$ is an alkyl-amide group. In some embodiments, $R_2$ is —C(O)$NR_b$. In some embodiments, $R_2$ is an alkyl-ester group. In some embodiments, $R_2$ is —C(O)$OR_b$.

In some embodiments, $R_4$ comprises a $C_1$-$C_3$ alkyl group, wherein one methylene unit is replaced with a substituent selected from the group consisting of: a $C_6$-$C_{10}$ aryl, a $C_5$-$C_{10}$ heteroaryl, a $C_5$-$C_{12}$ cycloalkyl group, and a $C_5$-$C_{12}$ heterocyclyl group.

In some embodiments, n represents a plurality of methylene units. In some embodiments, n equals 0 to 4. In some embodiments, n equals 1 to 2. In some embodiments, n equals 1.

In some embodiments, the compound is in the form of Formula IIa:

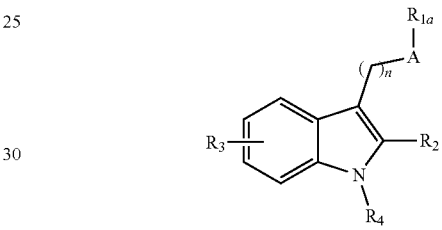

wherein n, A, $R_{1a}$, $R_2$, $R_3$, and $R_4$ are as defined hereinabove.

In some embodiments, the compound is in the form of Formula IIb:

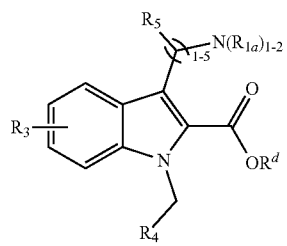

wherein $R_{1a}$, $R_2$, $R_3$, $R_4$ and $R_5$ are as defined hereinabove.

In some embodiments, the compound is in the form of Formula IIc:

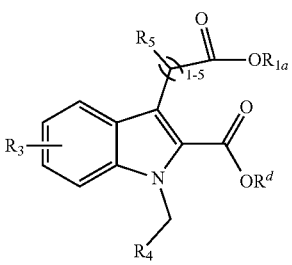

wherein $R_{1a}$, $R_2$, $R_3$, $R_4$ and $R_5$ are as defined hereinabove.

In some embodiments, the compound is in the form of Formula IId:

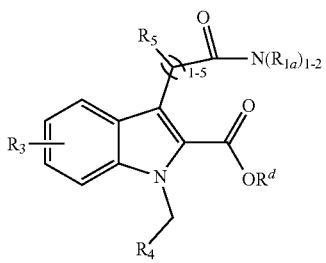

wherein $R_{1a}$, $R_2$, $R_3$, $R_4$ and $R_5$ are as defined hereinabove.

In some embodiments, the compound is in the form of Formula III:

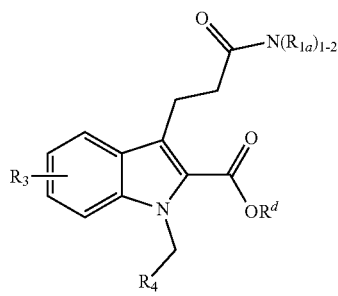

wherein:
$R^d$ is selected from the group consisting of: an ethyl group, a methyl group, a propyl group, and hydrogen;
$R_{1a}$ comprises a peptide;
and $R_3$ represents at least two substituents, being independently selected from the group consisting of: a nitro group, a halo group, and a fluorinated alkyl group.

In some embodiments, the compound is in the form of Formula IIIa:

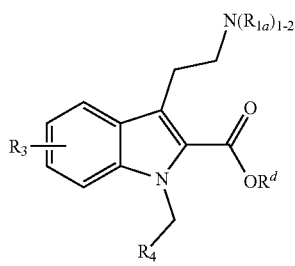

wherein $R_{1a}$, $R^d$, $R_3$, and $R_4$ are as defined hereinabove.

In some embodiments, the compound is in the form of Formula IIIb:

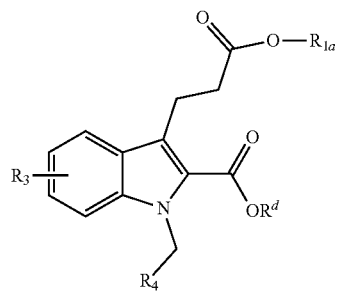

wherein $R_{1a}$, $R^d$, $R_3$, and $R_4$ are as defined hereinabove.

In some embodiments, $R_{1a}$ is a peptide.
In some embodiments, $R^d$ is ethyl.
In some embodiments, $R_3$ represents at least two substituents, being independently selected from a halo group, and a fluorinated alkyl.
In some embodiments, $R_3$ represents at least two substituents, being independently selected from the group consisting of: —Cl, and —CF$_3$.
In some embodiments, $R_4$ is selected from the group consisting of:

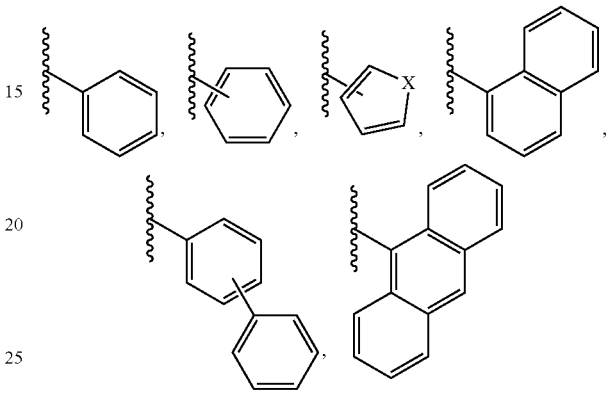

wherein X is a heteroatom.

In some embodiments, $R_4$ is a $C_5$-$C_6$ heteroaryl group. In some embodiments, $R_4$ is a substituted phenyl group. In some embodiments, $R_4$ is a phenyl group.

In some embodiments, the compound is in the form of Formula IV:

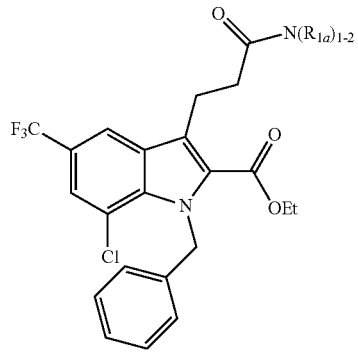

wherein each $R_{1a}$ is as defined hereinabove.

In some embodiments, the compound is in the form of Formula IVa:

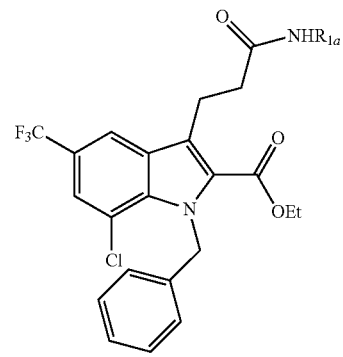

wherein $R_{1a}$ is as defined hereinabove.

In some embodiments, the compound is in the form of Formula V:

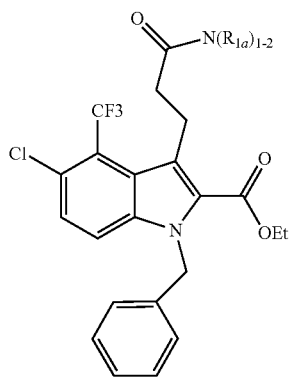

wherein each $R_{1a}$ is as defined hereinabove.

In some embodiments, the compound is in the form of Formula Va:

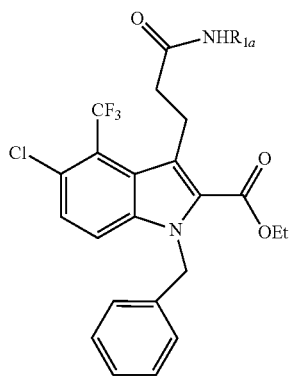

wherein $R_{1a}$ is as defined hereinabove.

According to an aspect of some embodiments of the present invention, there is provided a compound represented by Formula VI:

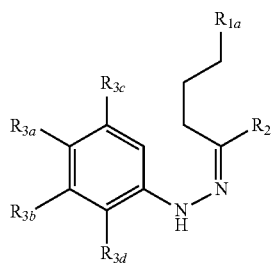

wherein $R_{1a}$, $R_2$, $R_{3a-d}$ are as defined hereinabove.

In some embodiments, the compound is in the form of Formulae VI1-3:

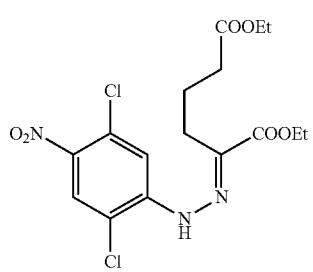

II-1

-continued

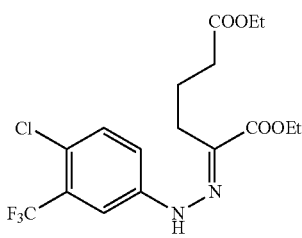

II-2

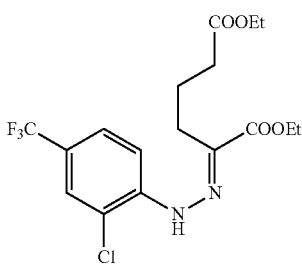

II-3

In some embodiments, the compound is in the form Formula VII:

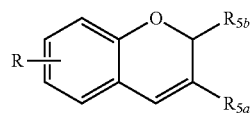

wherein at least one group from $R_{a-b}$, independently, in each occurrence, is selected from the group consisting of hydrogen, alkyl, amide, or carboxy, substituted or non-substituted;

$R_6$ represents hydrogen, or one to four substituents, independently in each occurrence, comprising or being selected from alkyl, cycloalkyl, aryl, heteroalicyclic, heteroaryl, alkoxy, hydroxy, thiohydroxy, thioalkoxy, aryloxy, thioaryloxy, amino, nitro, halo, trihalomethyl, cyano, amide, carboxy, sulfonyl, sulfoxy, sulfinyl, sulfonamide, or a fused ring, substituted or non-substituted.

In some embodiments, the compound is in the form of Formula VIIB:

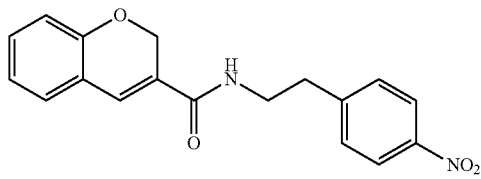 [SMILES: O=C(NCCc1ccc([N+](=O)[O-])cc1)C1=Cc2ccccc2OC1]

In some embodiments, the compound is in the form of Formulae VIIC-1 to 3:

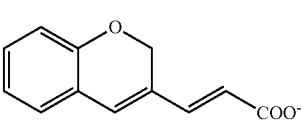

VIIC-1

VIIC-2

[structure: chlorinated 2H-chromene with CH=CH-COO⁻ substituent]

VIIC-3

[structure: 2-methyl-2H-chromene with CH=CH-COO⁻ substituent]

Peptide

In some embodiments, there is a compound represented by any one of Formulae II to VI, wherein $R_{1a}$ is a peptide. In some embodiments, the compound is a peptide conjugate comprising a peptide and an indole derivative. In some embodiments, a peptide is conjugated to an indole derivative via a C-terminus. In some embodiments, a peptide is conjugated to an indole derivative via an N-terminus. In some embodiments, the N-terminus of the peptide is conjugated to an indole derivative via an amide bond, as represented by Formulae IV to VI.

In some embodiments, a peptide is a synthetic peptide. In some embodiments, the peptide further comprises a linker. In some embodiments, a linker is bound covalently to the N-terminus of the peptide. In some embodiments, the peptide comprises an amino acid sequence. In some embodiments, the peptide comprises a plurality of sequences, which are connected via a linker.

As used herein, the term "linker" encompasses a spacer group that may be inserted at the N-terminus of the peptide, or between any two amino acid residues of the sequence.

Non-limiting examples of linker include but are not limited to: an alkyl group, and an amino acid spacer or any combination thereof. In some embodiments, an amino acid spacer is selected form the group consisting of: β-alanine, glycine, and amino hexanoic acid or any combination thereof. In some embodiments, the linker comprises one or more amino acid residues in peptoid form.

In some embodiments, the peptide comprises 3 to 60 amino acids. In some embodiments, the peptide comprises 3 to 20 amino acids.

The term "peptide", as used herein encompass native peptides, peptidomimetics (typically including non-peptide bonds or other synthetic modifications) and the peptide analogs: pseudo peptides, peptoids and semi-peptoids or any combination thereof. In another embodiment, the term "peptide" apply to amino acid polymers in which at least one amino acid residue is an artificial chemical analog of a corresponding naturally occurring amino acid.

In some embodiments, the peptide comprises D-amino acid.

In some embodiments, the peptide further comprises a chemical modification selected from the group consisting of: amidation, cyclization, and pegylation or any combination thereof.

In some embodiments, the peptide conjugated to the small molecule via the N-terminus, comprises a chemical modification of the C-terminus. In some embodiments, the peptide comprises a C-terminal amide group.

In some embodiments, the peptide comprises a cell penetrating moiety. The term "cell penetrating moiety" refers to a chemical entity which induces cellular internalization of a molecule comprising such moiety. The term "cellular internalization" refers to the ability of the peptide conjugate to enter the cell barrier.

In some embodiments, the peptide comprises a cell penetrating peptide (CPP). In some embodiments, the peptide is a CPP.

The term "cell penetrating peptide" and "CPP" as described herein are used interchangeably and refers to an amino acid sequence which internalize molecule comprising such sequence into a cell. In some embodiments, the molecule comprising CPP is a CPP conjugate. The CPP is intended to encompass not only the cell penetrating sequence, but also derivatives thereof that induce cellular internalization of a CPP conjugate.

In some embodiments, the CPP comprises between 3 and 20 contiguous arginine residues. In some embodiments, the CPP comprises between 4 and 10 contiguous arginine residues. In some embodiments, the CPP comprises contiguous arginine residues as set forth in Formula 1: nR, wherein R is arginine and "n" is an integer ranging from 3 to 20. In some embodiments, "n" is an integer ranging from 4 to 10, from 4 to 8, from 6 to 8, from 10 to 20. Each possibility represents a separate embodiment of the present invention.

In some embodiments, the CPP comprises contiguous lysine residues as set forth in Formula 2: nK, wherein K is lysine and "n" is an integer ranging from 3 to 20. In some embodiments, "n" is an integer ranging from 4 to 10, from 4 to 8, from 6 to 8, from 10 to 20. Each possibility represents a separate embodiment of the present invention.

In some embodiments, the CPP comprises the amino acid sequence as set forth in SEQ ID NO: 2 (RRRRRRRR).

In some embodiments, the CPP further comprises at least one lysine residue. In some embodiments, the CPP comprises arginine (R) and lysine (K).

In some embodiments, the CPP comprises a hydrophilic residue and a hydrophobic spacer. In some embodiments, the hydrophilic residue is selected from R and K. In some embodiments, the hydrophobic spacer is selected form the group consisting of: amino hexanoic acid (Ahx), β-alanine, and amino pentanoic acid. In some embodiments, the CPP comprises the amino acid sequence as set forth in Formula 2: (R-Ahx-R)n, wherein "n" is an integer ranging from 2 to 20.

In some embodiments, the CPP comprises an amino acid sequence selected from the group consisting of: an antennapedia sequence as set forth in SEQ ID NO: 4 (RQIKIWFQNRRMKWKK), an HIV-TAT sequence as set forth in SEQ ID NO: 1 (GRKKRRQRRRPQ), and a transportan sequence as set forth in SEQ ID NO: 5 (GWTLNSAGYLLGKINLKALAALAKKIL).

In some embodiments, the CPP sequence is selected from the group consisting of: SEQ ID NO: 1 (GRKKRRQRRRPQ), and SEQ ID NO: 2 (RRRRRRRR).

In some embodiments, the compound of the present invention is represented by Formula IV:

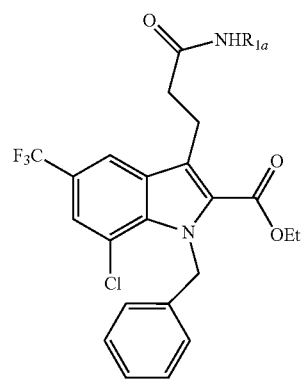

wherein $R_{1a}$ is selected from the group consisting of: SEQ ID NO: 1 (GRKKRRQRRRPQ), and SEQ ID NO: 2 (RRRRRRRR).

In some embodiments, the compound of the present invention is represented by Formula V:

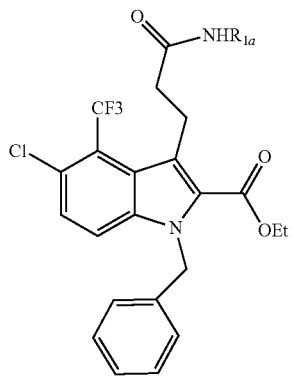

wherein $R_{1a}$ is selected from the group consisting of: SEQ ID NO: 1 (GRKKRRQRRRPQ), and SEQ ID NO: 2 (RRRRRRRR).

Method of Treatment

In some embodiments, at least one compound from the herein disclosed compounds (or the composition comprising the same) is for use for treating a medical condition associated with the expression of DNA primase and/or gyrase.

In some embodiments, the compounds for treating a medical condition associated with the expression of DNA primase are selected from Formulae IA1 and IB1 as denoted herein.

In exemplary embodiments, the compounds for use in reducing the expression of DNA primase and/or gyrase are selected from Formulae V and VI as denoted herein.

In some embodiments, "DNA primase" represents a class of RNA polymerase. In some embodiments, "DNA primase" refers to a bacterial DNA primase. In some embodiments, by "treating a medical condition associated with the expression of DNA primase" it is meant to refer to modulating DNA primase activity, e.g., the ability to synthesize RNA.

As used herein, the term "modulating" in reference to DNA primase activity includes any measurable alteration, e.g., the inhibition of DNA primase activity.

In some embodiments, the disclosed composition is packaged in a packaging material and identified, in or on the packaging material, for use in treating a medical condition associated with the expression of DNA primase. In some embodiments, "DNA primase" refers to a bacterial DNA primase.

In some embodiments, the disclosed compound or the composition is for use for selectively modulating bacterial DNA primase. In some embodiments, by "selectively modulating bacterial DNA primase" it is meant that the disclosed compounds substantially do not alter the activity of mammalian, preferably human, DNA primase.

Exemplary primases include, without being limited thereto, T7 (gene 4 protein) (P03692), T3 (gene 4 protein) (P20315), P4 (α protein) (PRBPP4), and T4 (gene 41 protein) (ADD42502).

In some embodiments, the inhibition of DNA primase substantially stops bacterial DNA replication and prevent bacterial infection.

In some embodiments, and without being bound by any particular mechanism, the disclosed compound inhibits T7 DNA primase.

In some embodiments, the disclosed compound or the composition is for use for treating a medical condition associated with the expression of DNA gyrase. In some embodiments, by "treating a medical condition associated with the expression of DNA gyrase" it is meant to refer to modulating DNA gyrase activity.

As used herein, the term "modulating" in reference to DNA primase or gyrase activity includes any measurable alteration, e.g., reduction or inhibition of DNA primase activity. In some embodiments, by "reduction" it is meant reducing 10%, 20%, 30%, 40%, 60%, 70%, 80%, 90%, or 99%, including any value and range therebetween, of the activity of the corresponding enzyme.

In some embodiments, "DNA gyrase" refers to a bacterial DNA gyrase.

In some embodiments, the disclosed compound or the composition is for use for selectively modulating bacterial DNA gyrase. In some embodiments, by "selectively reducing bacterial DNA gyrase" it is meant that the disclosed compounds substantially do not alter the activity of mammalian, preferably human, DNA gyrase.

In exemplary embodiments, the compounds for treating a medical condition associated with the expression of DNA gyrase are selected from Formulae IA2 and IA3 as denoted herein.

In exemplary embodiments, the compounds for reducing bacterial proliferation associated with the expression of DNA are selected from Formulae V and VI as denoted herein.

In some embodiments, the medical condition is associated with a pathogenic microorganism. In some embodiments, the pathogenic microorganism comprises DNA gyrase or primase.

According to an aspect of some embodiments of the present invention, there is provided a method of reducing DNA primase activity, the method comprising contacting the DNA primase with one or more of the herein disclosed compounds.

According to an aspect of some embodiments of the present invention, there is provided a method of inhibiting DNA primase, the method comprising contacting the DNA primase with one or more of the herein disclosed compounds.

According to an aspect of some embodiments of the present invention, there is provided a method of inhibiting DNA gyrase, the method comprising contacting the DNA gyrase with one or more of the herein disclosed compounds.

In some embodiments, the invention also provides a method for identifying compounds that modulate one or more from DNA primase and gyrase activity.

In some embodiments, the invention also provides a method for reducing one or more from DNA primase, or gyrase activity, contacting the disclosed compounds with a DNA primase or gyrase, respectively.

In some embodiments, the invention also provides a method for modulating one or more from DNA primase, or gyrase activity, contacting the disclosed compounds with a DNA primase or gyrase, respectively.

In some embodiments, there is provided a method for treating a subject afflicted with bacterial infection, comprising administering to the subject a pharmaceutically effective amount of one or more of the herein disclosed compounds in any embodiments thereof.

In some embodiments, there is provided a method for reducing bacterial load in a subject afflicted with bacterial infection, comprising administering to the subject a pharmaceutically effective amount of one or more of the herein disclosed compounds in any embodiments thereof.

In some embodiments, there is provided a method of reducing biofilm formation, the method comprising contacting the bacteria with one or more of the herein disclosed compositions in any embodiments thereof. In some embodiments, the method is further directed to inhibiting biofilm formation.

In some embodiments, there is provided a method of disrupting an existing biofilm, the method comprising contacting the existing biofilm with one or more of the herein disclosed compositions in any embodiments thereof.

In some embodiments, there is provided a method of killing bacteria, or inhibiting bacteria from reproducing, the method comprising contacting the bacteria with one or more of the herein disclosed compounds in any embodiments thereof.

In some embodiments, the contacting is affected in vivo. In some embodiments, the contacting is affected ex vivo.

Herein throughout, the phrase "pathogenic microorganism" is used to describe any microorganism which can cause a disease or disorder in a higher organism, such as mammals in general and a human in particular. The pathogenic microorganism may belong to any family of organisms such as, but not limited to prokaryotic organisms, Eubacterium, archaebacterium, eukaryotic organisms, yeast, fungi, algae, protozoan, and other parasites. Non-limiting examples of pathogenic microorganism are Staphylococcus aureus, Aquifex aeolicus Plasmodium falciparum and related malaria-causing protozoan parasites, Acanthamoeba and other free-living amoebae, Aeromonas hydrophila, Anisakis and related worms, Acinetobacter baumanii, Ascaris lumbricoides, Bacillus cereus, Brevundimonas diminuta, Campylobacter jejuni, Clostridium botulinum, Clostridium perfringens, Cryptosporidium parvum, Cyclospora cayetanensis, Diphyllobothrium, Entamoeba histolytica, certain strains of Escherichia coli, Eustrongylides, Giardia lamblia, Klebsiella pneumoniae, Listeria monocytogenes, Nanophyetus, Plesiomonas shigelloides, Proteus mirabilis, Pseudomonas aeruginosa, Salmonella, Serratia odorifera, Shigella, Staphylococcus aureus, Stenotrophomonas maltophilia, Streptococcus, Trichuris trichiura, Vibrio cholerae, Vibrio parahaemolyticus, Vibrio vulnificus and other vibrios, Yersinia enterocolitica, Yersinia pseudotuberculosis and Yersinia kristensenii.

As used herein, the terms "treating" and "treatment" include abrogating, substantially inhibiting, slowing or reversing the progression of a condition, substantially ameliorating clinical or aesthetical symptoms of a condition or substantially preventing the appearance of clinical or aesthetical symptoms of a condition.

The method of treatment, according to an embodiment of the present invention, may include the administration of an additional therapeutically active agent.

The disclosed compounds, alone or in combination thereof or with any another therapeutically active agent, can be designed and utilized to destroy pathological microorganisms, thereby treating medical condition(s) or disease(s) associated with a pathogenic microorganism. In some embodiments, the compounds of the present invention will exert a dual and possibly synergistic antimicrobial activity when in combination thereof or with any another therapeutically active agent.

Medical conditions associated with a pathogenic microorganism include infections, infestation, contaminations and transmissions by or of pathogenic microorganism. In general, a disease causing infection is the invasion into the tissues of a plant or an animal by pathogenic microorganisms. The invasion of body tissues by parasitic worms and other higher pathogenic organisms is commonly referred to as infestation.

Diseases caused by bacterial infections typically include, for example and without being limited thereto, actinomycosis, anthrax, aspergillosis, bacteremia, bacterial skin diseases, Bartonella infections, botulism, brucellosis, Burkholderia infections, Campylobacter infections, candidiasis, cat-scratch disease, Chlamydia infections, cholera, Clostridium infections, coccidioidomycosis, cryptococcosis, dermatomycoses, diphtheria, ehrlichiosis, epidemic louse borne typhus, Escherichia coli infections, Fusobacterium infections, gangrene, general infections, general mycoses, gonorrhea, gram-negative bacterial infections, gram-positive bacterial infections, histoplasmosis, impetigo, Klebsiella infections, legionellosis, leprosy, leptospirosis, Listeria infections, lyme disease, malaria, maduromycosis, melioidosis, Mycobacterium infections, Mycoplasma infections, necrotizing fasciitis, Nocardia infections, onychomycosis, ornithosis, pneumococcal infections, pneumonia, Pseudomonas infections, Q fever, rat-bite fever, relapsing fever, rheumatic fever, Rickettsia infections, Rocky-mountain spotted fever, Salmonella infections, scarlet fever, scrub typhus, sepsis, sexually transmitted bacterial diseases, staphylococcal infections, streptococcal infections, surgical site infection, tetanus, tick-borne diseases, tuberculosis, tularemia, typhoid fever, urinary tract infection, Vibrio infections, yaws, Yersinia infections, Yersinia pestis plague, zoonoses and zygomycosis.

As used herein, the term "preventing" in the context of antimicrobial, indicates that the growth rate of the microorganism cells is essentially nullified or is reduced by at least 20%, at least 30%, at least 40%, at least 50%, at least 60%, at least 70%, at least 80%, at least 90%, including any value therebetween, of the appearance of the microorganism in a comparable situation lacking the presence of the disclose compounds or a composition of matter containing same. Alternatively, preventing means a reduction to at least 15%, 10% or 5% of the appearance of the microorganism cells in a comparable situation lacking the presence of the disclosed compounds or a composition of matter containing same.

In some embodiments, the method comprises administering to the subject a pharmaceutically effective amount of one or more of the herein disclosed compounds or compositions.

In some embodiments, the method may further comprise administering an additional drug intended to treat an antibacterial infection.

It will be recognized that these embodiments are susceptible to various modifications and alternative forms well known to those of skill in the art.

Methods for determining a level of appearance of a microorganism cells are known in the art.

Pharmaceutical Composition

According to an aspect of embodiments of the invention there is provided a pharmaceutical composition comprising one or more compounds as described herein and a pharmaceutically acceptable carrier.

According to some embodiments of the invention, the composition is for use in the treatment of a medical condition associated with any disease, medical condition, or disorder as described herein throughout.

According to some embodiments of the invention, the composition is being packaged in a packaging material and identified in print, in or on the packaging material, for use in the treatment of a medical condition associated with any disease, medical condition, or disorder as described herein throughout.

In some embodiments, the composition comprises a compound at a concentration of 0.2 to 500 µM. In some embodiments, the composition comprises a compound at a concentration of 0.2 to 2 µM. In some embodiments, the composition comprises a compound at a concentration of 0.2 to 2 µM. In some embodiments, the composition comprises a compound at a concentration of 1 to 5 µM. In some embodiments, the composition comprises a compound at a concentration of 2 to 10 µM. In some embodiments, the composition comprises a compound at a concentration of 10 to 100 µM. In some embodiments, the composition comprises a compound at a concentration of 100 to 500 µM. According to some embodiments of the invention, the composition is being packaged in a packaging material and identified in print, in or on the packaging material, for use in the treatment of a medical condition associated with any disease, medical condition, or disorder as described herein throughout.

In some embodiments, there is provided a method of treating a medical condition associated with any disease, medical condition, or disorder as described hereinthroughout in a subject in need thereof, the method comprising administering to the subject a therapeutically effective amount of the compound or composition as described herein.

As used herein, the phrase "therapeutically effective amount" describes an amount of the compound being administered which will relieve to some extent one or more of the symptoms of the condition being treated.

The term "subject" (which is to be read to include "individual", "animal", "patient" or "mammal" where context permits) defines any subject, particularly a mammalian subject, for whom treatment is indicated. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters, guinea pigs, and so on.

In some embodiments, the subject is a human. In another embodiment, the subject is a human suffering from a bacterial infection. In some embodiments, the subject is a mammal. In some embodiments, the subject is a pet. In some embodiments, the subject is a farm animal.

According to an aspect of embodiments of the invention there is provided a use of any one of the compounds as described herein as a medicament.

According to an aspect of embodiments of the invention there is provided a use of any one of the compounds as described herein in the manufacture of a medicament for treating a medical condition associated with any disease, medical condition, or disorder associated with a bacterial infection.

The compounds described hereinabove may be administered or otherwise utilized either as is, or as a pharmaceutically acceptable salt, enantiomer, diastereomer, solvate, hydrate or a prodrug thereof.

The phrase "pharmaceutically acceptable salt" refers to a charged species of the parent compound and its counter ion, which is typically used to modify the solubility characteristics of the parent compound and/or to reduce any significant irritation to an organism by the parent compound, while not abrogating the biological activity and properties of the administered compound. The neutral forms of the compounds may be regenerated by contacting the salt with a base or acid and isolating the parent compound in a conventional manner. The parent form of the compound differs from the various salt forms in certain physical properties, such as solubility in polar solvents, but otherwise the salts are equivalent to the parent form of the compound for the purposes of the present invention. The phrase "pharmaceutically acceptable salts" is meant to encompass salts of the active compounds which are prepared with relatively non-toxic acids or bases, depending on the particular substituents found on the compounds described herein.

Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science, 1977, 66, 1-19). Certain specific compounds of the present invention contain both basic and acidic functionalities that allow the compound as described herein to be converted into either base or acid addition salts.

In some embodiments, the neutral forms of the compounds described herein are regenerated by contacting the salt with a base or acid and isolating the parent compounds in a conventional manner. The parent form of the compounds differs from the various salt forms in certain physical properties, such as solubility in polar solvents, but otherwise the salts are equivalent to the parent form of the compound for the purposes of the present invention.

The term "prodrug" refers to an agent, which is converted into the active compound (the active parent drug) in vivo. Prodrugs are typically useful for facilitating the administration of the parent drug. The prodrug may also have improved solubility as compared with the parent drug in pharmaceutical compositions. Prodrugs are also often used to achieve a sustained release of the active compound in vivo.

In some embodiments, the compounds described herein possess asymmetric carbon atoms (optical centers) or double bonds; the racemates, diastereomers, geometric isomers and individual isomers are encompassed within the scope of the present invention.

As used herein and in the art, the term "enantiomer" describes a stereoisomer of a compound that is superposable with respect to its counterpart only by a complete inversion/reflection (mirror image) of each other. Enantiomers are said to have "handedness" since they refer to each other like the right and left hand. Enantiomers have identical chemical and physical properties except when present in an environment which by itself has handedness, such as all living systems.

In some embodiments, the compounds described herein can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

The term "solvate" refers to a complex of variable stoichiometry (e.g., di-, tri-, tetra-, penta-, hexa-, and so on), which is formed by a solute (the conjugate described herein) and a solvent, whereby the solvent does not interfere with the biological activity of the solute. Suitable solvents include, for example, ethanol, acetic acid and the like.

The term "hydrate" refers to a solvate, as defined hereinabove, where the solvent is water.

In some embodiments, the "pharmaceutical composition" refers to a preparation of one or more of the compounds described herein (as active ingredient), or physiologically acceptable salts or prodrugs thereof, with other chemical components including, but not limited to, physiologically suitable carriers, excipients, lubricants, buffering agents, antibacterial agents, bulking agents (e.g., mannitol), antioxidants (e.g., ascorbic acid or sodium bisulfite), anti-inflammatory agents, anti-viral agents, chemotherapeutic agents, anti-histamines and the like.

In some embodiments, the purpose of a pharmaceutical composition is to facilitate administration of a compound to a subject. The term "active ingredient" refers to a compound, which is accountable for a biological effect.

The terms "physiologically acceptable carrier" and "pharmaceutically acceptable carrier", which may be interchangeably used, refer to a carrier or a diluent that does not cause significant irritation to an organism and does not abrogate the biological activity and properties of the administered compound.

Herein the term "excipient" refers to an inert substance added to a pharmaceutical composition to further facilitate administration of a drug. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences" Mack Publishing Co., Easton, Pa., latest edition, which is incorporated herein by reference.

In some embodiments, pharmaceutical compositions for use in accordance with the present invention thus may be formulated in conventional manner using one or more pharmaceutically acceptable carriers comprising excipients and auxiliaries, which facilitate processing of the compounds into preparations which can be used pharmaceutically. Proper formulation is dependent upon the route of administration chosen. The dosage, as described and specified herein, may vary depending upon the dosage form employed and the route of administration utilized. The exact formulation, route of administration and dosage can be chosen by the individual physician in view of the patient's condition (see e.g., Fingl et al., 1975, in "The Pharmacological Basis of Therapeutics", Ch. 1 p. 1).

In some embodiments, the pharmaceutical composition may be formulated for administration in either one or more of routes depending on whether local or systemic treatment or administration is of choice, and on the area to be treated. As further described hereinthroughout, administration may be done orally, dentally, by inhalation, or parenterally, for example by intravenous drip or intraperitoneal, subcutaneous, intramuscular or intravenous injection, or topically (including ophtalmically, vaginally, rectally, intranasally).

Formulations for topical and/or dental administration may include but are not limited to lotions, ointments, gels, creams, suppositories, drops, liquids, sprays and powders. Conventional pharmaceutical carriers, aqueous, powder or oily bases, thickeners and the like may be necessary or desirable.

Compositions for oral administration include powders or granules, suspensions, dental compositions, or solutions in water or non-aqueous media, sachets, pills, caplets, capsules or tablets. Thickeners, diluents, flavorings, dispersing aids, emulsifiers, or binders may be desirable.

Formulations for parenteral administration may include, but are not limited to, sterile solutions which may also contain buffers, diluents and other suitable additives. Slow release compositions are envisaged for treatment.

The amount of a composition to be administered will, of course, be dependent on the subject being treated, the severity of the affliction, the manner of administration, the judgment of the prescribing physician, etc.

The pharmaceutical composition may further comprise additional pharmaceutically active or inactive agents such as, but not limited to, an antibacterial agent, an antioxidant, a buffering agent, a bulking agent, a surfactant, an anti-inflammatory agent, an anti-viral agent, a chemotherapeutic agent and anti-histamine.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

In some embodiments, the method comprises administering to the subject a pharmaceutically effective amount of one or more of the herein disclosed compounds or compositions (e.g., compounds having one of the general "Formulae I, II or III" described hereinabove, in any embodiment thereof).

In some embodiments, the method may further comprise administrating an additional drug intended to treat an antibacterial infection.

It will be recognized that these embodiments are susceptible to various modifications and alternative forms well known to those of skill in the art.

Definitions

As used herein, the term "alkyl" describes an aliphatic hydrocarbon including straight chain and branched chain groups. Preferably, the alkyl group has 21 to 100 carbon atoms, and more preferably 21-50 carbon atoms. Whenever a numerical range; e.g., "21-100", is stated herein, it implies that the group, in this case the alkyl group, may contain 21 carbon atom, 22 carbon atoms, 23 carbon atoms, etc., up to and including 100 carbon atoms. In the context of the present invention, a "long alkyl" is an alkyl having at least 20 carbon atoms in its main chain (the longest path of continuous covalently attached atoms). A short alkyl therefore has 20 or less main-chain carbons. The alkyl can be substituted or unsubstituted, as defined herein.

The term "alkyl", as used herein, also encompasses saturated or unsaturated hydrocarbon, hence this term further encompasses alkenyl and alkynyl.

The term "alkenyl" describes an unsaturated alkyl, as defined herein, having at least two carbon atoms and at least one carbon-carbon double bond. The alkenyl may be substituted or unsubstituted by one or more substituents, as described hereinabove.

The term "alkynyl", as defined herein, is an unsaturated alkyl having at least two carbon atoms and at least one carbon-carbon triple bond. The alkynyl may be substituted or unsubstituted by one or more substituents, as described hereinabove.

The term "cycloalkyl" describes an all-carbon monocyclic or fused ring (i.e. rings which share an adjacent pair of carbon atoms) group where one or more of the rings does not have a completely conjugated pi-electron system. The cycloalkyl group may be substituted or unsubstituted, as indicated herein.

The term "aryl" describes an all-carbon monocyclic or fused-ring polycyclic (i.e. rings which share adjacent pairs of carbon atoms) groups having a completely conjugated pi-electron system. The aryl group may be substituted or unsubstituted, as indicated herein.

The term "alkoxy" describes both an —O-alkyl and an —O-cycloalkyl group, as defined herein.

The term "aryloxy" describes an —O-aryl, as defined herein.

Each of the alkyl, cycloalkyl and aryl groups in the general formulas herein may be substituted by one or more substituents, whereby each substituent group can independently be, for example, halide, alkyl, alkoxy, cycloalkyl, alkoxy, nitro, amine, hydroxyl, thiol, thioalkoxy, thiohydroxy, carboxy, amide, aryl and aryloxy, depending on the substituted group and its position in the molecule. Additional substituents are also contemplated.

The term "halide", "halogen" or "halo" describes fluorine, chlorine, bromine or iodine.

The term "haloalkyl" describes an alkyl group as defined herein, further substituted by one or more halide(s).

The term "haloalkoxy" describes an alkoxy group as defined herein, further substituted by one or more halide(s).

The term "hydroxyl" or "hydroxy" describes a —OH group.

The term "thiohydroxy" or "thiol" describes a —SH group.

The term "thioalkoxy" describes both an —S-alkyl group, and a —S-cycloalkyl group, as defined herein.

The term "thioaryloxy" describes both an —S-aryl and a —S-heteroaryl group, as defined herein.

The term "amine" describes a —NR'R" group, with R' and R" as described herein.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine.

The term "heteroalicyclic" or "heterocyclyl" describes a monocyclic or fused ring group having in the ring(s) one or more atoms such as nitrogen, oxygen and sulfur. The rings may also have one or more double bonds. However, the rings do not have a completely conjugated pi-electron system. Representative examples are piperidine, piperazine, tetrahydrofurane, tetrahydropyrane, morpholino and the like.

The term "carboxy" or "carboxylate" describes a —C(=O)—OR' group, where R' is hydrogen, alkyl, cycloalkyl, alkenyl, aryl, heteroaryl (bonded through a ring carbon) or heteroalicyclic (bonded through a ring carbon) as defined herein.

The term "carbonyl" describes a —C(=O)—R' group, where R' is as defined hereinabove.

The above-terms also encompass thio-derivatives thereof (thiocarboxy and thiocarbonyl).

The term "thiocarbonyl" describes a —C(=S)—R' group, where R' is as defined hereinabove.

A "thiocarboxy" group describes a —C(=S)—OR' group, where R' is as defined herein.

A "sulfinyl" group describes an —S(=O)—R' group, where R' is as defined herein.

A "sulfonyl" or "sulfonate" group describes an —S(=O)2-R' group, where Rx is as defined herein.

A "carbamyl" or "carbamate" group describes an —OC(=O)—NR'R" group, where R' is as defined herein and R" is as defined for R'.

A "nitro" group refers to a —NO$_2$ group.

The term "amide" as used herein encompasses C-amide and N-amide.

The term "C-amide" describes a —C(=O)—NR'R" end group or a —C(=O)—NR'-linking group, as these phrases are defined hereinabove, where R' and R" are as defined herein.

The term "N-amide" describes a R'C(=O)—NR"— end group or a R'C(=O)—N— linking group, as these phrases are defined hereinabove, where R' and R" are as defined herein.

The term "carboxylic acid derivative" as used herein encompasses carboxy, amide, carbonyl, anhydride, carbonate ester, and carbamate.

A "cyano" or "nitrile" group refers to a —C≡N group.

The term "azo" or "diazo" describes an —N=NR' end group or an —N=N— linking group, as these phrases are defined hereinabove, with R' as defined hereinabove.

The term "guanidine" describes a —R'NC(=N)—NR"R'" end group or a —R'NC(=N)—NR"— linking group, as these phrases are defined hereinabove, where R', R" and R'" are as defined herein.

As used herein, the term "azide" refers to a —N$_3$ group.

The term "sulfonamide" refers to a —S(=O)2-NR'R" group, with R' and R" as defined herein.

The term "phosphonyl" or "phosphonate" describes an —O—P(=O)(OR')2 group, with R' as defined hereinabove.

The term "phosphinyl" describes a —PR'R" group, with R' and R" as defined hereinabove.

The term "alkaryl" or "alkylaryl" describes an alkyl, as defined herein, which substituted by an aryl, as described herein. An exemplary alkaryl is benzyl.

The term "heteroaryl" describes a monocyclic or fused ring (i.e. rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted by one or more substituents, as described hereinabove. Representative examples are thiadiazole, pyridine, pyrrole, oxazole, indole, purine and the like.

As used herein, the terms "halo" and "halide", which are referred to herein interchangeably, describe an atom of a halogen, that is fluorine, chlorine, bromine or iodine, also referred to herein as fluoride, chloride, bromide and iodide.

The term "haloalkyl" describes an alkyl group as defined above, further substituted by one or more halide(s).

General

As used herein the term "about" refers to ±10%.

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Example 1

Identification of DNA Primase Inhibitors

Materials and Methods

Figure 1:
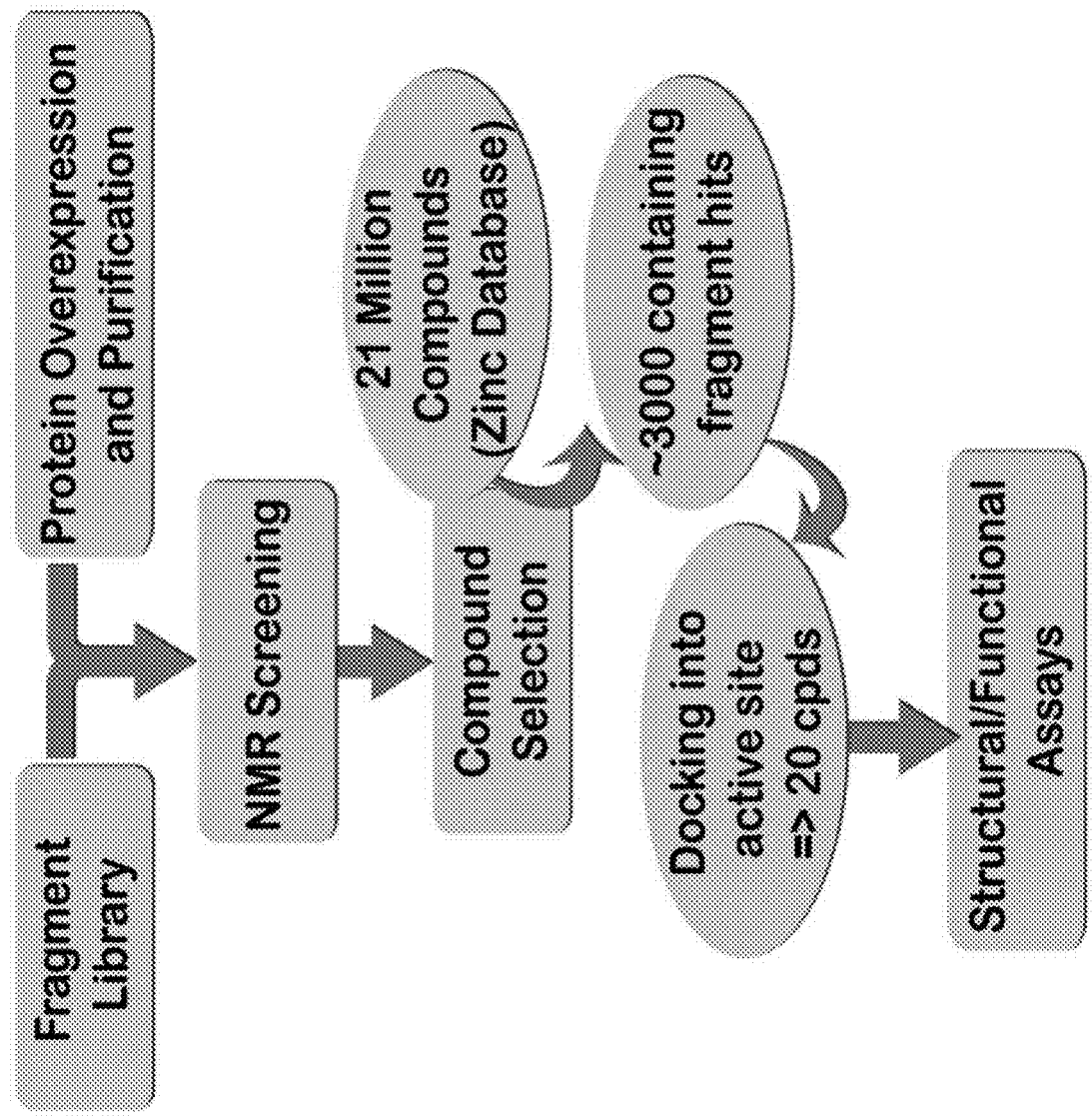

General concept: Reference is made to FIG. 1 summarizing the Fragment based virtual screening, an approach combining NMR-fragment based screening with virtual screening to select inhibitors (compounds, "cpds") against e.g., phage T7 DNA primase. Using 1D NMR (STD) and a fragment library, allows identifying scaffolds that bind T7 DNA primase. These scaffolds were used as a filter to select larger compounds with drug-like properties from a database of 21 million compounds (ZINC). Thousands of compounds for each scaffold were docked to the active site of T7 DNA primase (pdb code: 1nui) and hits were ranked based on the binding energy. Several candidate compounds were selected and tested for their ability to inhibit T7 DNA replication.

The FBVS combines a spectroscopic assay (STD spectroscopy) was introduced with an in-silico approach. Its computational component comprised the virtual filtration of a small molecule database followed by the docking of the potential small molecule inhibitors to the crystal structure of T7 primase. Not only did this approach allowed to find several lead compounds for T7 primase inhibition, it also showed a high hit rate: of the 16 compounds ordered for testing, about half showed primase inhibition activity. This approach, which is not only fast but also cost effective, is a promising method for identifying the inhibitors of protein targets that are not amenable to high throughput screening.

The fragment based screening approach disclosed here allows to rationally design drug like inhibitors (that contain small fragments) to the primase. However, in contrast to conventional fragment-based screening, which requires a subsequent medicinal chemistry step to grow the hit molecules, FBVS eliminates the need for that step early on and increases the chances of successfully identifying larger molecules containing the fragment hits.

Protein expression and purification: Chemicals were from Sigma. ATP and CTP were from Roche Molecular Biochemicals. dNTPs were from USB Corp. Pre-made gels (10-20% linear gradients) were from BioRad (Hercules, Calif.). T7 gp5, gp4, E. coli trx were overproduced and purified. M13 ssDNA was prepared as described in J. Biol. Chem. 261, 15208-16 (1986). [$\gamma$-$^{32}$P] dATP (800 Ci/mmol), [$\alpha$-$^{32}$P] CTP, and dTTP (800 Ci/mmol) were from Perkin Elmer.

Protein expression and purification: Proteins and Reagents. All chemical reagents were of molecular biology grade (Sigma); ATP and CTP (Roche Molecular Biochemicals). dNTPs and ddNTPs were purchased from USB Corp. Premade gels (10-20% linear gradients) used for SDS-PAGE and Precision Plus Protein prestained standards were purchased from BioRad (Hercules, Calif.). T7 primase domain (residue: 1-271) was over-produced and purified using metal free buffers as previously described in *Mol Cell* 11, 1349-60 (2003). T7 gp5 and *E. Coli* trx were overproduced and purified as described in J. Biol. Chem. 262, 16224-32 (1987). Gp4 was overproduced and purified as described in J. Biol. Chem. 272, 18425-33 (1997). M13 ssDNA was prepared as described in J. Biol. Chem. 261, 15208-16 (1986). [$\alpha$-$^{32}$P]-CTP (800 Ci/mmol) was purchased from Perkin Elmer.

Virtual screening: The hits determined by NMR were used to identify compounds with at least 70% similarity from the ZINC database Irwin, J. J. J Chem. Inf. Model (2012). Virtual screening was performed to identify molecules that could bind in the active site of T7 DNA primase and inhibit DNA replication. Docking of all compounds downloaded from the ZINC database was performed using Autodock4.2.3. PDB files of the receptor (T7 primase) and the ligands (compounds) were prepared prior to docking.

The search grid was centered in the active site of T7 primase with a grid spacing of 0.375 Å and 110×108×126 points. The default parameters were used except for the following modified parameters: ga_num_evals=1750000, ga_pop_size=150, and ga_run=100.

Primase dependent DNA synthesis: RNA primers made by gp4A were extended by gp5/trx. The reaction mixture contained 10 nM M13 ssDNA, 0.3 mM dNTPs, 0.1 µCi [$\alpha$-$^{32}$P] dCTP, 20 nM gp5/trx, 200 nM monomeric gp4A, and 350 µM of each compound. The reaction was incubated for 45 min at 37° C. Reaction was terminated and amount of DNA synthesis was determined as described in DNA polymerase assay.

DNA polymerase assay: DNA polymerase activity was measured in a reaction containing 5 nM gp5/trx, 20 nM M13 ssDNA annealed to a 24mer primer, 40 mM Tris-HCl (pH 7.5), 10 mM MgCl$_2$, 10 mM DTT, 50 mM potassium glutamate, 0.25 mM dTTP, dGTP, dCTP, [$\alpha$-$^{32}$P] dATP (5 cpm/pmol) and 500 µM of each compound. The reaction was incubated at 37° C. for 20 min and terminated by the addition of EDTA to a final concentration of 40 mM. Aliquots of the reaction were spotted on DE-81 filters (Whatman), washed three times with excess of 0.3 M ammonium formate (pH 8.0), and the radioactivity retained on the filters measured.

Oligoribonucleotide Synthesis Assay: Oligoribonucleotides were synthesized by DNA primase, product was measured as described in J Biol Chem 272, 5943-51 (1997) and in J Biol Chem 266, 23240-50 (1991), in reactions containing various concentrations (1.1, 3.3, and 10 µM) of gene 4 primase domain. Standard 10 µL reaction contained 5 µM of DNA template (5'-GGGTCA$_{10}$-3'), 200 µM ATP, 200 µM [$\alpha$-$^{32}$P]-CTP, and primase domain in a buffer containing 40 mM Tris-HCl (pH 7.5), 10 mM MnCl$_2$, 10 mM DTT, and 50 mM potassium glutamate. After incubation at room temperature for 20 minutes, the reaction was terminated by adding an equal volume of sequencing buffer containing 98% formamide, 0.1% bromophenolblue, and 20 mM EDTA. The samples were loaded onto 25% polyacrylamide sequencing gel containing 3 M urea and visualized using autoradiography.

Sample preparation: For the expression of unlabeled proteins, the primase domain of the bacteriophage T7 gene 4 product (1-271) was expressed in *E. coli* Bl21(DE3) containing pETg4P as reported in Proc Natl Acad Sci USA 95, 7957-62 (1998).

For expression of isotopically enriched proteins, a starter culture was used to inoculate 2 liters of M9 medium containing 50 µg/mL kanamycin, 1 g $^{15}$N—NH$_4$Cl, and 2 g $^{13}$C-glucose or 2 g $^2$H,$^{13}$C-glucose. The M9 was made up in D$_2$O for expression of perdeuterated proteins. When the culture optical density (600 nm) reached approximately 0.8, the culture was induced for protein overexpression with 0.3 mM isopropyl-β-D-thiogalactopyranoside (IPTG) for 16 to 24 h at 16° C. Cell pellet was resuspended in buffer A (50 mM Tris-HCl pH=7.5, 1 mM EDTA, 1 mM DTT), 100 mM NaCl, 0.25 mg/ml lysozyme and 1 mM PMSF and incubated in ice for 1 h.

After four cycles of freeze-thaw streptomycin sulfate was added to a concentration of 1%. After centrifugation at 15,000×g for 30 min supernatant was diluted with Buffer A (no salt) fivefold and loaded onto DEAE sepharose (packed in AP-5, Waters, N.J.) and washed with 200 mL of 50 mM Tris-HCl. Primase domain was eluted using linear gradient of Buffer A from no salt to 1M NaCl. Primase fractions were combined and ammonium sulfate was added (0.361 g/ml). The precipitant was collected by centrifugation (15,000×g for 30 min), dissolved in 10 mL buffer A, loaded onto a sephacryl S-200HR column and eluted using Buffer A. The fractions containing the primase domain were combined and applied to a 5-ml HiTrap Blue affinity column. The column was washed with excess amount of buffer A and the primase was eluted using a linear gradient of NaCl (0-1M) in Buffer A. The pure protein was dialyzed against buffer B (50 mM KH$_2$PO$_4$/K$_2$HPO$_4$ pH=7, 1 mM DTT) and concentrated to 0.4 mM.

NMR experiments—Fragment Based Screening: T7 primase was screened against the Maybridge Ro3 Diversity Fragment Library containing 1000 compounds using STD spectroscopy. Samples for 1D ligand-observed NMR studies contained 5 µM T7 primase in 50 mM phosphate buffer in D$_2$O and 10 compounds, resulting in a total of 100 samples. NMR spectra were recorded on a Bruker Avance 500 MHz equipped with a TXO cryoprobe with Z gradient and a NMR-CASE sample changer at 298 K. Ligand binding was probed using a saturation transfer difference pulse program. Saturation was achieved using on-resonance irradiation at 0 ppm with a train of Wurst pulses for a total saturation time of 1.5 s. Off resonance irradiation was centered at 40 ppm.

Spectra were acquired with a sweep width of 8012.8 Hz, 8192 data points and 224 scans. Active compounds were identified by comparing the STD spectra with the corresponding reference spectra using the MestreNova software. Any compound with reduced peak intensities was considered a hit and ranked according to the percentage of intensity decrease and the number of affected peaks per compound.

[$^1$H,$^{15}$N]-TROSY HSQC titration spectra of 15N,D T7 DNA primase with selected fragment molecules and compounds 1, 12, 13, 15, 17, ATP, and DNA were recorded at 25° C. on a Bruker DMX 800 MHz spectrometer equipped with TXI cryoprobes with Z gradient. Data were processed and analyzed using NMRPipe (Journal of Biomolecular NMR 6, 277-293 (1995)) and NMRView (Journal of Biomolecular Nmr 4, 603-614 (1994)).

NMR experiments—Backbone resonance assignments: Spectra were acquired at 298.15 K with 700 μM protein samples in 25 mM KH2PO4/K2HPO4, pH=7.2, 150 mM NaCl, 1 mM DTT. Traditional TROSY-based backbone triple resonance experiments (HNCA/HNCOCA, HNCO/HNCACO, HNCACB) were conducted on a 15N,13C-perdeuterated sample to assign the backbone chemical shifts. The spectra were recorded on a Varian 600 MHz spectrometer equipped with cryogenically cooled probe. Non Uniform Sampling was used in all the triple resonance experiments where 12% of the indirect dimension grid was sampled and the spectrum was reconstructed using hmsIST (J. Biomol. NMR 52, 315-27 (2012)) and NMRPipe (J. Biomol. NMR 6, 277-93 (1995)). The resulting spectra were visualized and analyzed using CARA (Swiss Federal Institute of Technology Zürich (ETH Zürich), Steinberg, Switzerland 2004/2005).

Example 2

Identification of DNA Primase Inhibitors

Results

Bacterial DnaG primase synthesizes RNA primers that are used by DNA polymerase in lagging strand synthesis during DNA replication. Owing to the stark differences between the human and bacterial primases, DnaG primase is a target for drug discovery. Here, the development of small molecule inhibitors of DnaG using the structurally similar primase domain of the bacteriophage T7 gene 4 protein as a model for the bacterial primase is utilized. The structure of bacterial DnaG is similar to that of T7 DNA primase, part of the fused helicase-primase gp4 of bacteriophage T7. The DNA polymerase α-primase complex from humans consists of four subunits. The p180 subunit is polymerase α, p58 and p49 comprise the primase, and p78 is the fourth, tightly bound subunit.

To find compounds that do not bind at high affinity but that have potential to become successful leads, a platform for lead discovery has been developed, comprising several complementary steps: (1) fragment based screening by STD spectroscopy of a small molecule library (Ro3), (2) hit optimization by virtual screening and the generation of a new set of drug-like compounds (Ro5), each of which contains a small molecule found in step 1, (3) docking of the drug-like compounds to the active site of T7 primase and selection of the compounds that will undergo functional and structural assays with the target T7 primase, and (4) further development of lead compounds.

Fragment Based Virtual Screening (FBVS)—A combined screening approach: Growing a fragment molecule into a larger molecule that possesses drug like properties is the bottleneck in fragment-based drug design approaches. Using the Maybridge Ro3 fragment library containing 1000 fragments, 100 NMR samples were prepared, each containing a mixture of 10 fragments and 50 μM T7 primase.

Ten fragments were used per each NMR sample to significantly minimize NMR time. The 10 fragments were chosen to show minimal overlap of their 1H chemical shift to allow easy identification of the shifts. The 1D saturation transfer difference spectra of these samples were measured, and fragments that exhibited saturation transfer (evident by a decrease in the peak intensity) were identified.

Hits were ranked based on the number of peaks in the 1H-NMR spectra with decreased intensities. The small molecule fragments indole and 2H-chromene-3-carbothioamide (see FIGS. 2A-B) exhibited the strongest binding that, correspondingly, was reflected in the largest decreases in NMR peak intensities (considering the total change in intensity and also the number of affected peaks).

Hits were validated by measuring the [15N,1H] HSQC spectra of 15N,D-T7 primase and then evaluating the chemical shift perturbations of the backbone amide resonances upon the addition of the small fragment molecules (see FIGS. 2A-B). This validation also ensures that the change in peak intensities in the 1D spectra was not a result of additive effects of several fragments.

Lead optimization and candidate selection: Hits from fragment-based screening are commonly optimized by creating larger compounds with better binding properties that usually involves medicinal chemistry.

To eliminate the need for a medicinal chemistry phase during the early steps of lead optimization, virtual screening was used, where the structure of the small molecule fragment binder found by STD spectroscopy was used as a constraint for the next search procedure. The rapidly growing ZINC database was searched, which contains the structures of over 100 million compounds, for those with at least 70% similarity to the fragment molecules identified by STD spectroscopy.

The two fragment molecules ranked highest by the fragment based screening—indole and 2H-chromene-3-carbothioamide—were used for this step of virtual filtration. The database search yielded approximately 3000 compounds per scaffold. Then the docking software AutoDock (J. Comput. Chem. 30, 2785-91 (2009)) was used to dock these compounds into the active site of T7 primase using its available crystal structure (pdb code 1nui (Mol. Cell 11, 1349-60 (2003)). The compounds were then ranked based on their ΔG predicted binding energy values. The highest-ranking compounds that contained indole or 2H-chromene-3-carbothioamide were obtained from the ZINC database for functional and structural assays with the target T7 primase.

FIGS. 3A-B present chemical structures of 16 small molecules obtained by virtual filtration using the ZINC database and high-throughput docking using AutoDock. The two subsets are based on the scaffolds obtained by STD spectroscopy: 2H-chromene-3-carbothioamide and indole (indicated in grey).

Small molecules that inhibit the concerted activity of primase and DNA polymerase: To evaluate the ability of the small molecule candidates to inhibit the primase-dependent replication of the lagging strand of bacteriophage DNA, an overall assay that involved the concerted activity of DNA polymerase (gene product 5 and E. coli thioredoxin, gp5/trx) and the helicase-primase (gene product 4, gp4, full-length) was run. In bacteriophage T7, lagging strand DNA synthesis involves interactions between gp5/trx and gp4. Full-length gp4 is required for the synthesis of oligoribonucleotides to initiate the synthesis of Okazaki fragments.

To examine the effect of 350 µM of each small molecule on the synthesis of primers and their transfer to gp5/trx, M13 ssDNA for the synthesis of oligoribonucleotides by the primase and their extension by gp5/trx was used (FIG. 4b, inset). To initiate DNA synthesis, the primase must first synthesize tetraribonucleotides on the DNA and then transfer them to gp5/trx. In addition to the four dNTPs, ATP and CTP were also provided, and the primers that were synthesized included pppACCC, pppACAC, and pppACCA.

Inhibition of the primase activity of gp4 halts RNA primer formation process, thereby preventing subsequent DNA polymerase activity. FIG. 4B and FIGS. 5A-C shows that primase dependent DNA synthesis decreases by up to fourfold with the addition of five small molecules, including (2E)-3-(6-chloro-2H-chromen-3-yl)acrylic acid (compound 1), 9-Nitro-7,12-dihydroindolo-[3,2-d][1]benzazepin-6(5)-one (compound 12), 3-[2-(ethoxycarbonyl)-5-nitro-1H-indol-3-yl]propanoic acid (compound 13), N-(1,3-benzodioxol-5-yl)-7-nitro-1H-indole-2-carboxamide (compound 15), and 7-nitro-1H-indole-2-carboxylic acid (compound 17), whose chemical structures are presented in FIG. 4A.

The Table in FIG. 6A presents the inhibitory effect of various small molecules on primase-dependent DNA synthesis mediated by gp5/trx and gene 4 helicase (gp4A). The standard reaction contained the ssM13 DNA template (10 nM), 0.3 mM dATP, dGTP, dCTP and [$\alpha$-$^{32}$P] dTTP (0.1 mCi), 10 nM gp5/trx, 200 nM monomeric concentrations of gp4B and 250 µM of small molecule inhibitors. After incubation for 30 min at 37° C., the level of RNA synthesis was determined based on the amount of [$\alpha$-$^{32}$P] dTTP incorporated into DNA.

FIG. 6B shows the effect of small molecule inhibitors on oligonucleotide synthesis by DNA primase. The standard reaction contained the oligonucleotide 5'-GGGTCA$_{10}$-'3 containing the primase recognition sequence, 200 mM [$\alpha$-$^{32}$P]-CTP and ATP, and 250 µM small molecule inhibitors in a buffer containing 40 mM Tris-HCl (pH 7.5), 10 mM MnCl$_2$, 10 mM DTT, and 50 mM potassium glutamate. The quenched samples were loaded onto 25% polyacrylamide sequencing gel containing 3M urea and visualized using autoradiography.

Small molecules that inhibit primase activity: to catalyze the synthesis of short RNA primers, T7 primase requires DNA with a primase recognition site, ATP and CTP, and a buffer containing divalent metal ions. The effect of each of the five small molecules found using FBVS approach as described above on RNA primer synthesis by the T7 primase was examined. The primase domain catalyzed the synthesis of the diribonucleotide pppAC on a DNA template containing the 5'-GTC-3' primase recognition site. Diribonucleotide synthesis was examined in the presence of each of the five small molecules found to inhibit the concerted activity of primase and polymerase (FIG. 4B). The reaction conditions involved incubating the T7 primase (for 30 min at 37° C.) with an oligonucleotide containing a primase recognition sequence, [$\alpha$-$^{32}$P]-CTP and ATP, and adding each small molecule in steadily increasing amounts. The radioactively labeled oligoribonucleotides were separated on a denaturing polyacrylamide gel, and radioactivity was measured on an autoradiogram. The amounts of RNA-primed DNA syntheses were determined by measuring the incorporation of dTMP (see Methods). The error bars were derived from three independent experiments.

The results further show that inhibition of the specific activity of the primase increased with increasing amounts of the small molecules (FIG. 5C). Curve fitting was performed using nonlinear four parameter logistics to explore features of small molecule binding to the enzyme.

The reaction conditions involve incubating the primase domain with an oligonucleotide containing a primase recognition sequence. In this assay, the DNA template containing the primase recognition site 5'-GTCA$_{10}$-3' enables the synthesis of only diribonucleotides pppAC. The reaction also contained [$\alpha$-$^{32}$P] CTP, ATP, and increasing amounts of the tested compounds (1.1, 3.3, and 10 µM). After incubation, the radioactive products were analyzed by electrophoresis through 25% polyacrylamide gel containing 3 M urea and visualized using autoradiography.

Values for IC$_{50}$ and Hill coefficient were extracted (FIGS. 5B-C). Data for compounds 1 and 13 were not sufficient for the analysis therefore IC$_{50}$ values and Hill coefficients were excluded. Overall, IC$_{50}$ for those molecules were in the sub-millimolar range. Hill coefficient for compound 12 present highest value presumably due to stronger binding of the molecule to the enzyme.

Structural analysis of inhibitor-primase interactions: To characterize the binding of the compounds identified using FBVS, the [$^{15}$N, $^1$H]-TROSY-HSQC spectra of $^{15}$N- and D-labeled T7 primase in the presence of the selected lead compounds (FIGS. 7A-B) were measured. After the addition of compounds 1, 13, and 17 to T7 primase, a significant chemical shift perturbations were observed compared to those obtained for the free T7 primase. Relative to the initial scaffold alone, those shifts were more pronounced, which indicates stronger binding interactions. In addition, chemical shift perturbations upon the addition of DNA and ATP/CTP to the T7 primase domain confirmed that all three compounds bind to the active site. Moreover, the presence of several cross peaks among the three compounds indicates that they exploit a similar binding mechanism. Compounds 12 and 15, whose polar dissolution values were the lowest from among the five inhibitors, were not able to achieve the concentrations needed for the protein-NMR experiments.

To unravel the binding site of T7 primase inhibitors, the resonances to the T7 primase backbone were assigned as described herein. With the exception of the zinc-binding domain, 70% of the chemical shifts of the T7 primase have been assigned to their corresponding residues. Assignment of the NMR peaks to the protein residues allows to identify the amino acid residues situated in the proximity of the active site that mediate small molecule inhibitor binding (FIG. 7B). Protein stability was severely impaired if the six amino acid residues at the binding site—Ala(80), Ser(87), Glu(89), Val(101), Met(105), Tyr(106)—are substituted altogether with Ala (except Ala(80), which was substituted with Gly).

FIG. 8A shows the amino acid residues that mediate the binding of each of the three small molecule inhibitors [(2E)-3-(6-chloro-2H-chromen-3-yl)acrylic acid (compound 1); 3-[2-(ethoxycarbonyl)-5-nitro-1H-indol-3-yl]propanoic acid (compound 13); 7-nitro-1H-indole-2-carboxylic acid (compound 17)].

Indeed, for each of the three compounds, the mechanism of binding to the active site cleft is similar but not identical, and the amino acids involved overlap slightly, such that Val(101), Met(105), and Tyr (106) mediate the binding of all three compounds (FIG. 8A).

All three of the small molecules bind to the primase active site and are expected to interfere with the binding to the substrate (ribonucleotide tri-phosphates) or to the DNA template. Indeed, substituting two of the amino acid residues that mediate the binding of all three compounds [Val(101)

and Met(105)] with Ala inactivated the primase (FIGS. 8B-C), an outcome that is indicative of the central roles these two amino acid residues play in primer synthesis. This specific binding location represents a potential route to prevent bacteria from evolving into a resistant strain: any adaptive mutation driven by inhibitor binding would completely disrupt primase activity, killing the bacteria as a result.

Taken together, functional assays for primase generate weak readout signals, and therefore, are not easily adapted to high throughput screening. The T7 primase is a useful model to study bacterial primases since: (i) it shares high structural similarity with bacterial primases, (ii) it is highly expressed, (iii) it has been studied, and (iv) its crystal structure is known. NMR HSQC perturbations were assigned to the amino acid sequences of the primase, which enabled us to identify the amino acid residues that mediate small molecule inhibitor binding.

Example 3

Bacterial Growth Assay

Bacterial strains and growth media: Msmg cells $mc^2155$ (wild type), containing Hygromycin resistance gene and transcriptional red fluorescent protein gene (mCherry), were grown in Middlebrook 7H9 broth (Fluka) liquid medium supplemented with glycerol (0.4%, v/v) and Tween-80 (0.05%, v/v) (7H9++ liquid medium). Solid medium was composed of Middlebrook 7H10 agar (Difco) and 0.4% (v/v) glycerol (7H10+ agar solid medium). Hygromycin was added to both liquid and solid media to a final concentration of 50 µg/mL.

The experiments were conducted under strictly sterile conditions. All instruments, materials and mediums involved were sterilized before use. Experimental procedures were performed in a biological hood with a laminar flow.

Bacterial growth of Msmg culture: Msmg culture was first inoculated onto 7H10+ agar plate (medium components are described above) containing 50 µg/mL hygromycin and incubated at 30° C. for approximately four days. The primary liquid culture was prepared by transferring numerous colonies from a previously inoculated 7H10+ agar plate into 10 mL of 7H9++ liquid medium containing 50 µg/mL hygromycin. Cells were incubated overnight (~16 hours) at 30° C. with shaking (200 rpm). The secondary culture was prepared by transferring 1 mL of Msmg primary culture into 50 mL 7H9++ liquid medium (1:50 ratio, v/v) supplemented with 50 µg/mL hygromycin. Again, cells were grown overnight at 30° C. with shaking (200 rpm) to mid-log phase ($OD_{600}$~0.5). Then the culture was diluted to $OD_{600}$=0.025, dispensed in wells of Thermo Scientific™ Nunc™ F96 MicroWell™ black polystyrene plate and treated with different small molecule inhibitors at concentration of 250 µM. The plate was incubated at 30° C. with continuous orbital shaking (567 cpm) over the course of 20 hours. The cell growth was monitored simultaneously by Synergy H1 microplate reader (Biotek) using mCherry as a reporter protein (mCherry fluorescent signal directly correlates with the number of live bacterial cells). Data, as shown in FIG. 14A, represents the average of three biological replicates (n=3).

Dilution colony assay (Msmg colonies): The samples from the previously described procedure (Bacterial growth of Msmg culture) were also used for dilution colony assay as explained in the following text. After two hours of monitoring the bacterial growth in Synergy H1 microplate reader, 3 µL of each sample was collected and serially diluted in 1:10 ratio ($\times 10^{-1}$, $\times 10^{-2}$, $\times 10^{-3}$, $\times 10^{-4}$). Then 3 µL of each dilution was transferred onto 7H10+ agar plate and incubated at 30° C. for four days or until clear colonies were observed in the positive control sample (sample that didn't contain any inhibitor). The results of this experiment are summarized in FIG. 14B.

Inhibition of biofilm formation of Msmg, a phenotype for the inhibition of DNA replication: Msmg mc2155 were routinely cultured in Middlebrook 7H9 media (4.7 gm/L) supplemented with 0.2% v/v glycerol and 0.05% v/v Tween 80 and grown at 30° C. with shaking at 125 rpm for 48 h. For biofilm inhibition assay, the previously reported protocol was used with slight modifications. Briefly, freshly grown Msmg mc2155 was diluted in fresh biofilm growth media (Middlebrook 7H9 media with 0.2% glycerol supplemented with 0.5% glucose) 100 times (100 µl culture was diluted in 10 ml of media). 500 µl of diluted culture was dispensed in wells of a 48-well polystyrene plate for biofilm formation. To evaluate the inhibition of biofilm formation, compounds 13c, 13d (stock solution of 20 mM in DMSO) and isoniazid at 250 µM and 125 µM concentrations were added initially with diluted culture. Final concentration of DMSO in culture was 2.5% v/v in each well and only 2.5% DMSO was used in a control sample. The plate was sealed with parafilm and incubated at 37° C. in incubator for five days without shaking. After five days of incubation 0.1% Tween 80 was added to each well and gently swirled to dissolve the detergent. After 15 minute of incubation pellicles were collected and washed thrice with PBS containing 10% glycerol and 0.05% Tween 80. Pellicles were kept on rocker at 4° C. for 12 h in the same buffer for dispersal of matrix. Suspension was then homogenized by vortexing, diluted ten times in buffer and 90 µl of each sample was dispensed into 96 well polypropylene plates. 10 µl of alamar blue reagent as added in each well to check the viability of bacterial cells. Plate was further incubated at 37° C. for 8 h and percentage reduction of alamar blue was calculated by measuring fluorescence at excitation wavelength of 570 nm and emission wavelength of 600 nm. To further corroborate and validate the result of alamar blue assay the bacterial suspensions were diluted 10 times in PBS and 10 µl of each suspension was plated on a MH10 agar plate in order to count colony forming units (CFU). Some representative results of this experiment are shown in FIGS. 15A-B.

Example 4

Synthesis of Indole Derivatives

In exemplary procedures, a synthesis of indole derivative was performed.

The scheme in FIG. 9 summarizes the synthesis pathway, as performed in exemplary procedures described herein (the corresponding numbers are as indicated in FIG. 9).

General Procedure for the Synthesis of Compounds (2a-g)

Preparation of benzenediazonium salt derivatives (mixture I): To a well stirred solution of aniline derivatives 1a-g (10 mmol) in 5M aq. HCl (16 ml) at 0° C. a solution of sodium nitrite (1.38 g, 20 mmol, 2 equiv.) in 10 ml water previously cooled to 0-5° C. was added dropwise. The addition was slow in order to maintain the reaction temperature below 0° C. The resulting mixture was stirred at 0-5° C. for additional 30 min in an ice bath.

Preparation of 2-(ethoxycarbonyl)cyclopentanone anion (mixture II): A solution of 2-(ethoxycarbonyl)cyclopentanone (2.512 ml, 1.344 g, 15 mmol) in ethanol (5 ml) was cooled to 0-5° C. Then, a potassium hydroxide solution (5.040 g, 90 mmol, 6 equiv.) in water (5 ml) previously cooled to 0-5° C. was added slowly dropwise within 30 min in order to keep the temperature below 8° C. The white-milky appearance mixture was stirred for further 30 min at 0-5° C.

Preparation of monoethyl derivatives of phenylhydrazones: Ice (50 g) was added to mixture II with stirring at 0-5° C. in an ice bath, followed by the addition of mixture I, and stirring continued for 1 h at 50° C. The combined mixtures were then left to cool to room temperature and the pH was subsequently adjusted to 4-5 with 1 M aq. HCl. The desired product was extracted with diethyl ether (50 ml×3). The combined organic layers were collected, dried over magnesium sulfate, filtered, and the filtrate was evaporated to dryness yielding a gummy material (95-100%). This material was used without further purification for the next step.

Preparation of diethyl derivatives of phenylhydrazones (2a-g): To a solution of monoethyl derivatives (10 mmol) in absolute ethanol (100 ml), concentrated $H_2SO_4$ (2.7 ml, 50.5 mmol, 5.1 equiv.) was added dropwise. The reaction mixture was then heated to reflux for 3 h at 100° C. Then the ethanol was evaporated, and the residue was treated with 100 ml of ice water. The aqueous solution was extracted with dichloromethane (50 ml×3); the organic layer was dried over magnesium sulfate, filtered and concentrated. The residue was purified by silica gel column chromatography using 20% of ethyl acetate in hexane as eluent yielding solid in 80-95% yield.

General Procedure for the Synthesis of ethyl 3-(3-ethoxy-3-oxopropyl)-1H-indole-2-carboxylate derivatives (3a-g, 3c'): A mixture of p-toluenesulfonic acid (3.800 g, 20 mmol, 4 equiv.) and 100 ml of benzene was refluxed for 2 h at 110° C. under azeotropic condition. Subsequently, 5 mmol of the starting material (2a-g) was added and the mixture was refluxed for 24 h. Then it was allowed to cool down to room temperature, and benzene was removed by distillation. Saturated $NaHCO_3$ aqueous solution (30 ml×2) was added to quench the reaction and then washed with water. The crude mixture was extracted with dichloromethane. The organic layer was dried over magnesium sulfate, filtered, and evaporated to dryness. The residue was purified by silica gel column chromatography using 10-15% of ethyl acetate/hexane as eluent yielding solid in 15-80% yield.

Synthesis of compound 4a: Dry THF (20 ml) was added dropwise under $N_2$ atmosphere to an ice-cooled RBF containing LiAlH4 (342 mg, 9.0 mmol, 6 equiv.) at 0° C. After completion of THF addition, conc. $H_2SO_4$ (240 µl, 4.5 mmol, 3 equiv.) was added to the reaction mixture and the resulting mixture was left to stir at 0° C. for 30 min. To the stirred reaction mixture, compound 3a (1.5 mmol) in dry THF was added within 30 min and the resulting mixture was left to stir at room temperature for 2 h. After completion of the reaction, ice was added to the resulting reaction mixture and was filtered. Filter cake was washed with ethyl acetate and then with water. The organic phase was dried over magnesium sulfate and filtered. Solvent was removed under vacuum to produce grey solid. The residue was purified by silica gel column chromatography using 5% of dichloromethane/methane as eluent to yield the final products in 50% yield.

Synthesis of compound 5a: To the solution of compound 4a (0.05 mmol) in dry DCM (5 ml), PCC (32 mg, 0.15 mmol, 3 equiv.) was added. The reaction mixture was then stirred for 3 h at room temperature. After completion of the reaction, powdered $MgSO_4$ was added to the resulting reaction mixture and then anhydrous ether (5 ml×5) was added, 5× of reaction solvent (5 ml×5). The reaction mixture was then, filtered and concentrated. The residue was purified by silica gel column chromatography using 10-20% of ethyl acetate/hexane as eluent yielding solid in 40% yield.

Synthesis of compound 7a: To the stirred solution of compound 6a (0.08 mmole) in dry DMF (10 ml), HOBt (25 mg, 0.16 mmol, 2 equiv.) was added under inert conditions. Subsequently, solution of aniline (15 mg, 0.16 mmol, 2 equiv.) in dry DMF was added to the reaction mixture followed by the addition of DCC (34 mg, 0.16 mmol, 2 equiv.) and DIPEA (5%). The resulting mixture was left to stir at room temperature for 48 h. After completion of the reaction, reaction mixture was washed with 1M HCl (15 ml×3) followed by 0.1M $Na_2CO_3$ aqueous solution (20 ml×3) to quench the reaction. The crude mixture was extracted with ethyl acetate. The organic layer was then washed with brine (15 ml×3), dried over magnesium sulfate, filtered, and evaporated to dryness. The residue was purified by silica gel column chromatography using 15% of ethyl acetate in hexane as eluent yielding white solid in 60% yield.

General Procedure for the Synthesis of compounds (6a-g, 6c'), (8a-f, 8c'), (9a-f, 9c') and (11a-f, 11c'), (12a-f, 12c'), (13a-f, 13c'): Compound 3a-g, 3c' (0.5 mmol) and 10a-f, 10c' (0.5 mmol) were dissolved in 50 ml tetrahydrofuran (THF) and the mixture was stirred at room temperature. Solution of NaOH (0.01M) was added to the stirred reaction mixture and left to stir at room temperature for 18-24 h. After completion of the reaction, the pH was adjusted to 2-3 using 1M aq. HCl, and the product was extracted with diethyl ether (20 ml×3). The organic layers were dried over magnesium sulfate, filtered, and evaporated to dryness. The residue was purified by silica gel column chromatography using 10-50% of ethyl acetate/hexane as eluent to yield the final products (6a-g, 6c'), (8a-f, 8c'), (9a-f, 9c') and (11a-f, 11c'), (12a-f, 12c'), (13a-f, 13c') as white solids in different (10-75%) yields.

General Procedure for the Synthesis of N— benzylated derivatives of ethyl 3-(3-ethoxy-3-oxopropyl)-1H-indole-2-carboxylate (10a-f, 10c'): To the solution of compounds 3a-f, 3c' (0.5 mmol) in DMF (20 ml), $Cs_2CO_3$ (488 mg, 1.5 mmol, 3 equiv.), a catalytic amount of KI, and benzyl bromide (214 mg, 1.25 mmol, 2.5 equiv.) were added. The reaction mixture was heated to 60° C. for 2 h, and then concentrated under vacuum. The residue was dissolved in EtOAc (25 ml), washed with water (10 ml×3), dried with anhydrous $MgSO_4$ and concentrated under reduced pressure. The crude product, if required, was purified by silica gel column chromatography to provide compound (10a-f, 10c') as yellow oil (100%).

Example 5

Synthesis of CPP Conjugates

FIG. 10E represents chemical structures of CPP conjugates synthesized according to the exemplary procedure described herein.

The Fmoc based solid phase peptide synthesis strategy was used for the synthesis of TAT peptide GRKKRRQRRRPQ-CONH$_2$ (SEQ ID NO:1) and octaarginine RRRRRRRR-CONH$_2$ (SEQ ID NO:1) on Rink amide MBHA resin by using an automated peptide synthesizer (Tribute-UV, Protein Technologies). All the coupling reactions were performed using HBTU coupling with 4 equivalents of the amino acid and 8% of diisoproylethylamine in DMF. For deprotection of Fmoc group, 25% v/v piperidine in DMF was used. Upon completion of synthesis of peptide on resin, compound 13d was conjugated to the N-terminal of last amino acid using HBTU and DIPEA for 4 h. To cleave the resin bound conjugated peptides, a cleavage mixture comprising TFA/thioanisole/phenol/ethanedithiol/H₂O (91.25:2.5:2.5:1.25:2.5) was used. Purification of the conjugated peptide was done on C-18 RP-HPLC column with linear gradients of water containing 0.1% TFA (gradient A) and acetonitrile containing 0.1% TFA (gradient B). The correct mass of sequences after purification was characterized by LC-ESI-MS (Thermo Surveyor 355).

Example 6

Inhibiting Bacterial DNA Primase and Gyrase

In exemplary procedures, the synthesized derivative molecules were tested for their ability to inhibit RNA primers formation by *M. tuberculosis* DnaG primase. These results are presented in FIGS. 11A-C. Some of the derivatives show total primase inhibition, as evident from the decrease in the RNA product formation.

In additional exemplary procedures, the derivatives synthesized were examined for their ability to inhibit DnaG primase using standard assays. DNA primase shares common motifs arrangements at the active site with GyrB (see FIGS. 12A-B) and therefore it was assumed, without being bound by any particular mechanism, that some of the designed molecules could potentially target bacterial gyrase, and therefore may be effective target that yield bactericidal drugs used in the clinic. The DnaG gene in *A. aeolicus* comprises the sequence GFAILVEGYFDLLRLFSALTQNQANLLSKF TKKVYILYDGDDAGRKAMKSAIPLLLSAGVEVYPVYLPEGEGIRNVVAPLGT (SEQ ID NO: 1). In *S. aureus* the DnaG gene comprises the sequence DEIVLLEGFM DVIKSDTAGLKNVVATMGTQLSDEHITFIRKLTSNITLMFDGDFAGSEATLKT GQHLLQQGLNVFVIQLPSG (SEQ ID NO:2). The homologous gene is Bacteriophage T7 comprises the sequence KKIVVTEGEIDMLTVMELQD CKYPVVSLGHGASAAKKTCAANYEYFDQFREQIILMFDMDEAGRKAVEEAA QVLPAGKVRVAVLPCKDA (SEQ ID NO: 3). These three regions could be aligned with the sequence SELYVVEGDSAGGSAKSGRDSMFQAILPLRGKIINVEKAR IDRVLKNTEVQAIITALGTGIHDEFDIGKLRYHKIVLMADADVDGQHISTLLLT LLFRFM RPLIENGHVFLAQPP (SEQ ID NO: 4) of GyrB in *M. tuberculosis* as is illustrated in FIG. 12A.

As shown in FIG. 11C and FIG. 13, some molecules synthesized that target DnaG primase also effectively inhibit Gyrase, and therefore may be an effective target that yield bactericidal drugs used in the clinic.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The invention claimed is:

1. A compound or a pharmaceutically acceptable salt thereof, wherein said compound is represented by Formula II:

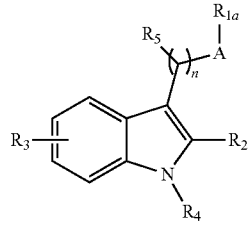

wherein:
n equals 0 to 10;
A is a covalent bond selected from the group consisting of:

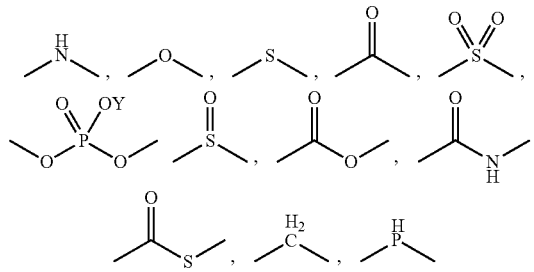

wherein Y is an alkyl group; $R_{1a}$ comprises a peptide;
each $R_5$ is independently selected from the group consisting of: hydrogen, a $C_1$-$C_{12}$ alkyl group, an aryl group, a $C_4$-$C_{20}$ cycloalkyl group, a mercapto group, an amino, a hydroxy group, a halo group, a cyano group, a nitro group, carboxylate, ester, amide, carbonyl, anhydride, carbonate ester, carbamate, a $C_1$-$C_{10}$ alkyl group comprising a heteroatom, a haloalkyl group, an alkoxy group, an alkylhydroxy group, a sulfinyl group, a sulfone group, a sulfonate group, and a phosphine group;
$R_2$ is selected from the group consisting of: an alkyl group, a peptide, —(CH$_2$)$_{0-5}$—C(O)OR$^b$, —(CH$_2$)$_{0-5}$—C(O)SR$^b$, and —(CH$_2$)$_{0-5}$—C(O)NR$^b$, wherein R$^b$ is selected from the group consisting of: hydrogen, a $C_1$-$C_6$ alkyl group, an aryl group, and a heteroaryl group;
R4 is selected from the group consisting of hydrogen, an alkylaryl group, an alkyl group, an aryl group, a heteroaryl group, a sulfinyl group, a sulfonate group, a cycloalkyl group, and a heterocyclyl group or a combination thereof,
and $R_3$ represents up to three substituents, being independently selected from the group consisting of: a trihalomethyl group, a fluorinated alkyl group, a cyano group, a nitro group, a halo group, a sulfonyl group, a sulfonate group, a sulfinyl group, a sulfonamide group, an azo group, a guanidine group, carboxylate, ester, amide, carbonyl, anhydride, carbonate ester, and carbamate.

2. The composition of claim 1, wherein $R_3$ represents up to three substituents, being independently selected from the group consisting of: a nitro group, a fluorinated alkyl group, and a halo group.

3. The composition of claim 1, wherein said compound is selected from the group consisting of:

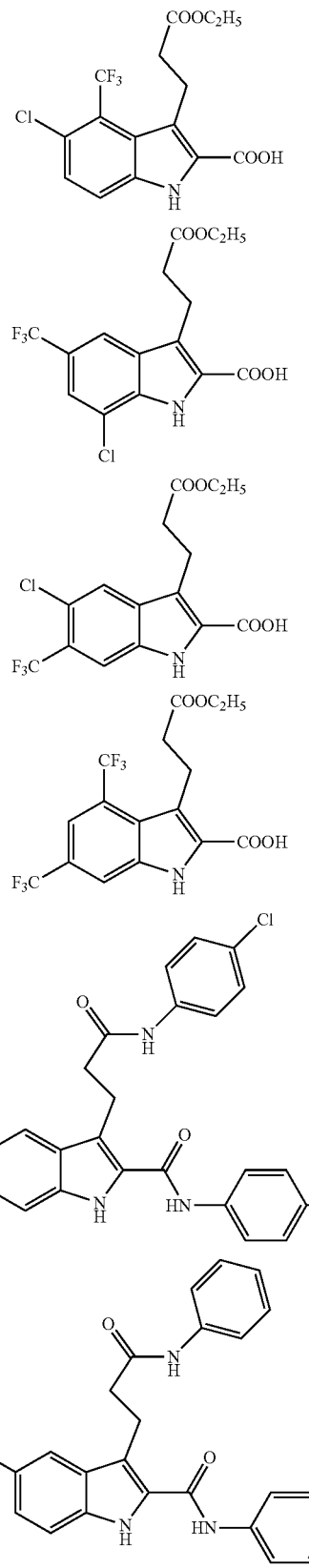

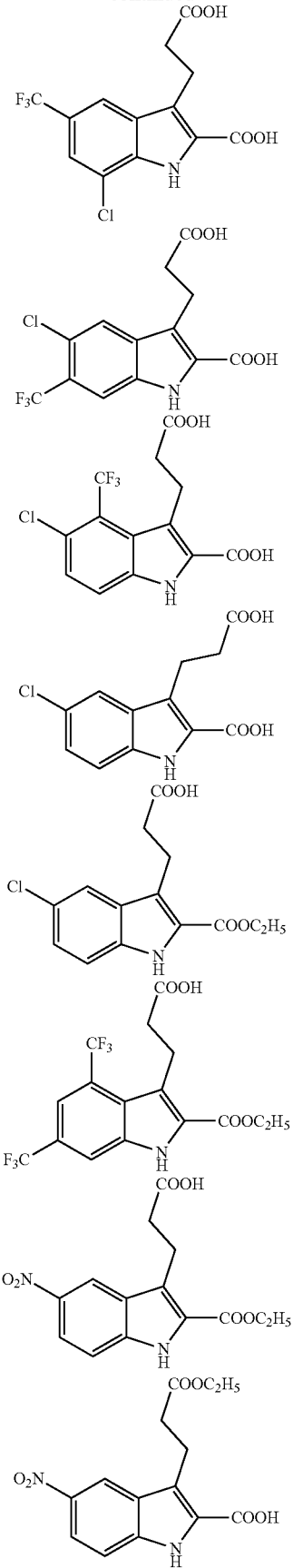
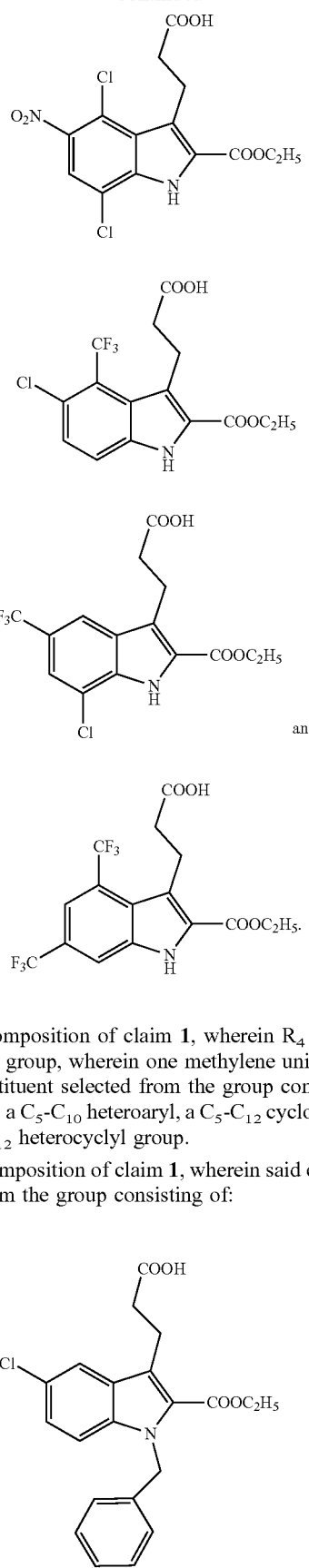
4. The composition of claim 1, wherein $R_4$ comprises a $C_1$-$C_3$ alkyl group, wherein one methylene unit is replaced with a substituent selected from the group consisting of: a $C_6$-$C_{10}$ aryl, a $C_5$-$C_{10}$ heteroaryl, a $C_5$-$C_{12}$ cycloalkyl group, and a $C_5$-$C_{12}$ heterocyclyl group.
5. The composition of claim 1, wherein said compound is selected from the group consisting of:
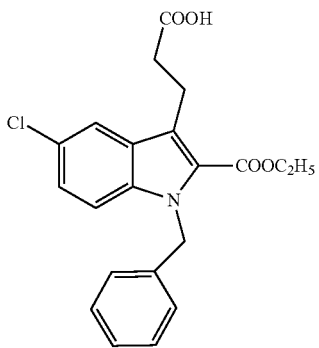

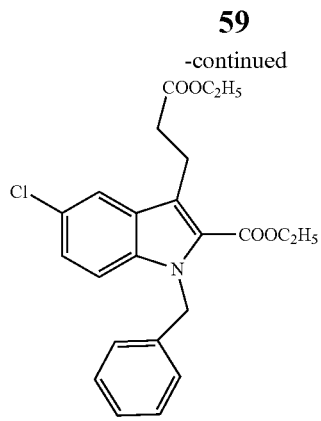

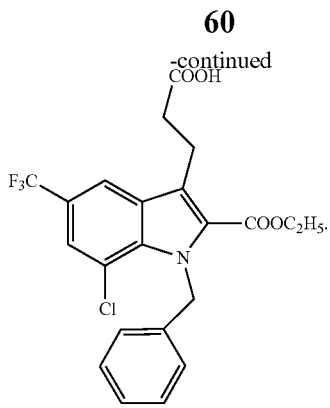

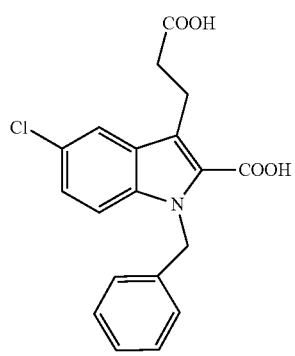

6. The composition of claim 1, wherein said compound is represented by Formula III:

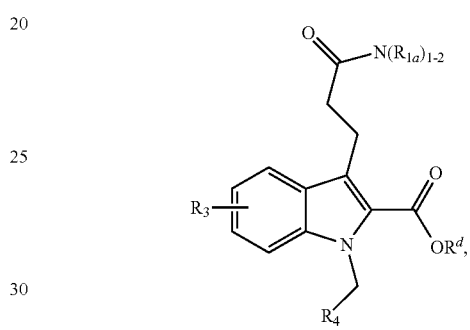

wherein:

$R^d$ is selected from the group consisting of: an ethyl group, a methyl group, a propyl group, and hydrogen; and $R_{1a}$ comprises a peptide.

7. The composition of claim 1, wherein $R_4$ is selected from the group consisting of:

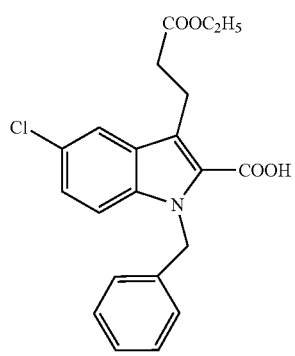

and

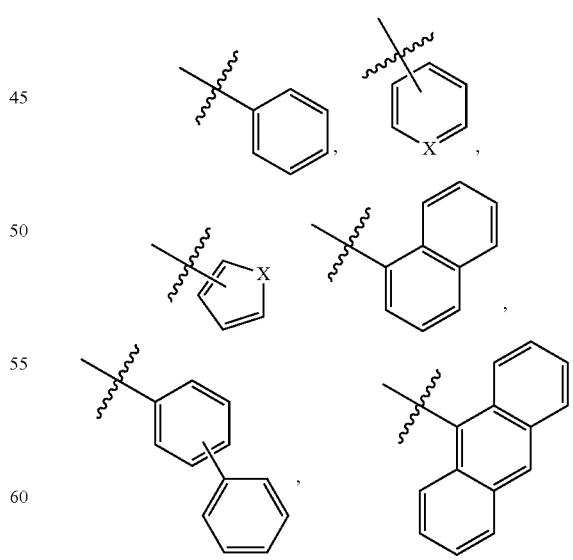

wherein X is a heteroatom.

8. The composition of claim 1, wherein said compound is selected from Formulae IV and V:

Formula IV

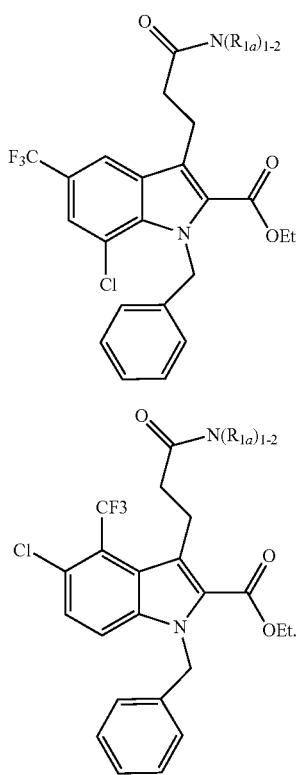

Formula V

9. The compound of claim 1, wherein said peptide comprises a cell penetrating peptide.

10. The compound of claim 9, wherein said cell penetrating peptide comprises a sequence of 3 to 60 amino acids.

11. The compound of claim 9, wherein said sequence is selected from the group consisting of: SEQ ID NO: 1 (GRKKRRQRRRPQ); and SEQ ID NO: 2 (RRRRRRRR) or any combination thereof.

12. The compound of claim 1, wherein said compound is represented by Formula IVa:

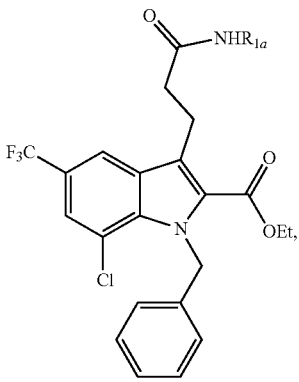

and wherein $R_1a$ is SEQ ID NO: 1.

13. The compound of claim 1, wherein R4 comprises alkylaryl.

14. A pharmaceutical composition comprising a therapeutically effective amount of one or more compounds of claim 1, and a pharmaceutically acceptable carrier.

15. A method of killing bacteria or inhibiting bacterial reproduction, the method comprises contacting said bacteria with one or more compounds of claim 1, thereby killing said bacteria or inhibiting said bacteria from reproducing.

16. The method of claim 15, wherein said inhibiting bacterial reproduction is by inhibiting one or more enzymes selected from the group consisting of: DNA primase, and DNA gyrase.

17. The method of claim 16, wherein said method is for treating a subject afflicted with microbial infection.

* * * * *